US010646152B2

(12) United States Patent
Nims et al.

(10) Patent No.: US 10,646,152 B2
(45) Date of Patent: *May 12, 2020

(54) ATHLETIC PERFORMANCE MONITORING SYSTEM UTILIZING HEART RATE INFORMATION

(71) Applicant: NIKE, Inc., Beaverton, OR (US)

(72) Inventors: Jason Nims, Portland, OR (US); Matthew Capozzi, Portland, OR (US); Michael B. Hailey, Forest Grove, OR (US); Kwamina Crankson, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 186 days.

This patent is subject to a terminal disclaimer.

(21) Appl. No.: 15/865,886

(22) Filed: Jan. 9, 2018

(65) Prior Publication Data

US 2018/0192934 A1 Jul. 12, 2018

Related U.S. Application Data

(63) Continuation of application No. 12/964,139, filed on Dec. 9, 2010, now Pat. No. 9,895,096.
(Continued)

(51) Int. Cl.
A61B 5/02 (2006.01)
A61B 5/22 (2006.01)
A63B 24/00 (2006.01)

(52) U.S. Cl.
CPC .......... A61B 5/222 (2013.01); A63B 24/0062 (2013.01); A63B 2024/0065 (2013.01);
(Continued)

(58) Field of Classification Search
CPC .......... A61B 5/22; A61B 5/222; A63B 24/00; A63B 24/0062; A63B 2230/06; A63B 2220/00; A63B 2225/50; A63B 2024/0065
See application file for complete search history.

(56) References Cited

U.S. PATENT DOCUMENTS 5,375,199 A 12/1994 Harrow et al.
6,259,944 B1 7/2001 Margulis et al.
(Continued)

FOREIGN PATENT DOCUMENTS

CN 101367011 A 2/2009
JP H09056705 9/1997
(Continued)

OTHER PUBLICATIONS

Jun. 17, 2011—(WO) ISR & WO—App. No. PCT/US10/059656.

Primary Examiner — Eric J Messersmith
(74) Attorney, Agent, or Firm — Banner & Witcoff, Ltd.

(57) ABSTRACT

Athletic activity may be monitored using heart rate in addition to or instead of other types of metrics. Accordingly, multiple different activity types may be compared based on heart rate information. Additionally, the heart rate information may be visualized by displaying the heart rate data over time or relative to pace or distance. Additionally, the system may allow a user to analyze his or her heart rate performance by identifying one or more portions of the athletic activity in which a user exhibited a specified range of heart rates. Athletic activity sessions may further be tagged with various indicators including weather, terrain, difficulty and intensity. According to one or more aspects, data for different types of activity metrics may be polled and/or transmitted to a system at different rates or based on different schedules. Moreover, users may specify whether sensed data may be uploaded,
(Continued)

recorded and/or visualized prior to or during an activity session.

10 Claims, 43 Drawing Sheets

Related U.S. Application Data

(60) Provisional application No. 61/285,049, filed on Dec. 9, 2009.

(52) U.S. Cl.
CPC ....... *A63B 2220/00* (2013.01); *A63B 2225/50* (2013.01); *A63B 2230/06* (2013.01)

(56) References Cited

U.S. PATENT DOCUMENTS

| | | |
|---|---|---|
| 7,670,263 B2 | 3/2010 | Ellis et al. |
| 8,200,323 B2 | 6/2012 | DiBenedetto et al. |
| 2002/0042328 A1 | 4/2002 | Yoo |
| 2003/0181291 A1 | 9/2003 | Ogawa |
| 2004/0102931 A1 | 5/2004 | Ellis et al. |
| 2006/0047201 A1 | 3/2006 | Eide |
| 2006/0084551 A1 | 4/2006 | Volpe |
| 2007/0011919 A1 | 1/2007 | Case |
| 2007/0118043 A1 | 5/2007 | Oliver et al. |
| 2007/0208544 A1 | 9/2007 | Kulach et al. |
| 2008/0096726 A1 | 4/2008 | Riley et al. |
| 2008/0200310 A1 | 8/2008 | Tagliabue |
| 2009/0033034 A1 | 2/2009 | Jakubowski |
| 2009/0048070 A1 | 2/2009 | Vincent et al. |
| 2010/0062905 A1 | 3/2010 | Rottler et al. |

FOREIGN PATENT DOCUMENTS

| | | |
|---|---|---|
| JP | 2003175139 A | 6/2003 |
| JP | 2007117719 A | 5/2007 |
| JP | 2009050699 A | 3/2009 |
| JP | 2009078134 A | 4/2009 |
| JP | 2009535157 A | 10/2009 |
| KR | 10-0498794 B1 | 7/2006 |
| KR | 20080022680 | 3/2008 |
| WO | 2009033034 A1 | 3/2009 |
| WO | 2009111472 A2 | 9/2009 |

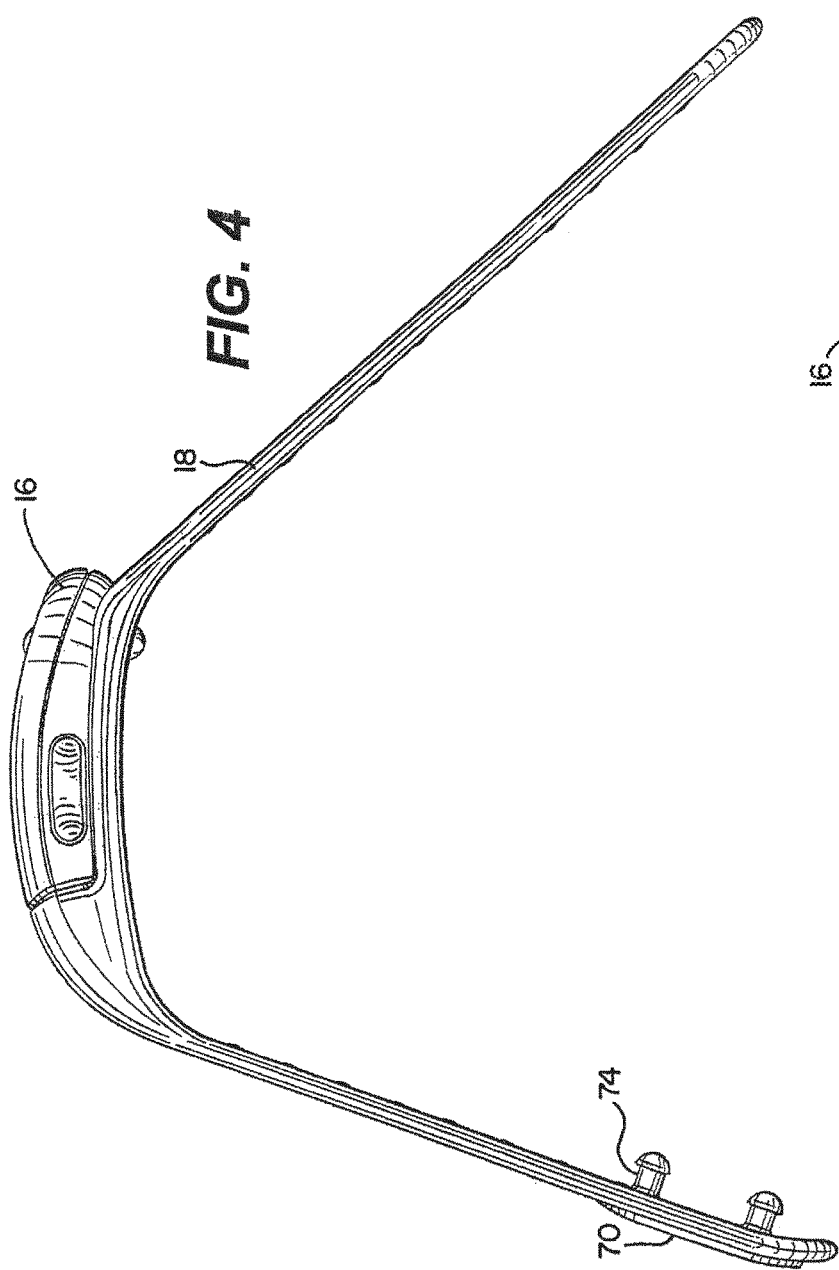
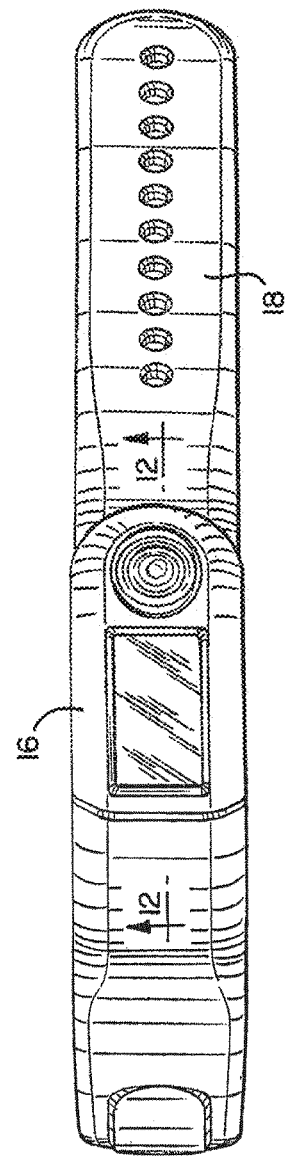
FIG. 4
FIG. 5

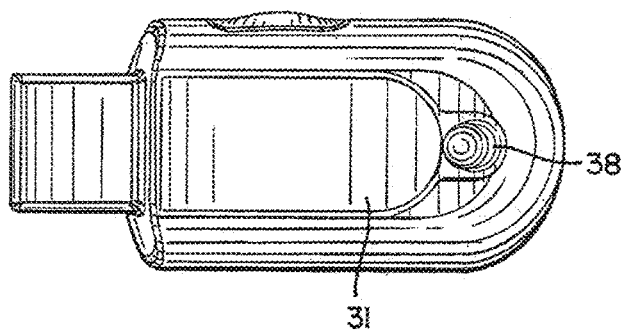
FIG. 9
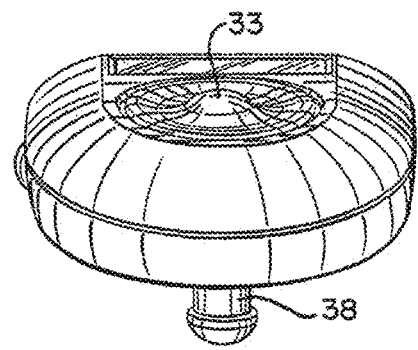
FIG. 10
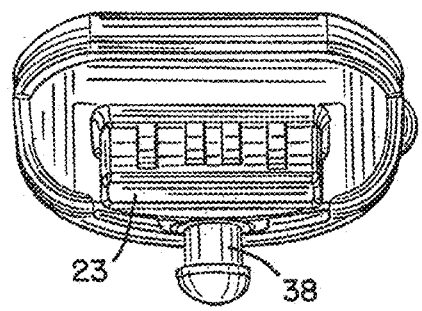
FIG. 11
FIG. 12
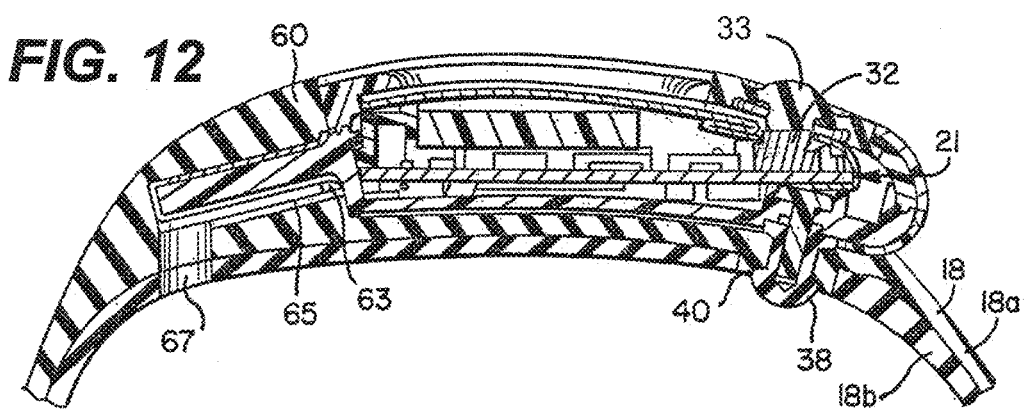

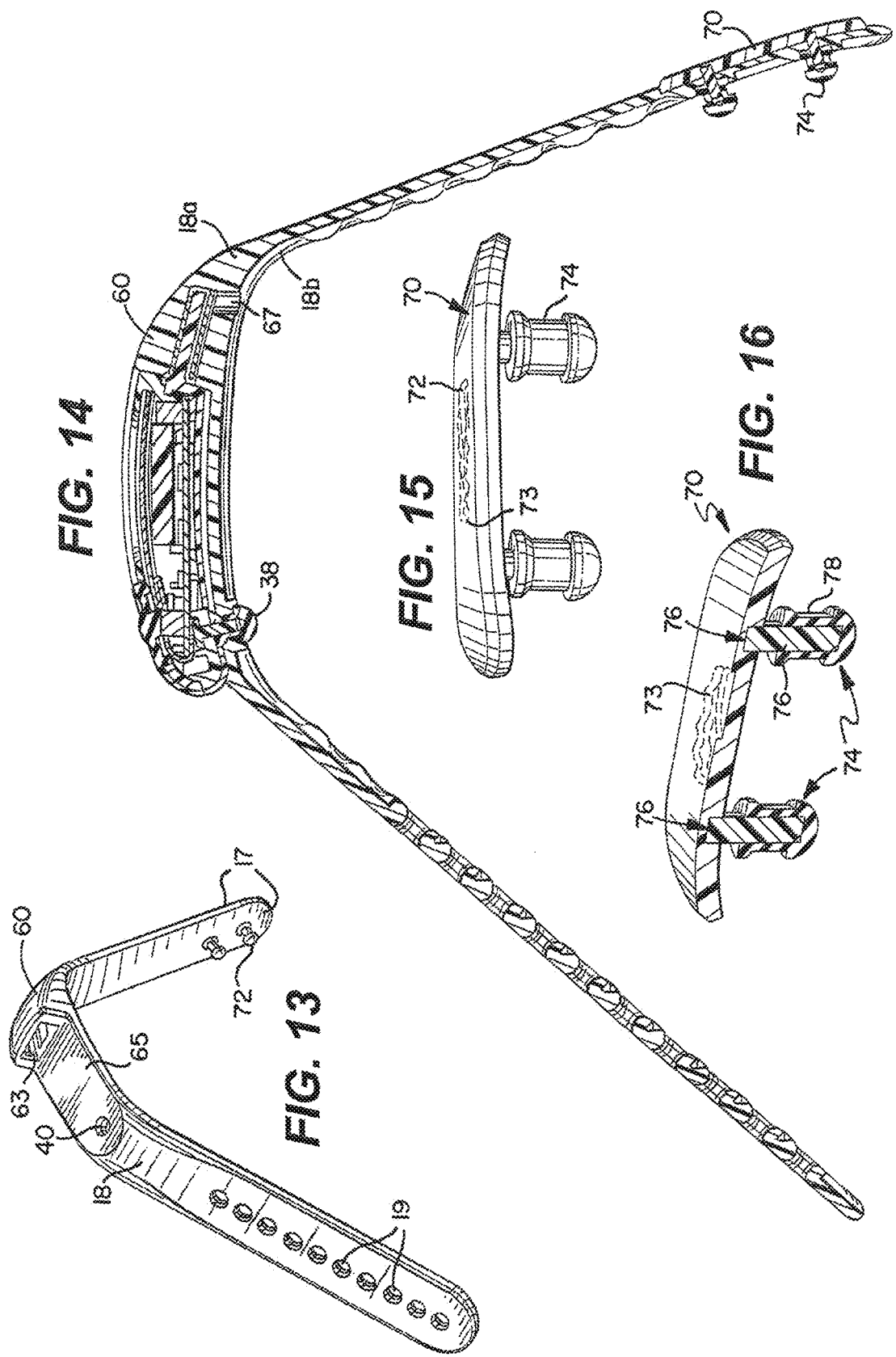

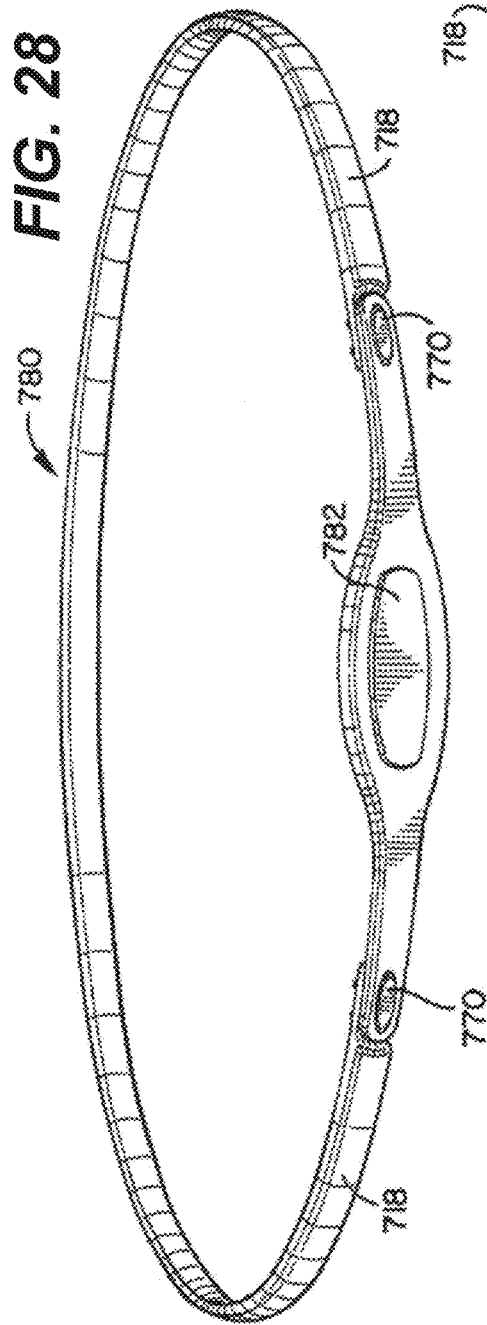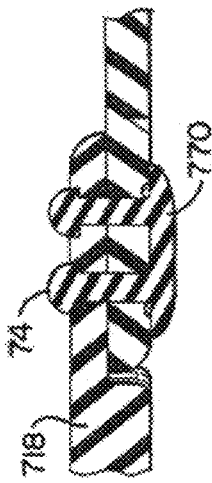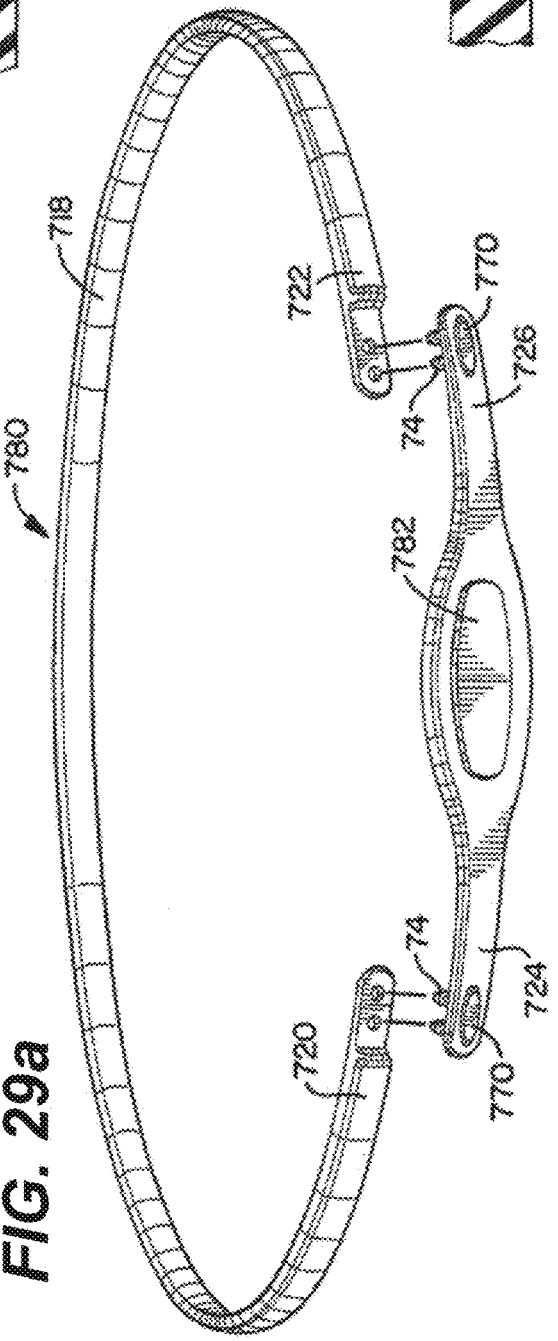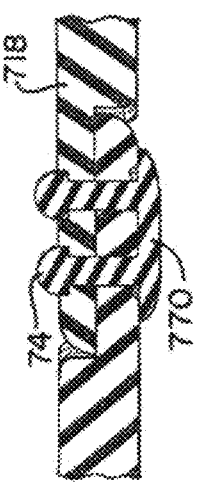

ATHLETIC PERFORMANCE MONITORING SYSTEM UTILIZING HEART RATE INFORMATION

CROSS REFERENCE TO RELATED APPLICATION

This application is a continuation of U.S. application Ser. No. 12/964,139, filed Dec. 9, 2010, which claims the benefit of priority from U.S. Application Ser. No. 61/285,049, filed Dec. 9, 2009. The content of the above noted applications is incorporated herein by reference in its entirety for any and all non-limiting purposes.

TECHNICAL FIELD

The invention relates generally to athletic performance monitoring systems, and more particularly, to such systems that utilize heart rate information.

BACKGROUND

Exercise and fitness have become increasingly popular and the benefits from such activities are well known. Various types of technology have been incorporated into fitness and other athletic activities. For example, a wide variety of portable electronic devices are available for use in fitness activities, such as MP3 or other audio players, radios, portable televisions, DVD players, or other video playing devices, watches, GPS systems, pedometers, mobile telephones, pagers, beepers, etc. Many fitness enthusiasts or athletes use one or more of these devices when exercising or training to keep them entertained, provide athletic performance data, to keep them in contact with others, etc.

Advances in technology have also provided more sophisticated athletic performance monitoring systems. Athletic performance monitoring systems enable easy and convenient monitoring of many physical or physiological characteristics associated with exercise and fitness activity, or other athletic performances including, for example, speed and distance data, altitude data, GPS data, heart rate, pulse rate, blood pressure data, body temperature, etc. This data can be provided to a user through a portable electronic device carried by the user. For example, one athletic performance monitoring system may incorporate a wrist worn device that may also communicate with other devices such as an audio player and/or a heart rate monitor worn by the user. While athletic performance monitoring systems according to the prior art provide a number of advantageous features, they nevertheless have certain limitations. For example, prior athletic performance monitoring systems have not utilized heart rate information in a manner that provides more useful analysis to the user. Aspects of the present disclosure seek to overcome certain of these limitations and other drawbacks of the prior art, and to provide new features not heretofore available. Heart rate may be used to monitor and compare athletic activities since heart rate is generally considered one of the more accurate ways to evaluate amount of calories burned and amount of activity performed.

A full discussion of the features and advantages of the present invention is deferred to the following detailed description, which proceeds with reference to the accompanying drawings.

BRIEF SUMMARY

The following presents a general summary of aspects of the invention in order to provide a basic understanding of at least some of its aspects. This summary is not an extensive overview of the invention. It is not intended to identify key or critical elements of the invention or to delineate the scope of the invention. The following summary merely presents some concepts of the invention in a general form as a prelude to the more detailed description provided below.

The present invention provides an athletic performance monitoring system that utilizes heart rate information.

According to at least one aspect of the invention, a user has a wrist worn device in operable communication with a heart rate monitor. Heart rate information is conveyed to the user in an enhanced manner. In addition, in an exemplary embodiment, heart rate information is capable of being conveyed to the user via a separate medium, such as a remote website. An athletic performance monitoring device, such as the wrist worn device, may be configured to detect and collect information from multiple sensors. For example, the wrist worn device may collect data from both a heart rate sensor as well as a shoe based sensor such as an accelerometer or pedometer. The athletic performance monitoring device may include a display that indicates whether various sensors have been detected and provides the user with options to initiate a workout.

According to another aspect, heart rate and/or pace information may be visualized by graphing heart rate and pace over distance or time. In one example, a pace graph may include a pace line with multiple markers displayed thereon. The markers may be indicative of particular points in the workout such as distances (every quarter mile, every mile, etc.) or time (e.g., every 30 minutes, every hour or the like). Heart rate markers may also be provided to identify the points in the workout where the athlete reached his highest heart rate and lowest heart rate. Progress markers and heart rate markers may be different in appearance to help the user differentiate between heart rate information and progress information. The highest heart rate and the lowest heart rate may be determined from a portion of the workout not including a warm up period and/or a cool down period. In one or more arrangements, heart rate markers may also be provided at the beginning and the end of the workout graph. Other workout information may also be displayed or visualized including duration information and distance information.

According to another aspect, an athlete's workout information collected in an athletic performance monitoring device may be transmitted to an athletic performance monitoring site or application situated on a device or server other than the monitoring device. For example, the collected data may be transmitted to a third party athletic performance monitoring site on a remote server where the data may be collected, stored, visualized and compared with other users of the site. The manner in which the athlete's workout information is processed may be specified by the user pre-, during and/or post-workout. For example, a user may specify whether data is to be recorded, transmitted and/or visualized.

According to another aspect, a user's workout information including heart rate and pace may be compared with other users. For example, a comparison of the user's workout with the average workout of friends or all other users of an athletic performance monitoring site may be generated. Such comparisons may provide the user with motivation to increase their workouts or improve in their performance.

According to yet another aspect, a visualization of a workout may be customized to identify portions of a workout in which a user exhibited a particular range of heart rates. In one example, the user may adjust upper and lower limit sliders on a slider bar to define the upper and lower limits for a range of heart rates that are to be identified in a chart. The portions of the workout matching the selected heart rate range may be overlaid by a bar or indicator to visually identify the portions. Additionally or alternatively, multiple ranges may be identified simultaneously in a workout graph using different colors, patterns, hues, and the like. Furthermore, predefined ranges may be displayed for user selection. These predefined ranges may be a system default or may be defined based on user preferences or may be configured by a third party such as a coach. An interface configured to identify such workout portions may further indicate a percentage of the workout or an amount of workout time that falls in the specified range.

According to yet another aspect, an athlete's workouts may be summarized according to an amount of time or percentage of the workouts spent in various heart rate ranges. The athlete may further be allowed to define the heart rate ranges and target percentages for each heart rate range. An alert may then be created to alert the athlete whenever his or her workouts are within the specified target percentages. Some tolerance may be provided for determining when an athlete has reached a specified target percentage. For example, if 8% of an athlete's workout is within the 170-180 bpm heart rate range and the athlete has defined a target of 10% for that heart rate range, the workout may be determined to have achieved the goal of 10%.

According to yet another aspect, trendlines may be generated for a user's workout. For example a heart rate trendline may be generated to indicate a level of progress made by the user during a workout. Trendlines for other metrics (e.g., pace, distance, amount of weight lifted, etc.) may also be generated.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 4 is a side elevation view of the device assembly shown in FIG. 3;

FIG. 5 is a plan view of the device assembly shown in FIG. 3;

FIG. 9 is a bottom plan view of the device shown in FIG. 6;

FIG. 10 is an end view of the device shown in FIG. 6;

FIG. 11 is an opposite end view of the device shown in FIG. 6;

FIG. 12 is a partial cross-sectional view of the device taken along line 12-12 of FIG. 5;

FIG. 13 is a perspective view of the carrier or wristband of the device assembly of FIG. 3 and having the device of FIG. 6 removed according to one or more aspects described herein;

FIG. 14 is a cross-sectional view of the device assembly of FIG. 3;

FIG. 15 is a perspective view of a removable closure used with the wristband according to one or more aspects described herein;

FIG. 16 is a schematic cross-sectional view of the removable closure shown in FIG. 15;

FIG. 28 is a perspective view of an embodiment of a heart rate monitor assembly with a removable closure assembly according to one or more aspects described herein;

FIG. 29a is an exploded perspective view of the heart rate monitor assembly of FIG. 28;

FIGS. 29b and 29c are partial cross-sectional views of the removable closure assembly of FIG. 28;

DETAILED DESCRIPTION

Figure 1:
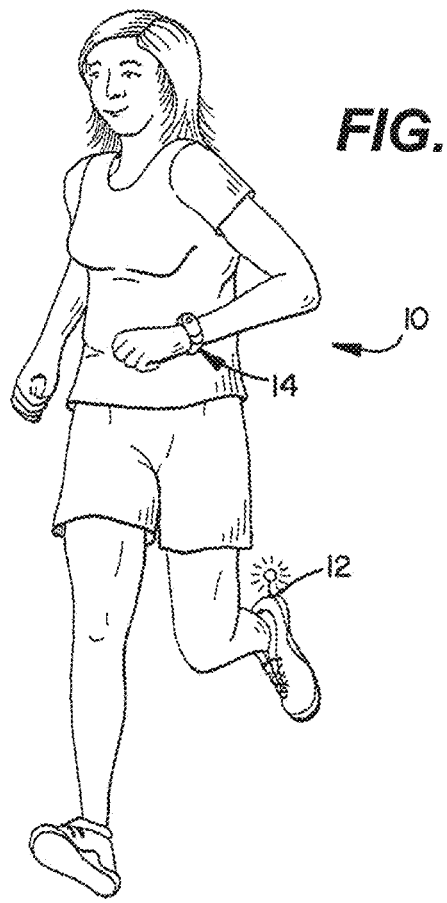
FIG. 1 is a perspective view of a runner wearing a device assembly used in an athletic performance monitoring system according to one or more aspects described herein.

In the following description of various example embodiments of the invention, reference is made to the accompanying drawings, which form a part hereof, and in which are shown by way of illustration various example devices, systems, and environments in which aspects of the invention may be practiced. It is to be understood that other specific arrangements of parts, example devices, systems, and environments may be utilized and structural and functional modifications may be made without departing from the scope of the present invention. Also, while the terms "top," "bottom," "front," "back," "side," and the like may be used in this specification to describe various example features and elements of the invention, these terms are used herein as a matter of convenience, e.g., based on the example orientations shown in the figures. Nothing in this specification should be construed as requiring a specific three dimensional orientation of structures in order to fall within the scope of this invention.

GENERAL DESCRIPTION OF ASPECTS OF THE INVENTION

Aspects of the present disclosure provide an athletic performance monitoring system and data collection site. The monitoring system may include wearable devices that are configured to sense and collect data from one or more sensors including pace detection sensors and heart rate sensors. The collected data may then be visualized and displayed in a variety of ways to convey various types of information to the athlete.

In one or more configurations, an athletic performance monitoring device may include a USB device having athletic functionality. In one exemplary embodiment, the USB device is a part of an assembly having a carrier wherein the USB device is wearable. In addition, the USB device has a controller that is configured to communicate athletic performance data. The communication may include any or all of one of the following: receiving data, displaying data, transferring data, and recording data. The controller communicates with a sensor to record and monitor athletic performance as an overall athletic performance monitoring system. In one or more configurations, the USB device may comprise a watch or other wearable electronic information device. Accordingly, the USB device may provide functionality beyond the transfer and/or display of athletic performance data. For example, the USB device may display time, play audio and/or video, provide telecommunication capabilities and the like. Additionally or alternatively, a USB device such as a watch may further include short-range and/or long range wireless communication capabilities including BLUETOOTH and WI-FI.

The USB device is connected to a carrier that in one exemplary embodiment is a wristband. The USB device and wristband have a cooperative structure to removably connect the USB device to the wristband. In one exemplary embodiment, the USB device has a protrusion and the wristband has an opening or recess. The protrusion is inserted into the opening wherein the USB device is connected to the wristband. The wristband has a removable closure. The closure has an indicia-bearing plate having posts that cooperate with openings in the wristband to secure the wristband on a user. The closure is removable wherein different closures bearing different indicia can be utilized with the wristband.

The USB device has a housing supporting the controller therein. The housing has a structural configuration wherein the housing is water-resistant as well as impact resistant.

The controller utilizes a user interface having certain features to enhance the functionality of the device. The USB device has a display wherein performance data can be displayed to the user. The USB device can be plugged into a computer wherein performance data can be automatically uploaded to a remote site for further display and review.

In addition, the carrier can take other forms wherein the USB device can be worn by a user in a various different locations.

EXAMPLES

While aspects of the invention generally have been described above, the following detailed description, in conjunction with the Figures, provides even more detailed examples of athletic performance monitoring systems and methods in accordance with examples of this invention. Those skilled in the art should understand, of course, that the following description constitutes descriptions of examples of the invention and should not be construed as limiting the invention in any way.

FIG. 1 generally discloses an athletic performance monitoring system 10 that in one exemplary embodiment of the invention includes a wearable device having athletic functionality. As shown in FIG. 1, the athletic performance monitoring system 10 generally includes a module or sensor 12 and a wearable device assembly 14. As discussed in greater detail below, the sensor 12 and wearable device assembly 14 wirelessly communicate with one another to record and monitor athletic performance.

The sensor 12 may have various electronic components including a power supply, magnetic sensor element, microprocessor, memory, transmission system and other suitable electronic devices. The sensor 12 in one exemplary embodiment is mounted on the shoe of a user as shown in FIG. 1. Alternatively or additionally, sensor 12 may include a heart rate sensor that is worn in other locations of a user's body. The sensor 12 is used in conjunction with the other components of the system to record speed and distance among other parameters of athletic performance such as heart rate. The sensor 12 can be a sensor as disclosed in U.S. Publication Nos. 2007/0006489; 2007/0011919 and 2007/0021269. These U.S. Publications are incorporated by reference herein and made a part hereof. In one or more arrangements, multiple sensors may be used in conjunction with assembly 14.

Figure 2:
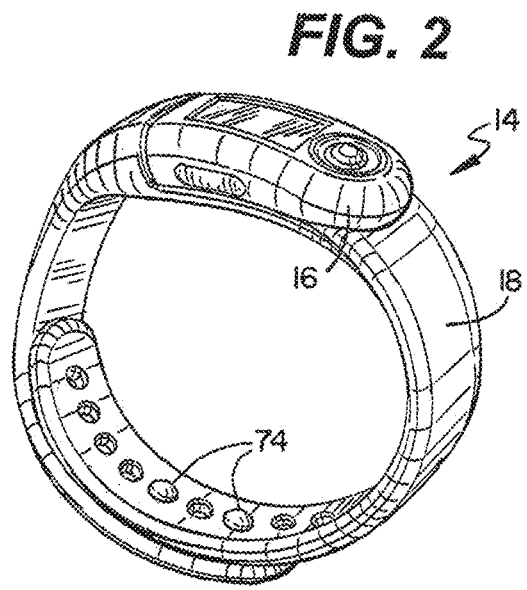
FIG. 2 is a perspective view of the wearable device assembly shown in FIG. 1.
Figure 3:
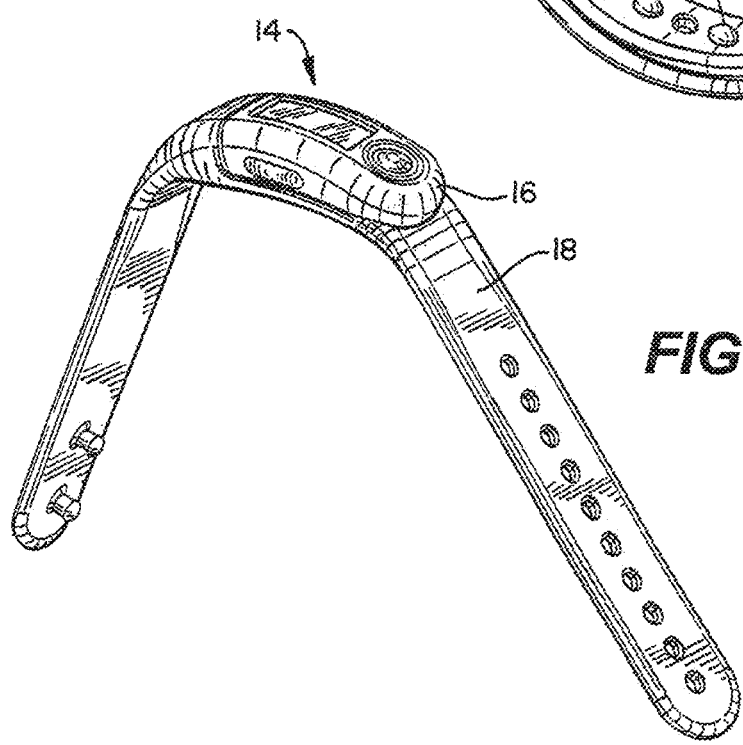
FIG. 3 is a perspective view of the wearable device assembly shown in FIG. 1, with a wristband of the device in an unfastened position according to one or more aspects described herein.
Figure 6:
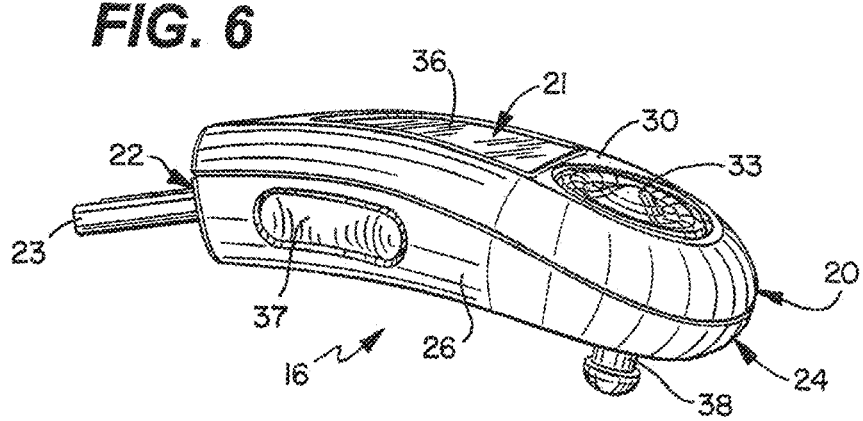
FIG. 6 is a perspective view of a USB-type device of the wearable device assembly according to one or more aspects described herein.
Figure 7:
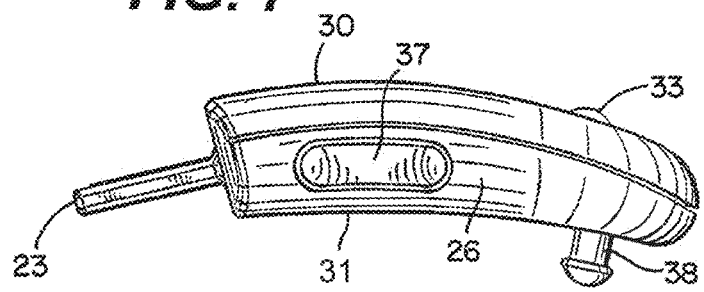
FIG. 7 is a side elevation view of the device shown in FIG. 6.
Figure 8:
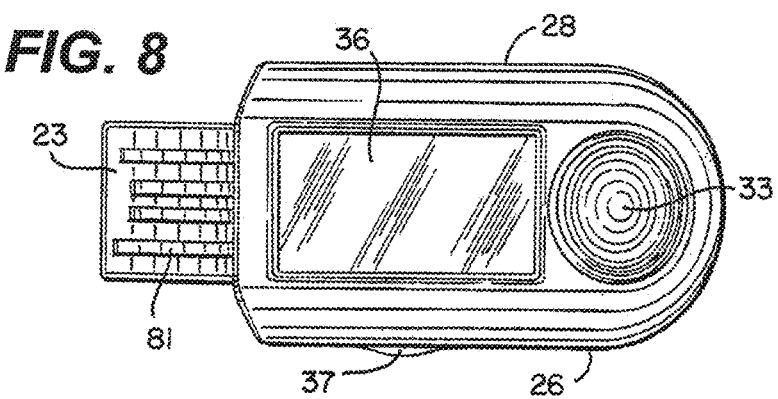
FIG. 8 is a top plan view of the device shown in FIG. 6.
Figure 17:
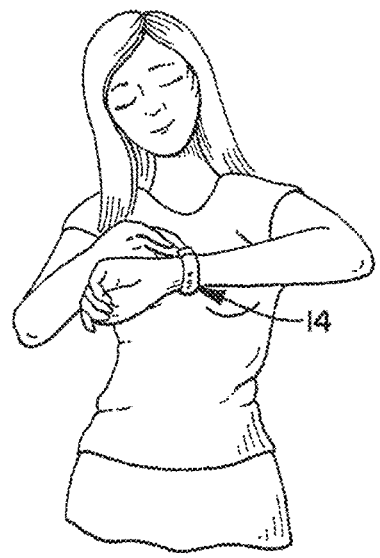
FIG. 17 is a partial perspective view of a runner setting the device according to one or more aspects described herein.

With reference to FIG. 2, the wearable device assembly 14 generally includes a wearable device 16 that in one exemplary embodiment is a USB (Universal Serial Bus) type device 16, and a carrier 18 that in one exemplary embodiment takes the form of a wristband 18. The device 16 has many features similar to a USB flash drive, but has additional functionality as discussed in greater detail below. In addition, the device 16 is removably connected to the wristband 18.

As depicted in FIGS. 6-12, the wearable device 16 generally includes a housing 20 and a controller 21 that is contained by the housing 20. General components and functional capabilities of the controller 21 will be described in greater detail below. The housing 20 has a first end 22, a second end 24, a first side 26, a second side 28, a front side 30, and a back side 31.

As further shown in FIGS. 6-12, the first end 22 includes a connector 23 that is generally a standard USB connector having leads 81 or contacts embedded therein. The connector 23 is integrally molded with the housing 20 as described in greater detail below. The connector 23 is adapted to connect to a USB hub of a computer. The front side 30 has a pushbutton 33 that will cooperate with a first input 32 of the controller 21 for controlling the wearable device 16 as described in greater detail below. The first side 26 includes a side opening for accommodating second pushbutton 37 that cooperates with a second input 34 of the controller 21 for controlling the wearable device 16. The front side 30 also accommodates a display 36 of the controller 21. It is understood that the front side 30 of the housing 20 could have an opening wherein a screen of the display is positioned therein. It is also understood that the housing 20 could be formed such that it has a solid, thin layer wherein the display 36 of the controller 21 is viewable through the thin layer on the front side 30.

As depicted in FIGS. 6-12, the back side 31 of the housing 20, near the second end 24, has a protrusion 38. The protrusion 38 has a generally circular cross-section. The protrusion 38 has an enlarged rounded head and an insert that fits within the interior of the housing 20 (FIG. 12). As explained in greater detail below, the protrusion 38 is adapted to be inserted into a receiver or aperture 40 in the carrier 18. As further shown in FIG. 7, the device 16 has an overall curvature that provides an enhanced fit for a user wearing the device on the wrist. The curvature provides the connector 23 extending in a downward direction.

As further shown in FIGS. 6-12, the components of the controller 21 are contained within and supported by the housing 20. The controller 21 includes various electrical components allowing the controller 21 and device 16 to act as an interface device wherein the device 16 can communicate with the sensor 12, record and store data relating to athletic performance, other time information, as well as upload performance data to a remote location or site as described in greater detail below. The controller 21 further includes the first input 32 and the second input 34. The controller 21 further includes the display 36 that is positioned on the front side 30 of the housing 20. It is further understood that the controller 21 is operably connected to the connector 23 of the housing 20.

As shown in FIGS. 2-4 and 12-14, the carrier 18 is generally in the form of a wristband 18 having a central portion between a first end portion and a second end portion. The wristband 18 may include a first member 18a and second member 18b generally molded or connected together. The wristband 18 is flexible to fit around a user's wrist. In one exemplary embodiment, the wristband 18 may be injected molded of a flexible polymeric material. The wristband 18 has receiving structures for connection to the device 16. The carrier 18 includes a protective sleeve 60 proximate the central portion and having an opening 61 for receiving the connector 23 of the housing 20. The protective sleeve 60 has a generally contoured surface. As shown in FIG. 13, the sleeve 60 may have internal structure for assisting in securing the connector 23, such as ridges 63 that provide an interference type fit between the sleeve 60 and the connector 23. A recess 65 is also defined between the ridges 63 providing a gap between the connector 23 and a bottom portion of the sleeve 60. A vent 67 is provided through a bottom portion of the wristband 18 and is in communication with recess 65 proximate the connector 23 when inserted into the wristband 18. The vent 67 allows any moisture to escape from the wristband 18 and be channeled away from the connector 23. Also at the central portion, the carrier 18 has an aperture 40 dimensioned to receive the protrusion 38 of the wearable device 16. As further shown in FIGS. 3 and 4, the first end portion has a pair of holes 17 (FIG. 13) to accommodate a removable closure as described in greater detail below. The second end portion has a plurality of holes 19 to cooperate with the removable closure as further described below for securing the wristband 18 to a wrist of a user (FIG. 2).

As further shown in FIGS. 4 and 13-16, the wristband 18 has a removable closure 70 used to fasten the wristband 18 to a wrist of a user. To this end, the removable closure 70 cooperates with the plurality of holes in the wristband 18. The removable closure 70 has a plate member 72 and a plurality of posts 74 extending generally in a perpendicular direction from the plate member 72. In the exemplary embodiment depicted in FIG. 15, the plate member 72 has two posts 74. Each post 74 has an insert 76 that is pressed on or snap-fitted onto the post 74. Each insert 76 may be spot welded to the plate member 72. Each insert 76 may be rounded in order to provide a comfortable fit against a user's wrist. Other connection methods are possible. A gap is maintained between an inside surface of the plate member 72 and a bottom surface of the post 74. In addition, each post 74 has an annular channel 78 around a periphery of the post 74.

To wear the wristband, first the removable closure 70 is connected to the first end portion of the wristband strap 18 wherein the pair of holes 17 is provided to receive the posts 74. The wristband 18 fills the gap. It is further understood that the recessed area 71 in the wristband 18 is dimensioned according to the size of the plate member 72 wherein the plate member 72 fits snugly within the recessed area 71. The wristband 18 is positioned around the user's wrist and the posts 74 are inserted into the holes 19 provided on the second end portion of the wristband 18 as can be appreciated from FIG. 2. The portion of the wristband 18 proximate the holes 19 fits within the annular channels 78 of the posts 74. After the posts 74 are inserted into the pair of holes 17 of the first end portion of the wristband 18 and the plurality of holes 19 of the second end portion of the wristband 18, the first end portion and second end portion of the wristband overlap one another. With the use of a pair of posts 74, the removable closure 70 allows for a secure connection and greater flexibility in connection providing for a greater adjustment to accommodate for a range of wrist sizes.

Additionally, the plate member 72 can have indicia 73 thereon. The plate member 72, when attached to the wristband 18 faces away from the wristband 18 wherein the indicia 73 can be viewed by others. Because the removable closure 70 is easily removable, the closure 70 can be used as a memento, different closures can be provided and used with the wristband 18. Thus, removable closures 70 having different indicia can be provided and used as a keepsake, memento, or a reward for accomplishing a goal, participating in a race, or otherwise achieving a certain level of fitness. Indicia can take various forms including wording, graphics, color schemes, textures, or other designs etc.

As discussed, the wearable device 16 is removably connected to the carrier 18. The connector 23 is inserted into the sleeve 60 of the carrier 18, and the protrusion 38 is placed into the aperture 40 of the carrier 18. The protrusion 38 may extend perpendicularly from the central portion of the carrier 18. The enlarged head of the protrusion abuts against the wristband 18 to retain the device 16 onto the wristband 18. This provides for a wearable device 16 that can be disconnected from the carrier 18 when desired and plugged into a computer as discussed in greater detail below. It is understood that detent structures can be provided between the connector 23 and sleeve 60 of the various different embodiments disclosed herein.

It is understood that the device 16 has general functions such as keeping the time of day just like a conventional watch device. It is further understood, however, that the device 16 has athletic functionality and can be used as part of the athletic performance monitoring system 10. For example, a user wearing shoes having the sensor 12 mounted therein can use the device 16 to wirelessly communicate with the sensor 12 and monitor performance such as for running.

Figure 18:
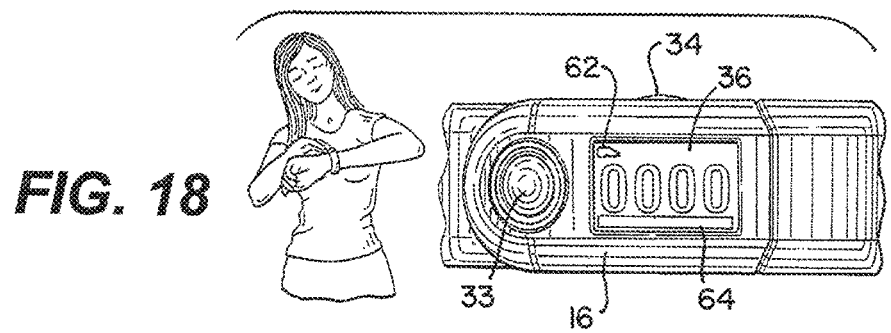
FIG. 18 is a schematic view of the runner setting the device and a plan view of the device indicating that the device is ready to start according to one or more aspects described herein.
Figure 19:
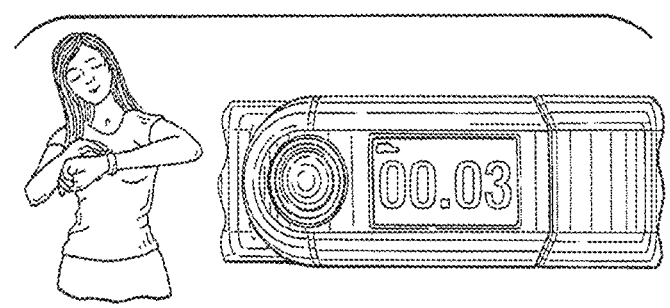
FIG. 19 is a schematic view of the runner starting the device and a plan view of the device indicating time elapsed according to one or more aspects described herein.
Figure 20:
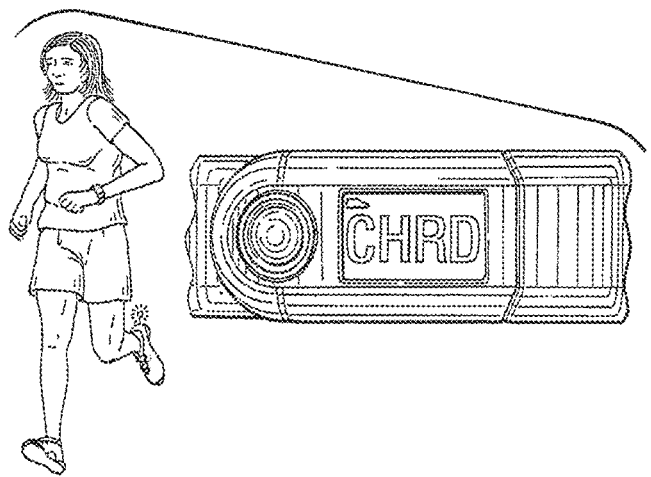
FIG. 20 is a schematic view of the runner and plan view of the device indicating the device is in a data recording mode according to one or more aspects described herein.
Figure 21:
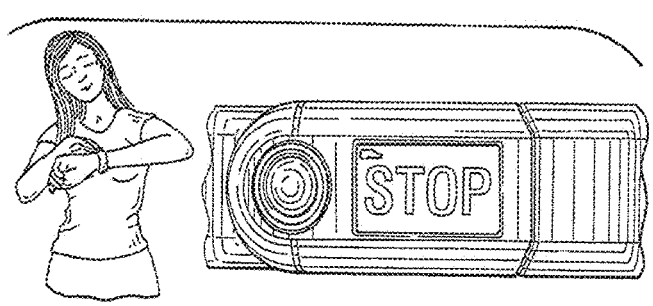
FIG. 21 is a schematic view of the runner stopping the device and a plan view of the device indicating that the device has been stopped according to one or more aspects described herein.
Figure 22:
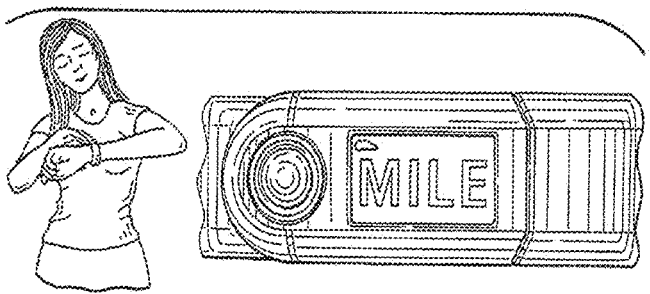
FIG. 22 is a schematic view of the runner reviewing performance data and a plan view of the device preparing to indicate miles run according to one or more aspects described herein.
Figure 23:
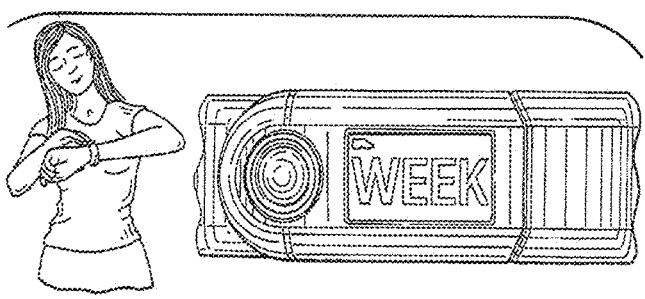
FIG. 23 is a schematic view of the runner reviewing performance data and a plan view of the device preparing to indicate miles run in a week according to one or more aspects described herein.
Figure 24:
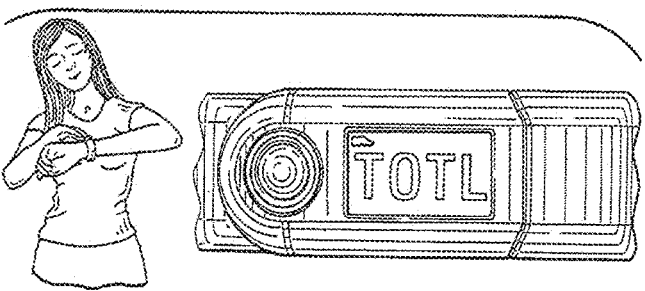
FIG. 24 is a schematic view of the runner reviewing performance data and a plan view of the device preparing to indicate total miles run according to one or more aspects described herein.
Figure 25:
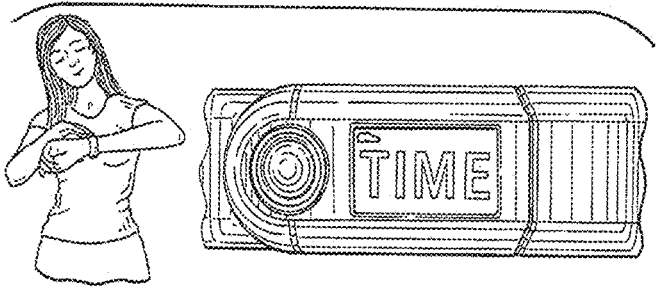
FIG. 25 is a schematic view of the runner reviewing performance data and a plan view of the device preparing to indicate time according to one or more aspects described herein.

As can be appreciated from FIGS. 17-27, when the user wants to start a run, the user must first allow the sensor 12 to communicate with the wearable device 16. It is understood that the device 16 may first be calibrated for the user. To start a run, the user pushes and holds the first input 32 via the pushbutton 33 on the front side 30 of the housing 20. While the user holds the first input 32, the display 36 exhibits scrolling zeros as the wearable device 16 searches for the sensor 12. Once the sensor 12 is located, as shown in FIG. 18, the display 36 indicates that the wearable device 16 is ready to start by displaying a shoe symbol 62 in the upper left corner and a blinking underline 64. The user then pushes the first input 32 again to initiate the recording of the run. The wearable device 16 then records various information during the run such as elapsed time as shown in FIGS. 19 and 20. A bottom line on the display 36 animates back and forth to indicate that the device 16 is in the record mode. During the run, the user can toggle through the distance run, current pace, elapsed time, and calories spent by pushing the second input 34 via second pushbutton 37. To stop recording, the user pushes the first input 32. After the device 16 is stopped, the user can review the last distance run (FIG. 22), average pace, calories burned, average calories burnt per minute, miles ran per week (FIG. 23), total miles (FIG. 24), and the time of day of the run (FIG. 25) by pressing the second input 34, which toggles through these values.

Figure 26:
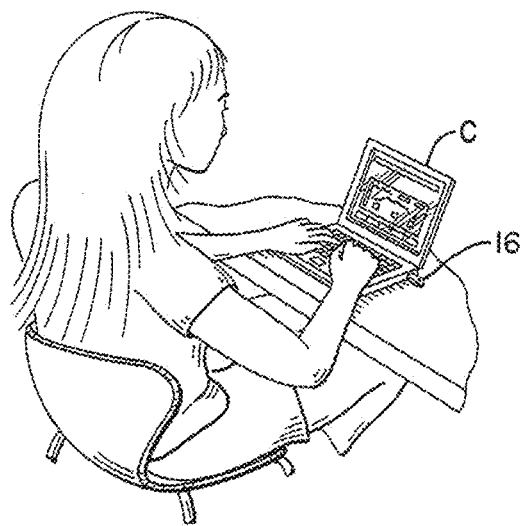
FIG. 26 is a perspective view of the runner at a computer and having the device plugged into the computer according to one or more aspects described herein.
Figure 27:
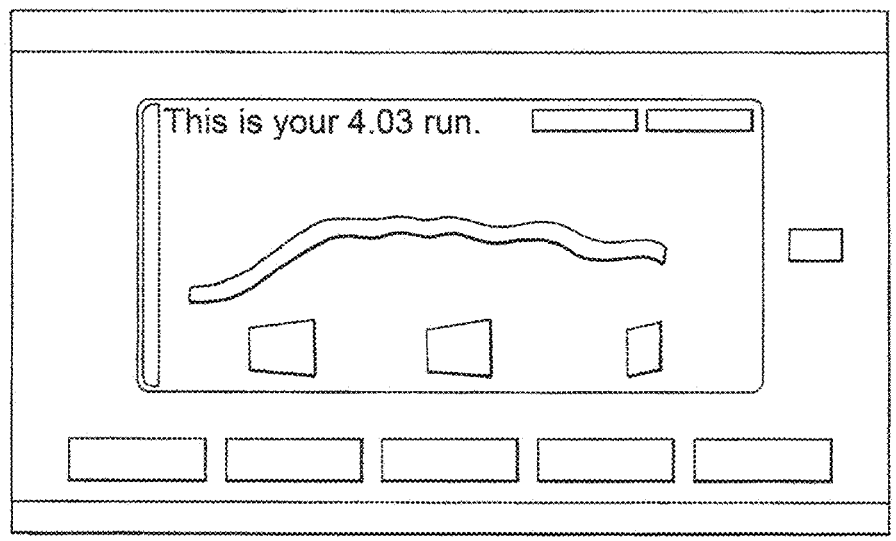
FIG. 27 is a front view of a computer screen displaying performance data recorded by the device according to one or more aspects described herein.
Figure 31:
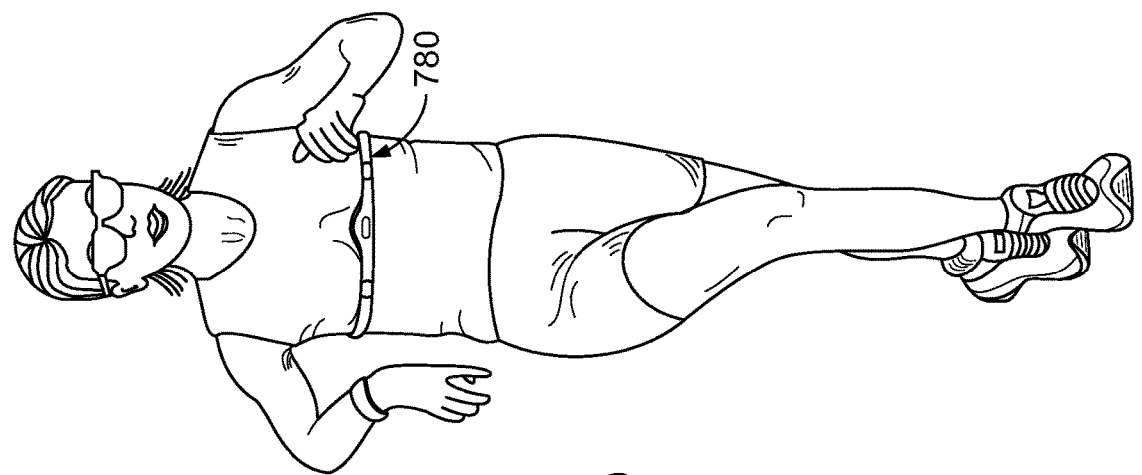
FIG. 31 is a is a front view of a user with the heart rate monitor assembly of FIG. 29 according to one or more aspects described herein.

The device 16 has additional capability for uploading of the recorded data to other remote locations such as locally on a personal computer or a remote website for further display, review and monitoring. To this end, it is understood that the controller 21 of the device has an appropriate user interface wherein a user can download appropriate software via a computer from a remote location. The device 16 is removed from the carrier 18 wherein the protrusion 38 is removed from the aperture 40 and the connector 23 is removed from the sleeve 60. As shown in FIGS. 26 and 27, the connector 23 is then plugged into the standard USB hub/port on a computer C. Once the appropriate software is installed, the application will commence with device 16 still being plugged into the computer. The software application may prompt the user through a device set-up procedure (time, calibration etc.). At this point, if desired, the user can upload the performance data from the run to a remote website location such as one dedicated to monitoring athletic performance. The user can log onto the particular website via a standard web-browser and upload the performance data from the device 16 to the website. As shown in FIG. 27, the user can then review data relating to the run. The website may display the data in graphical form. Other features can also be provided to assist the user in utilizing the data recorded by the device. Additional registration features can be provided with the website wherein additional features can be provided to the user for use with the device 16.

The user interface associated with the controller 21 of the device 16 can provide additional functionality to the user. The software can include a self launching feature, which automatically launches the software once the wearable device 16 is connected to a computer containing the software. Once the program is launched, the software will also automatically download the data from the device 16 to the computer and transfer the data to a web server and to the website discussed above. The software can also detect the device class connected to the port and configure the correct application for that specific device. For example, there may be wearable devices 16 having different configurations, or technical capabilities, and thus may be classified differently. The software can change the feature set of the fitness activity recording of the wearable device 16 connected to the port of the computer. After the wearable device 16 is disconnected from the computer, the software automatically exits. The user interface may also be configured to allow a user to selectively activate and de-activate features according to the preferences of the user. The user may also be able to modify software associated with the device.

The software has an extremely simple calibration method and user interface. For example, it is very simple to calibrate distance measurements onto the device. The software can also track motivational information among several classes of fitness activity recording devices. For example, the user can set weekly goals and the software can track the user's progress with these goals. The user can also use multiple devices, such as an audio player having a suitable interface device, other types of sport watches etc., along with the device of the present invention, and the software will accumulate the weekly and overall total distance recorded by all of the devices. Thus, the data is kept synchronized over multiple devices.

The website can additionally have a guest log in, which allows the user to upload data automatically from the device without requiring the user to register. This feature allows the user to use the website without giving personal information. Later, if the user decides to register the device, a unique PIN number associated with each wearable device is matched up with registration information automatically.

According to one or more arrangements, a sensor configured to communicate data to a wearable device assembly (e.g., assembly 14 of FIG. 1) may be used to monitor a user's heart rate. For example, a sensor may be used to determine a user's heart rate (beats per minute) during performance of an athletic activity such as running, using an elliptical, walking and the like. FIGS. 28-31 illustrate a removable closure for a heart rate monitor assembly 780. The heart rate monitor assembly 780 has a chest strap 718 and a transmitter portion 782. The chest strap 718 has a first end 720 and a second end 722, while the transmitter portion 782 also has a first end 724 and a second end 726. The transmitter portion 782 has at least two removable closures 770 which are used to fasten the chest strap 781 to the transmitter portion 782. The removable closure 770 is generally similar in structure to the removable closure 70 described above and shown in FIGS. 4 and 15. One removable closure 770 is attached to the first end 724 of the transmitter portion 782 and one removable closure 770 is attached to the second end 726 of the transmitter portion 782. To this end, the removable closures 770 cooperate with a plurality of holes on the first end 720 and the second end 722 of the chest strap 781.

As discussed, the removable closure 770 used with the heart rate monitor assembly may be very similar to the removable closure 70 as depicted in FIGS. 4 and 15. The removable closure 770 may have a plate member 72 and a plurality of posts 74 extending generally in a perpendicular direction from the plate member 72. As is depicted in FIGS. 15, 16, the plate member 72 has two posts 74. Each post 74 has an insert 76 that is pressed on or snap fitted onto the post 74. Each insert 76 is spot welded to the plate member 72. Other connection methods are possible. A gap is maintained between an inside surface of the plate member 72 and a bottom surface of the post 74. In addition, each post 74 has an annular channel 78 around a periphery of the post 74.

Figure 30:
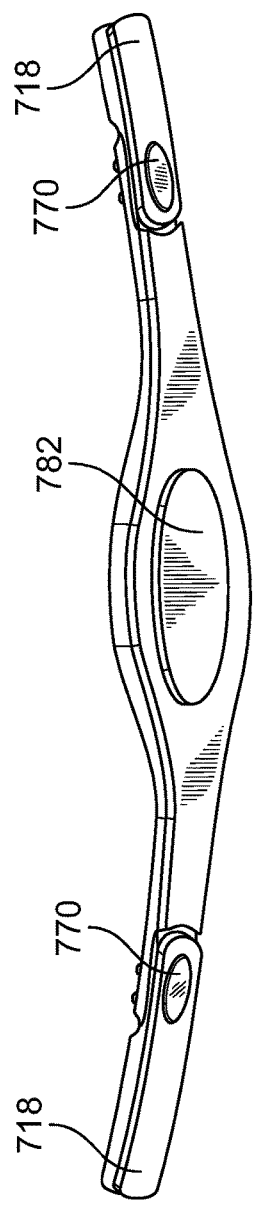
FIG. 30 is a partial perspective view of the heart rate monitor assembly of FIG. 29.

To wear the heart rate monitor assembly 780, as depicted in FIG. 30, first the first removable closure 770 is connected to the first end 724 of the transmitter portion 782 wherein a pair of holes is provided to receive the posts 74. Next, the first removable closure 770 is connected to the first end 720 of the chest strap 781 by inserting the posts 74 into the holes provided on the first end 720 of the chest strap 781. The chest strap 781 is then positioned around the user's chest. Next, in order to fasten the heart rate monitor assembly 780 around the user's chest, the second removable closure 770 is connected to the second end 726 of the transmitter portion 782 wherein a pair of holes is provided to receive the posts 74. Next, the second removable closure 770 is connected to the second end 722 of the chest strap 781 by inserting the posts 74 into the holes provided on the second end 722 of the chest strap 781. With the use of the pair of posts 74, the removable closure 770 allows for a secure connection and greater flexibility in connection providing for a greater adjustment to accommodate for a range of chest sizes.

As discussed earlier, the plate member 72 of the removable closure 770 can have indicia 73 thereon. The plate member 72, when attached to the chest strap 781 and transmitter portion 782, faces away from the chest strap 781, wherein the indicia 73 can be viewed by others. Because the removable closure 770 is easily removable, the closure 770 can be used as a memento and different closures can be provided and used with the heart rate monitor assembly 780. Thus, removable closures having different indicia can be provided and used as a keepsake, memento, or reward for accomplishing a goal, participating in a race, or otherwise achieving a certain level of fitness. Indicia can take various forms including wording, graphics, color schemes, textures, or other designs, etc. Also, as a pair of removable closures 770 is utilized in one exemplary embodiment, the indicia included on each removable closure 770 can provide for an overall unitary message as desired.

Heart rate monitor assembly 780, in one or more configurations, may be operably connected to a monitoring device assembly such as assembly 14 and wearable device 16 (FIG. 1) and/or one or more other sensors such as shoe-based sensor 12 (FIG. 1). For example, heart rate monitor assembly 780 may be configured to wirelessly communicate with wearable device 16 to communicate heart rate data. According to one or more aspects, heart rate monitor assembly 780 may receive data from shoe sensor 12 (FIG. 1) and forward the information to another device like wearable device 16 (FIG. 1). Alternatively or additionally, heart rate monitor assembly 780 may be configured to store and/or display athletic performance data including heart rate information and data determined by sensor 12 (FIG. 1).

Figure 32:
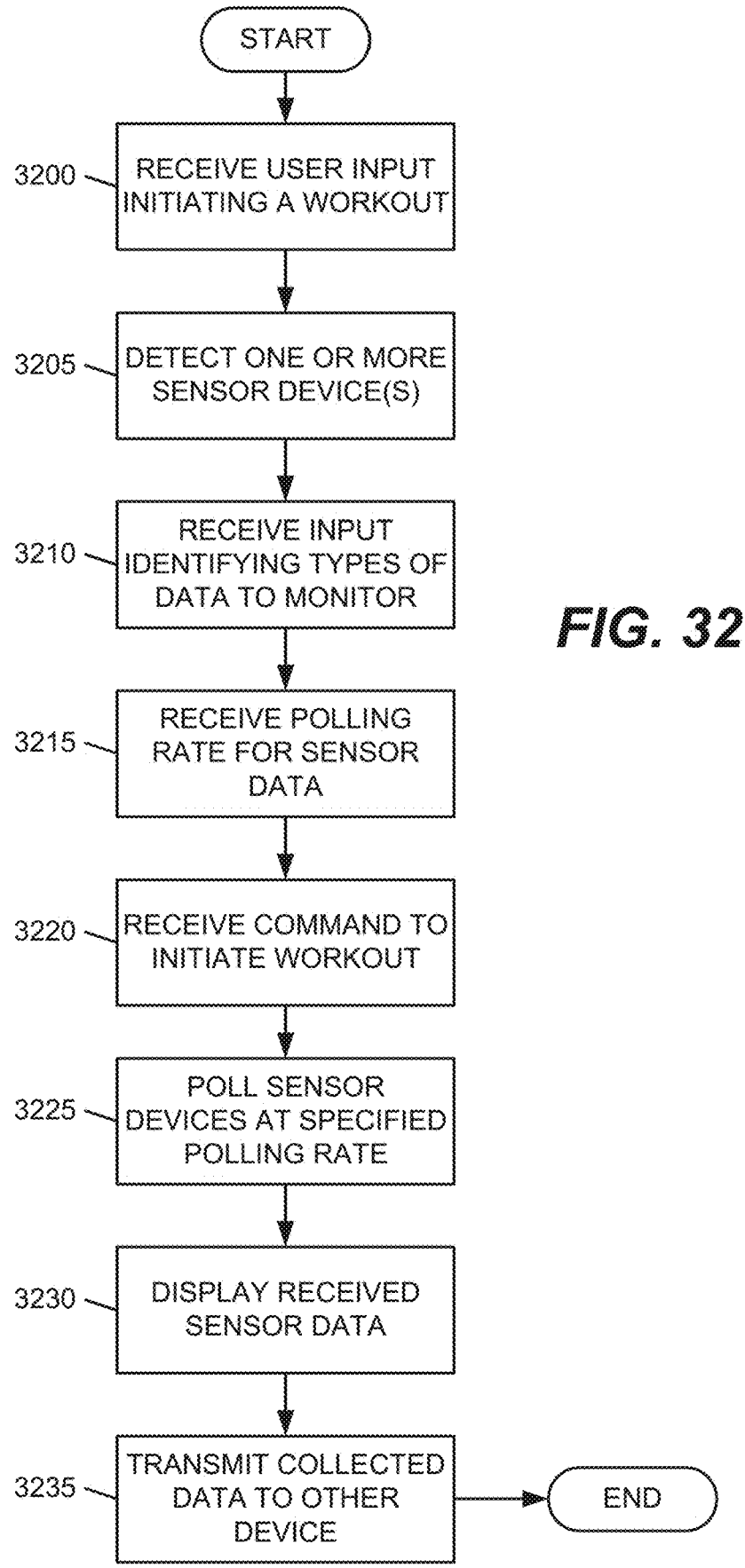
FIG. 32 is a flowchart illustrating a method by which an athletic performance monitoring device may collect athletic performance data from one or more sensors according to one or more aspects described herein.

FIG. 32 illustrates a method by which an athletic performance monitoring device such as wearable device 16 of FIG. 1 may monitor athletic performance of an athlete by collecting athletic performance data from one or more sensors. In step 3200, the monitoring device may receive user input initiating a workout. The user input may include a selection of a type of activity (e.g., running, walking) and a duration. The user input may further include a selection of a music playlist to use during the workout. In step 3205, the device may detect sensor devices that are compatible with the device. For example, the device may detect whether one or more registered BLUETOOTH, infrared and/or WI-FI sensors are within range and determine a type of data (e.g., heart rate, speed, steps, etc.) provided by the sensors. In step 3210, the monitoring device may receive input corresponding to a selection of one or more types of performance data to monitor. For example, a user may ask that heart rate information be monitored but not pace. In another example, a user may request monitoring of both heart rate and pace information. In yet another example, a user may specify that only pace information is to be monitored. In still another example, a user may request that only heart rate be monitored. In some instances, different selections of performance data types may be made for different actions. Thus, a user may select a first set of one or more performance data types for a first action while selecting another set of one or more performance data types for a second action. For example, a user may select pace and heart rate for storage but only heart rate for display. In another example, a user may select pace and heart rate for recording/storage but only heart rate or only pace or both for uploading to a remote athletic activity monitoring site. Accordingly, upon initiating an upload from a monitoring device to a remote performance monitoring site/server, the device or system may determine whether each of the stored types of performance data was selected for uploading. In some instances, the system or device might only upload those types of performance data that were selected for uploading.

Selections may be made from a menu that displays the types of athletic performance data that may be monitored. This menu may be generated based on the detected sensors that are available. In step 3215, the monitoring device may receive configuration information for a rate at which to poll for the requested sensor data. The rate may be specified per second, per minute, per hour and the like. In one or more arrangements, the rate for a first sensor (e.g., heart rate) may be different from a rate for a second sensor (e.g., a pedometer). In step 3220, the device may receive a command to initiate the workout. In response, the device may subsequently begin polling the various sensor devices for the athletic performance data at the specified rates in step 3225.

The collected athletic performance data may be displayed as it is received in step 3230 so that a user may monitor his or her performance during the workout. Additionally or alternatively, the device may transmit the performance data to another device such as a personal computer after the workout in step 3235. For example, a user may connect the wearable device using wired or wireless adapters to transmit the data.

Athletic performance data may be displayed to a user as part of an athletic performance visualization. For example, data regarding the user's pace and heart rate during a run may be used to generate a graph to show a user's trend during the activity. The visualization might only display information that was selected for uploading or for visualization. For example, as noted above, users may select different performance data types for different purposes. Accordingly, a user may select to record pace, heart rate, time and distance, but select only heart rate and time for visualization. The determination of what information types to upload and/or use in a visualization may be made by the wearable monitoring device, a user's computing device and/or a remote performance monitoring system.

By using a heart rate monitor and allowing users to visualize athletic performance as a function of heart rate in addition to or instead of metrics that are specific to one or more athletic activities (e.g., distance, pace, etc.), a user may monitor and track virtually all forms of athletic activity. Accordingly, users may track and monitor activities such as yoga, lifting weights, aerobics, and the like using heart rate as a metric. Heart rate monitors, as discussed herein, may be used with a plurality of monitoring systems and devices and may independently store and/or upload data to a remote athletic performance monitoring site and/or system. For example, heart rate monitors may include an integrated wireless communication system.

Visualizations and workout information processing may be performed in one or more arrangements by a third party athletic performance data collection and tracking system. For example, upon an athletic performance monitoring device capturing the performance data, the device may upload the performance data to a collection and tracking system. The collection and tracking system may reside on a remote server and be accessible to a variety of users. In one configuration, the collection and tracking system may comprise a network server operating a web site through which users may upload athletic performance data, analyze their workouts, compare their workout performance with other users, share their workout data and the like. In some arrangements, users may also select whether a particular workout session, day of workout session or other predefined period of workouts are to be visualized, stored, uploaded and the like. For example, before beginning a run, a user may indicate whether the workout is to be uploaded, stored and/or used in visualization. In other examples, the user may make such elections or selections during a workout or after the workout. Thus, if a user does not believe the current run is representative of a good effort, the user may modify the uploading, visualization or recordation options for one or more sensed parameters (e.g., heart rate, pace, distance, etc.). Again, visualization, uploading and recordation for each sensed parameter may be modified and set separately from the others.

Figure 33:
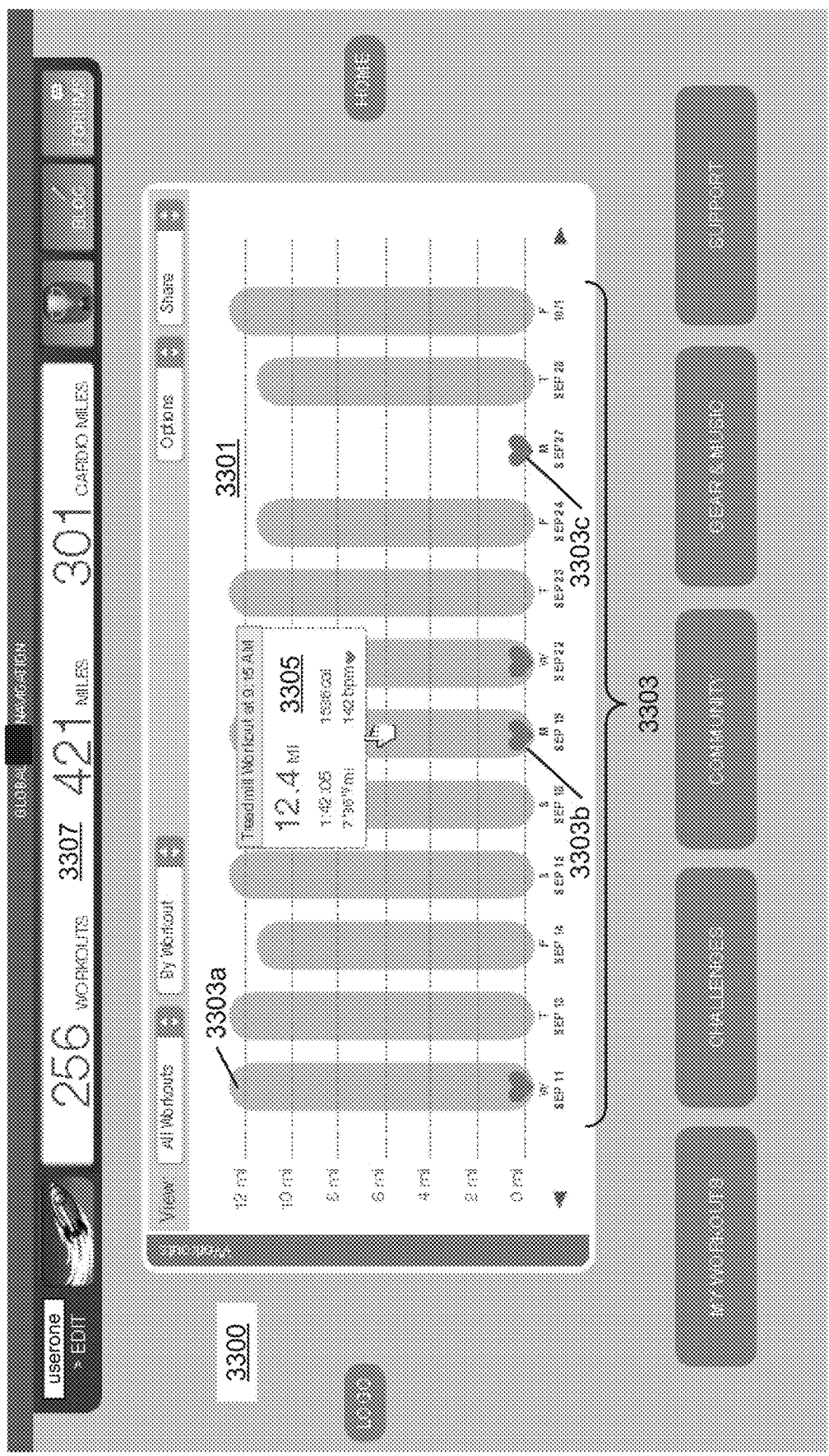
FIGS. 33-35 illustrate example user interfaces in which a user's workout information including heart rate information is visualized as a distance over time graph according to one or more aspects described herein.

FIG. 33 illustrates an example user interface 3300 in which athletic performance data may be visualized and reviewed. Each workout or day of workout may be represented by entries 3303. A workout entry may include a single workout or may include all workouts for a predefined time period (e.g., a day). Thus, user interface 3300 may display multiple workout entries 3303 simultaneously in, for example, a bar graph. That is, each bar 3303 may represent a different workout or day of workouts or other predefined time period of workout sessions. The appearance of entries 3303 may vary depending on the types of data recorded for that workout or day or workout. For example, entry 3303*a* may be represented by a bar with a heart to indicate that both run data (e.g., pace or distance information) and heart rate information was recorded for that workout. In another example, entry 3303*b* might include a bar with no heart, indicating that run/pace information is available for the workout while heart rate information is not. In yet another example, entry 3303*c* may include a heart with no bar to indicate that heart rate information is available but that distance/pace information was not record or not uploaded to the system. Alternatively, if heart rate information is available or was recorded, the heart may be displayed upon a user hovering over the corresponding workout entry (e.g., workout entry 3303*b*) instead of the heart or other icon being persistent in the display. Once a user is no longer hovering over or otherwise interacting with the workout entry, the heart may disappear or be removed. Other types of indicators may be used including different fill colors for the bars, different fill patterns, different transparencies and the like.

In some arrangements, indicators may also be used to identify the type of activity corresponding to the athletic activity data. Accordingly, a basketball icon may be displayed in a bar or other portion of the graph to indicate the user was playing basketball while a pool icon may be displayed for swimming activities. By tracking the type of activity contributing to the athletic activity data, different types of coaching and/or thresholds may be used in judging the user's performance. In one particular example, a color of the athletic activity bar or segment of a line graph may be selected based on how well the user performed. For example, if a user exceeded a first distance or pace threshold for a running activity, the corresponding bar or portion of a line graph may be displayed in a first appearance (e.g., green), while if the user was below another threshold, the corresponding bar or portion of a line graph may be displayed in a second appearance (e.g., yellow or red). The various thresholds may be selected based on the indicated type of activity. Thus, different activities (e.g., weight lifting, basketball, swimming, running, soccer, etc.) may have different thresholds (e.g., heart rate, pace, distance, etc.). For example, heart rates during weight lifting may be generally lower than heart rates during running or basketball. Accordingly, lower heart rate thresholds may be set for weight lifting than for running or basketball. Thus, the indication (e.g., visualization using color or patterns of the data representations) of whether the user is excelling or underachieving may be relative to the particular activity.

According to one or more aspects, the user may filter the visualization based on type of workout. For example, the user may filter the visualization down to heart rate workouts (irrespective of whether run data is available), heart rate-only workouts, run workouts (irrespective of whether heart rate data was recorded), run-only workouts, run and heart rate workouts and the like.

Hovering over one or more of entries 3303 may also cause the interface to generate and display a pop-up window 3305 with detailed workout information. The workout information displayed in window 3305 may include a time of the workout, a type of workout, a machine used during the workout, a total distance, a duration, a pace (e.g., minutes/mile, miles/hour, etc.), an average heart rate, a number of calories burned and the like. User interface 3300 may further include a workout summary bar 3307 that is configured to display a total number of workouts, a total distance, and/or a total number of calories burned or an equivalent thereof for a specified period of time. In one or more arrangements, the specified period of time may correspond to the time period shown or may correspond to a time period encompassing all workouts stored. Additionally or alternatively, a calories burned equivalent may include cardiovascular miles which may be defined as a unit equaling 100 calories burned. Thus, 3,000 calories burned may be equivalent to and converted into 30 cardiovascular miles. This unit may be used to provide a universal basis of comparison between different types of activities such as swimming and weightlifting, running and yoga and the like. Bars in a bar graph that represent cardiovascular miles versus calories burned may appear differently.

FIG. 33 illustrates an example cardiovascular mile bar graph 3301 (with and without heart rate information) and example mile bars 3303 (with and without heart rate information). According to one or more aspects, hovering over different parts of the graph may display different additional details of the workout. For example, if a user hovers over or otherwise interacts with heart displayed in bar 3303b, additional details relating to the user's heart rate or cardiovascular performance such as a range of heart rates detected, a max and min heart rate, average heart rate and the like may be displayed in pop-up window (similar to window 3305). In another example, a user hovering over only the bar graph portion (without hovering over the heart indicator of bar 3303b) may cause pop-up window 3305 to display more run related metrics including distance, pace and/or time.

Figure 34:
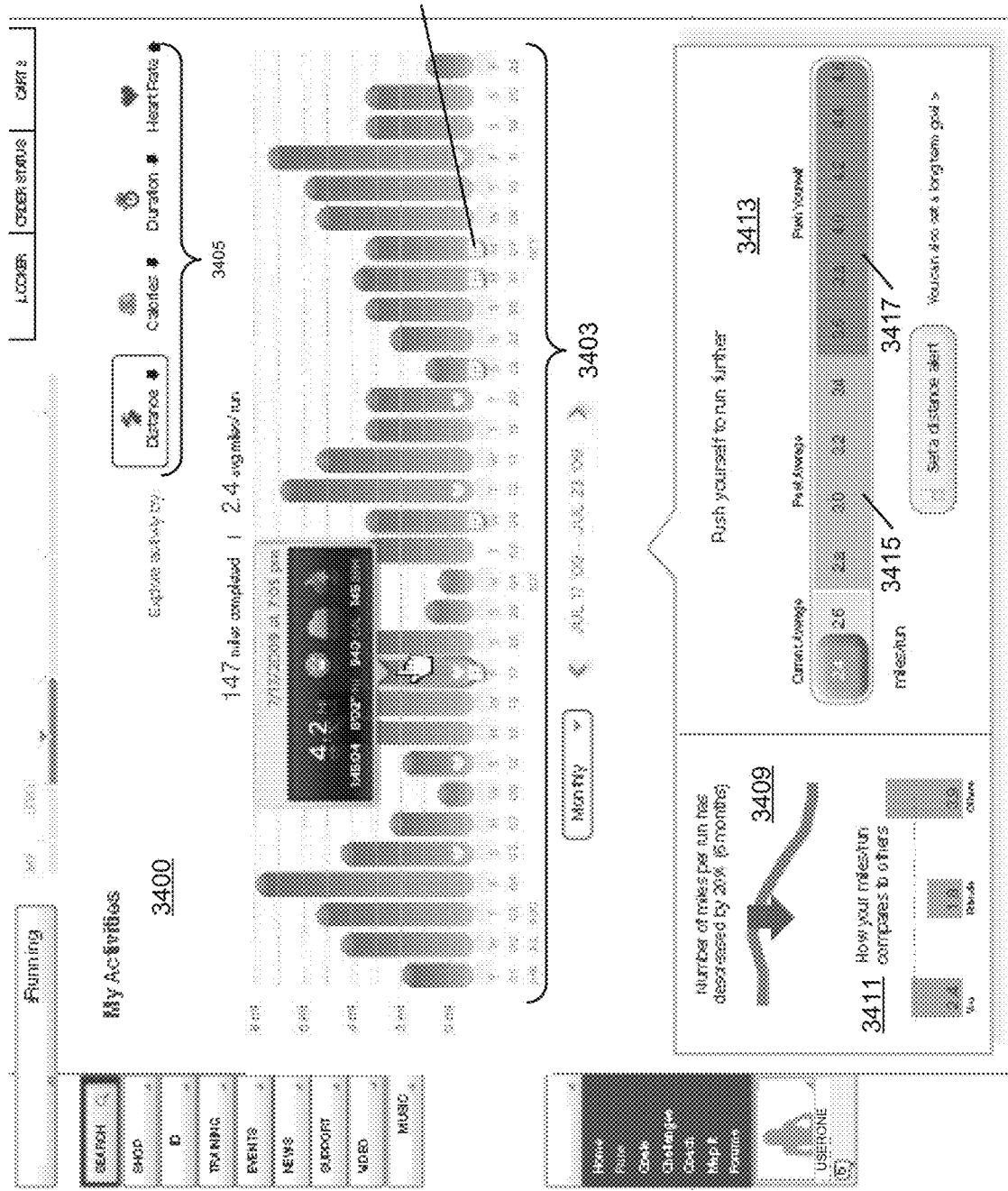
Figure 35:

FIGS. 34 and 35 illustrate alternative embodiments of a user interface for displaying workout entries. In addition to entries 3403, interface 3400 of FIG. 34 may include an option bar 3405 for changing the graph or display type. That is, option bar 3405 may allow a user to switch between a graph of time vs. distance, time vs. calories, time vs. duration and time vs. heart rate. Furthermore, interface 3400 may include a note indicator 3407 that identifies entries for which a comment is associated. Hovering over or otherwise interacting with indicator 3407 (e.g., clicking) may cause interface 3400 to display the comment or note. The user may enter notes to record a workout regimen for that day, how the user felt during the workout, information about a running path, athletic equipment used during the workout and the like.

Interface 3400 may further display trend information that allows a user to determine a degree of progression or regression in their performance over a specified amount of time. For example, trend information 3409 indicates that the user's number of miles run has decreased by 20% in the past 6 months. The trend information may be calculated or determined based on a predefined time period set by the user. For example, the user may configure the interface 3400 to display the user's performance trend for a previous year, the past week, past 2 weeks, past month, past 3 months and the like. Trend information 3409 may also be configured to identify trends for different types of performance information such as pace and heart rate. Furthermore, interface 3400 may display a comparison 3411 of performance data that shows the user's activity as compared to others including friends and the general public. This information may be retrieved from a database or requested from devices associated with each of the other users.

Users may choose to set a goal for increasing an aspect of their athletic performance, such as pace, by setting an alert using goal setting tool 3413. Tool 3413 allows a user to set a goal and to alert themselves (e.g., through an athletic monitoring device) when the set goal is reached. For example, the goal may correspond to an average number of miles run per workout or over a predefined period of time. Thus, if a user is currently running about 2 miles per workout, the user may set a goal and alert for running 2.5 miles per workout. Upon reaching the goal, the user may receive a notification such as a text message, an e-mail, a message on an athletic performance monitoring device and the like. Interface 3400 may automatically identify zones of improvement that may be considered to require moderate additional effort (e.g., past average zone 3415) or significant additional effort (e.g., push yourself zone 3417). In one example, workout data may be automatically uploaded to the performance monitoring site and system during or after a user's workout. Accordingly, a user might not always check the site to review the workout session in relation to preset goals or past activities. Thus, the performance monitoring site may transmit a text message or email or automated voice call in order to alert the user of the achievement. In some arrangements, the performance monitoring site might also post a message on a user's social networking site or issue a broadcast message through services such as TWITTER.

In FIG. 35, interface 3500 may display information and features similar to those described with respect to interface 3400 of FIG. 34. Interface 3500 may further include a reminder tool 3503 that allows users to add a reminder for performing an athletic activity such as running a specified number of times per week (or other time period). Users may also adjust what the main component of the graph (e.g., the bars) represents. For example, a user may wish to view calories as the bars in the graph or heart rate. In such instances, other types of indicators (not shown) may be used to indicate whether the other metrics were recorded and stored for those workouts. For example, a road icon may be displayed with one or more bars to indicate that distance information is available for that workout. Calories may be represented by a food item while duration may be represented by a clock.

Figure 36:
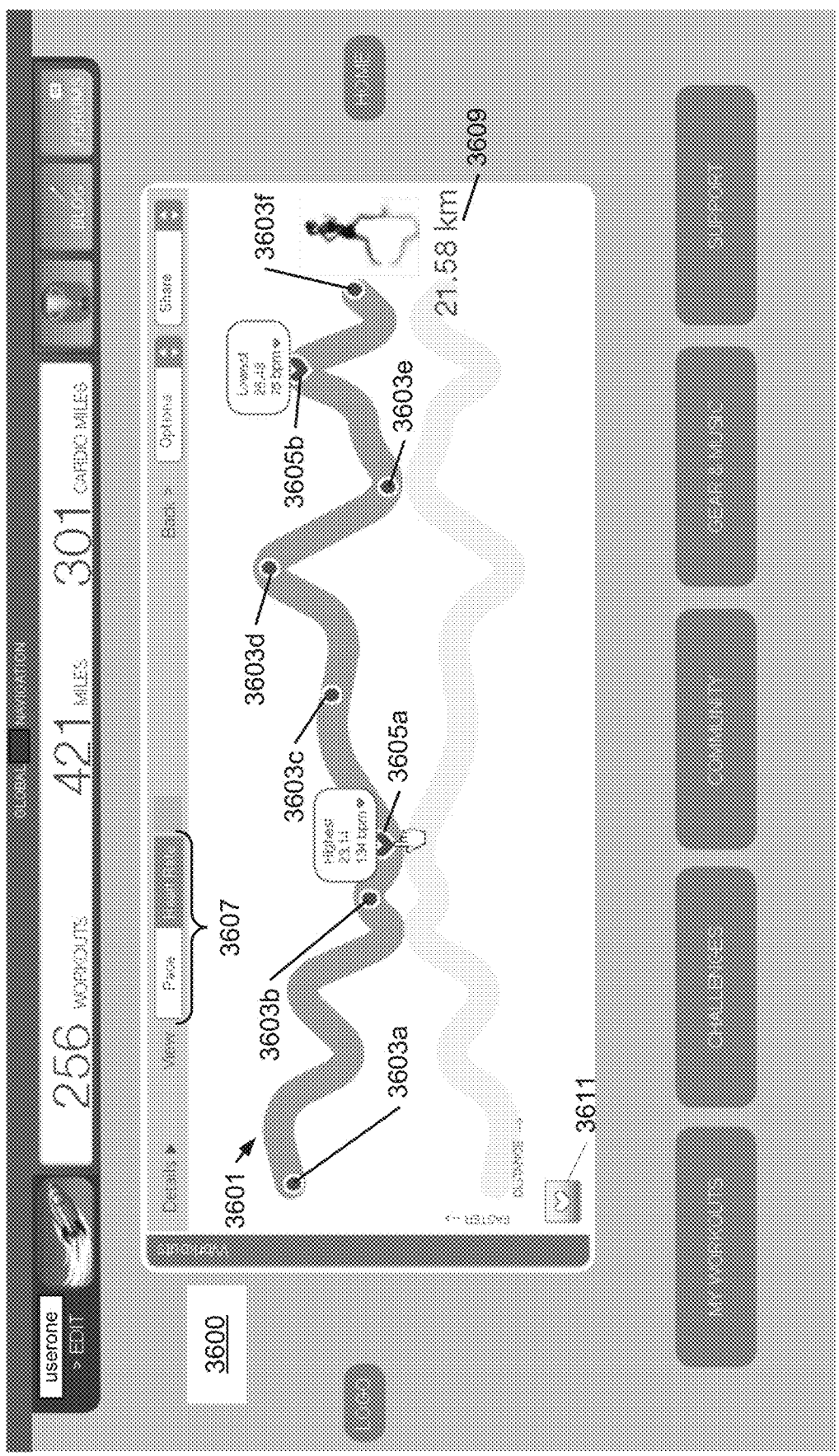
FIGS. 36 and 37 illustrate example user interfaces in which a user's pace during a workout is visualized in conjunction with heart rate information according to one or more aspects described herein according to one or more aspects described herein.
Figure 37:
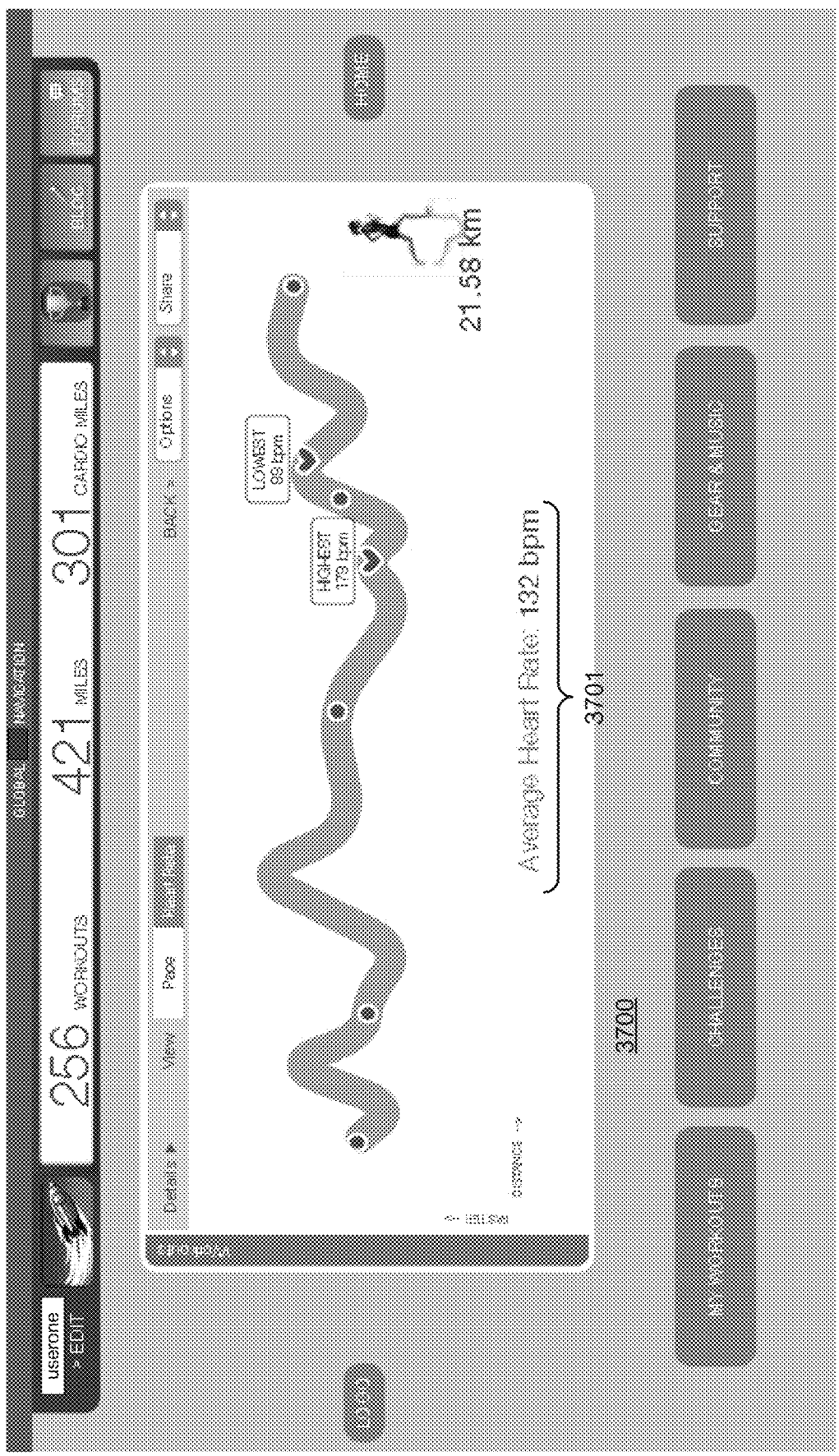

FIGS. 36 and 37 illustrate user interfaces in which a user's workout is displayed as a graph of pace over distance. Graph 3601 of FIG. 36 includes multiple indicators 3603 identifying predefined times or distances of the workout. For example, indicators 3603 may correspond to mile markers or hourly markers. Alternatively or additionally, markers 3603 may be used to identify an amount of progress toward a goal. Thus, markers 3603 may be placed at positions on graph 3601 that correspond to 0%, 25%, 50%, 75% and 100% of the goal distance. Furthermore, graph 3601 may include heart rate markers 3605 that identify the points in the workout where an athlete reached his or her highest and lowest heart rates. For example, marker 3605a may correspond to the athlete's highest heart rate during the workout and marker 3605b may correspond to the athlete's lowest heart rate. Additional heart rate markers may also be included in graph 3601 depending on the preferences of the user. In one or more arrangements, the highest and lowest heart rates might only be selected from a portion of a workout after a warm-up period or other predefined amount of initial workout time. For example, interface 3600 might only identify the highest and lowest heart rates after the first 30 seconds, 1 minute, 3 minutes, 5 minutes of the workout. Alternatively or additionally, interface 3600 might ignore a predefined amount of time at the end of the workout. Ignoring these portions of the workout in determining highest and lowest heart rates may help eliminate artificially low or high heart rates due to cool down, initial warm-up and the like. According to one or more aspects, the highest and lowest heart rates may be determined by identifying the highest and lowest average heart rates, respectively, for a predefined period of time (e.g., 5 seconds, 10 seconds, 15 seconds, 20 seconds, 30 seconds, etc.). In one example, the determined heart rate for time 1 minute and 30 seconds may correspond to an average of the heart rates between 1 minute and 20 seconds and 1 minute and 40 seconds. Hovering over each of markers 3603 and 3605 may provide detailed information similar to the detailed information displayed in window 3305 of FIG. 33. Alternatively or additionally, detailed information may be displayed in a pop-up window for one or more markers 3603 and 3605 without having to hover over or otherwise interact with marker 3603 and/or 3605. Hovering or otherwise interacting with other portions of graph 3601 may also provide additional information about a particular portion of graph 3601. According to one or more aspects, a user may set low and high thresholds for his or her heart rate. Accordingly, indicators 3605a and 3605b may correspond to the points in the workouts where the user crossed above or below those thresholds. For example, a user may set a high heart rate threshold at 150 bpm. Accordingly, graph 3601 may display heart 3605b at the point where the user first crosses the 150 bpm threshold. An indicator such as heart 3605b may be displayed at each point along graph 3601 where the user crossed above or met the threshold. Similarly, an indicator may be displayed along graph 3601 where a user crossed below or met a lower or minimum threshold to help the user recognize where he or she exhibited a weaker performance in terms of heart rate.

View option 3607 allows a user to switch between the different types of graphs. For example, upon selecting heart rate in option 3607, the graph may instead display distance vs. heart rate (rather than distance vs. pace). Along with markers 3603 and 3605, graph 3601 may include a summary 3609 of the total distance run. In one or more arrangements, as illustrated in FIG. 37, an interface such as interface 3700 may include average heart rate information bar 3701.

Referring again to FIG. 36, interface 3600 may further include a heart rate range option 3611 that may be used to activate a heart rate range selector as will be discussed in further detail below with respect to FIGS. 42-48.

Figure 38:
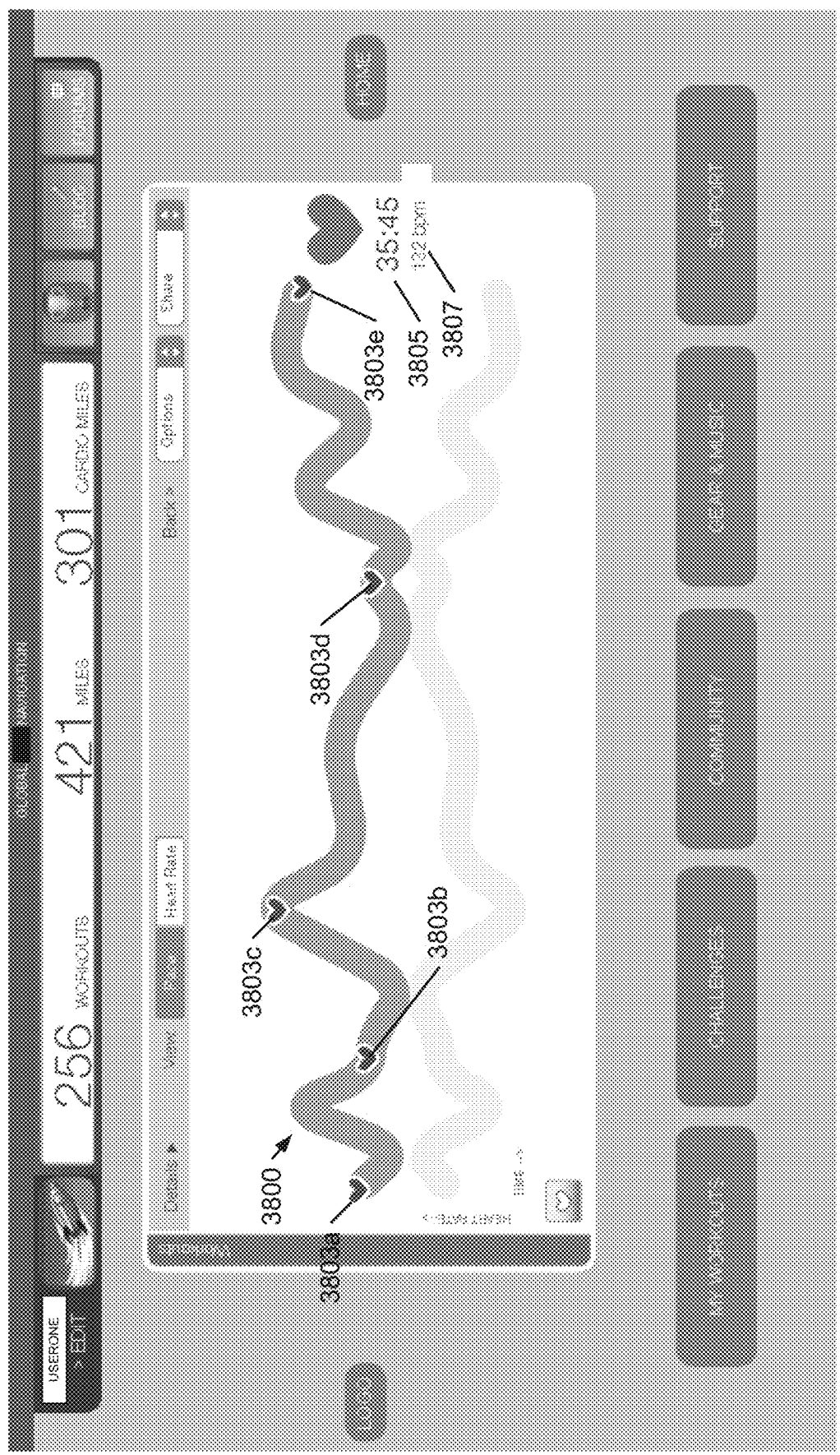
FIGS. 38 and 39 illustrate example user interfaces displaying a user's heart rate over time for a workout according to one or more aspects described herein.
Figure 39:
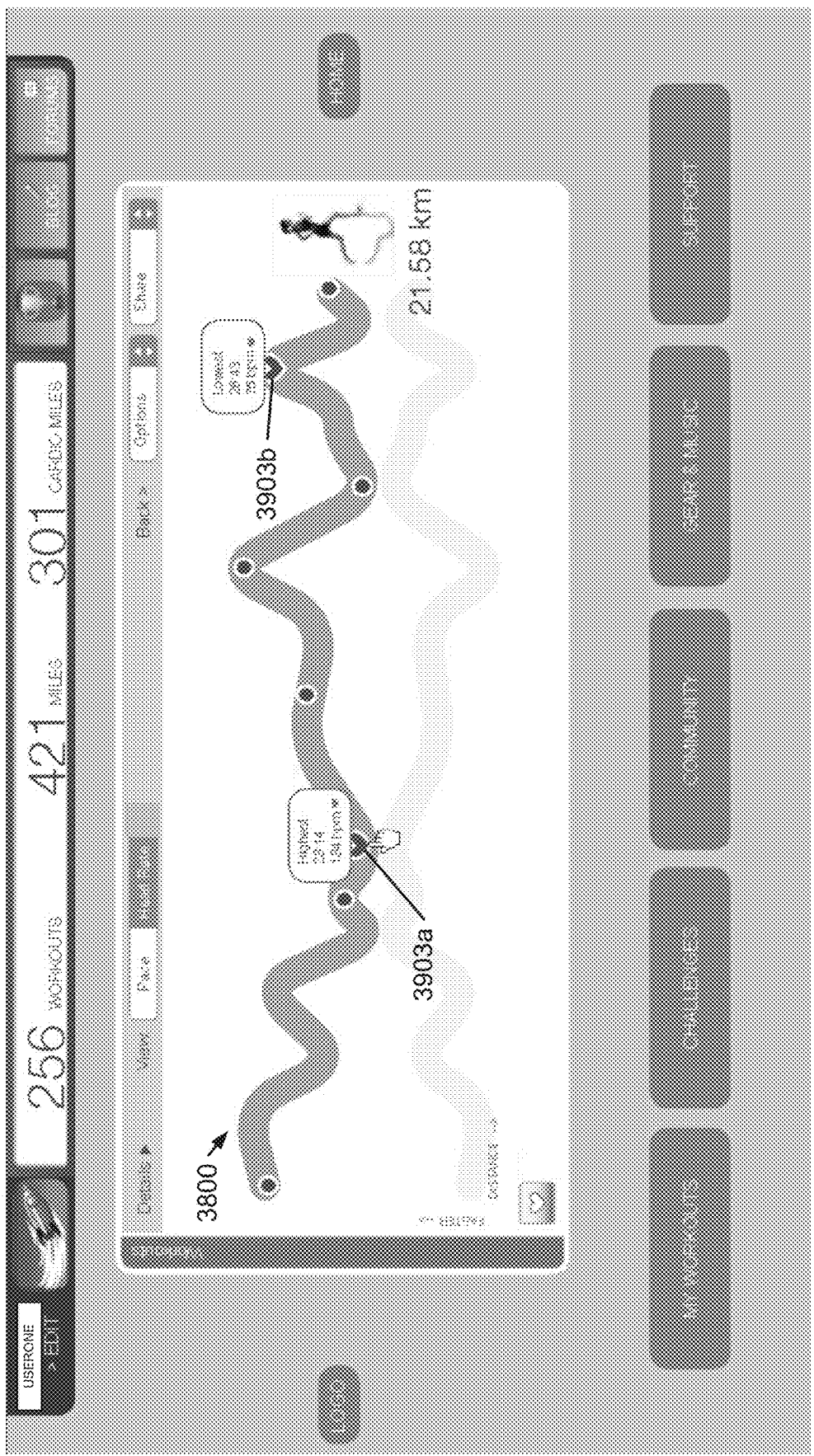

As noted herein, workout data may be displayed in either pace form or heart rate format. FIGS. 38-41 illustrate various example heart rate graphs that provide a visualization of a user's heart rate over a workout period. Heart rate may be expressed as the number of beat per minute (bpm). In FIG. 38, graph 3800 may include heart rate markers 3803 that identify predefined positions in the workout. For example, markers 3803 may be placed at every hour or other predefined amount of time, every 25% or other percentage of the workout (either based on time or distance), at every mile or other specified distance and/or combinations thereof. Total workout time 3805 may be displayed at the end of the graph along with the average heart rate 3807. FIG. 39 illustrates another example heart rate graph 3900 where heart rate markers 3903 may be placed at the beginning and end of the workout as well at the points in time where the athlete reached his highest and lowest heart rates.

Figure 40:
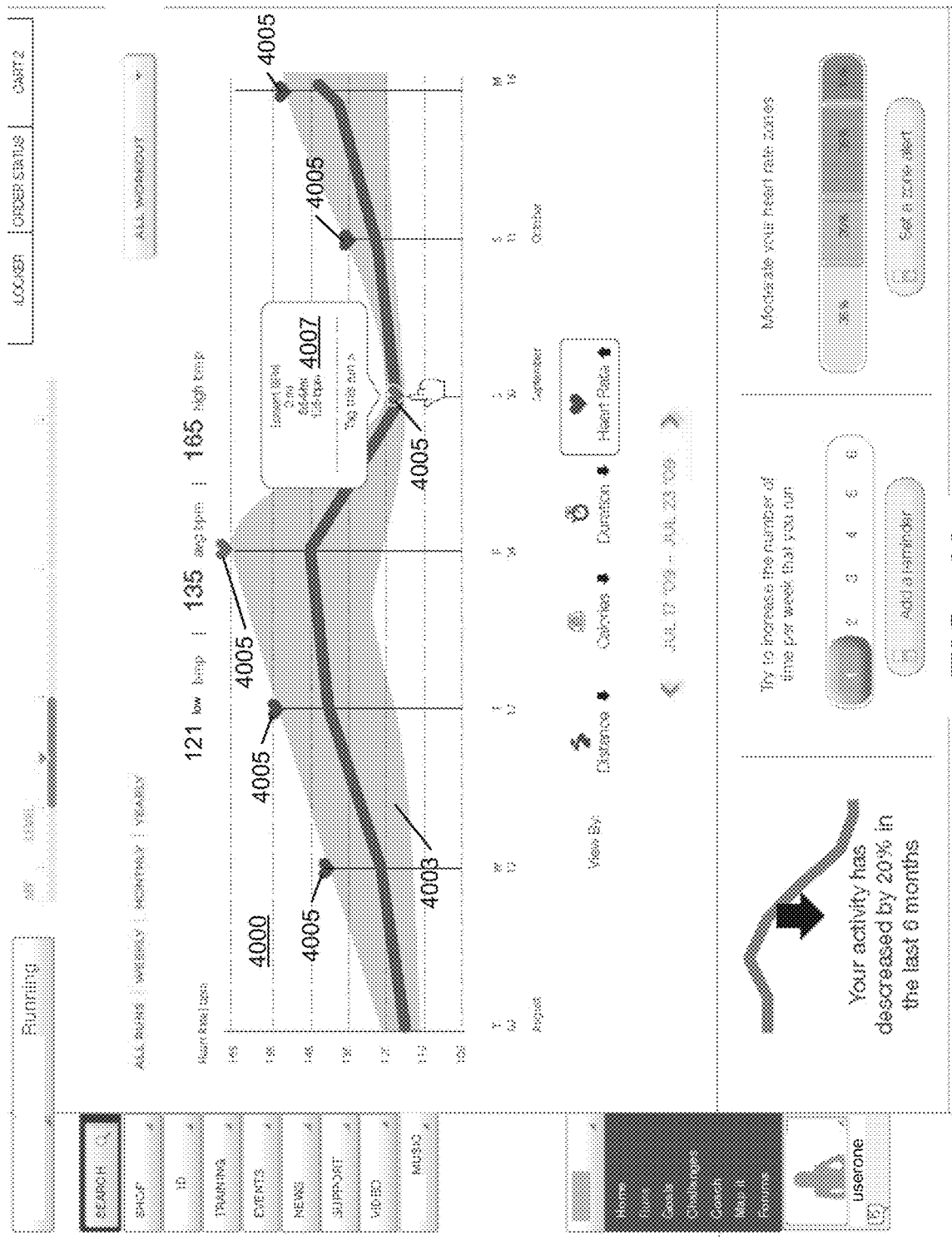
FIGS. 40 and 41 illustrate example user interfaces displaying a user's heart rate over time including an average heart rate and a range of heart rates detected according to one or more aspects described herein.

FIG. 40 illustrates a heart rate graph 4000 for multiple workouts. Since each workout may include multiple heart rate readings, heart rate graph 4000 may be configured to chart the average heart rate for each workout against time. However, the range of heart rates for each workout may also be represented and visualized in graph 4000 by the colored or grayed region 4003. In one arrangement, a user's average heart rate may be displayed along the graphed line while the range may be represented by a region having an appearance (e.g., color, pattern, transparency) different from the graphed line. Heart rate markers 4005 may be placed along the top edge of the grayed or colored region 4003 to identify the highest heart rate an athlete reached during that particular workout or day of workouts. Hovering over or otherwise interacting with markers 4005 may cause a pop-up window 4007 to be displayed. Pop-up window 4007 may include information such as the number of miles run for that workout, the average pace and the average heart rate. Additionally or alternatively, hovering within region 4003 may display a corresponding heart rate and amount of time the user exhibited that particular heart rate during that particular workout session, day or other time period. In one particular example, if a user hovers over the "T 17" workout day and around the 125 bpm mark, the interface may display an amount of time the user exhibited a 125 bpm (or a predefined range around 125 bpm such as 10% above and below, 5 bpm above and below and the like) during that workout day. In addition or alternatively to an amount of time the user exhibited a particular heart rate, the interface may display a distance or other amount of exercise performed at that heart rate.

Figure 41:
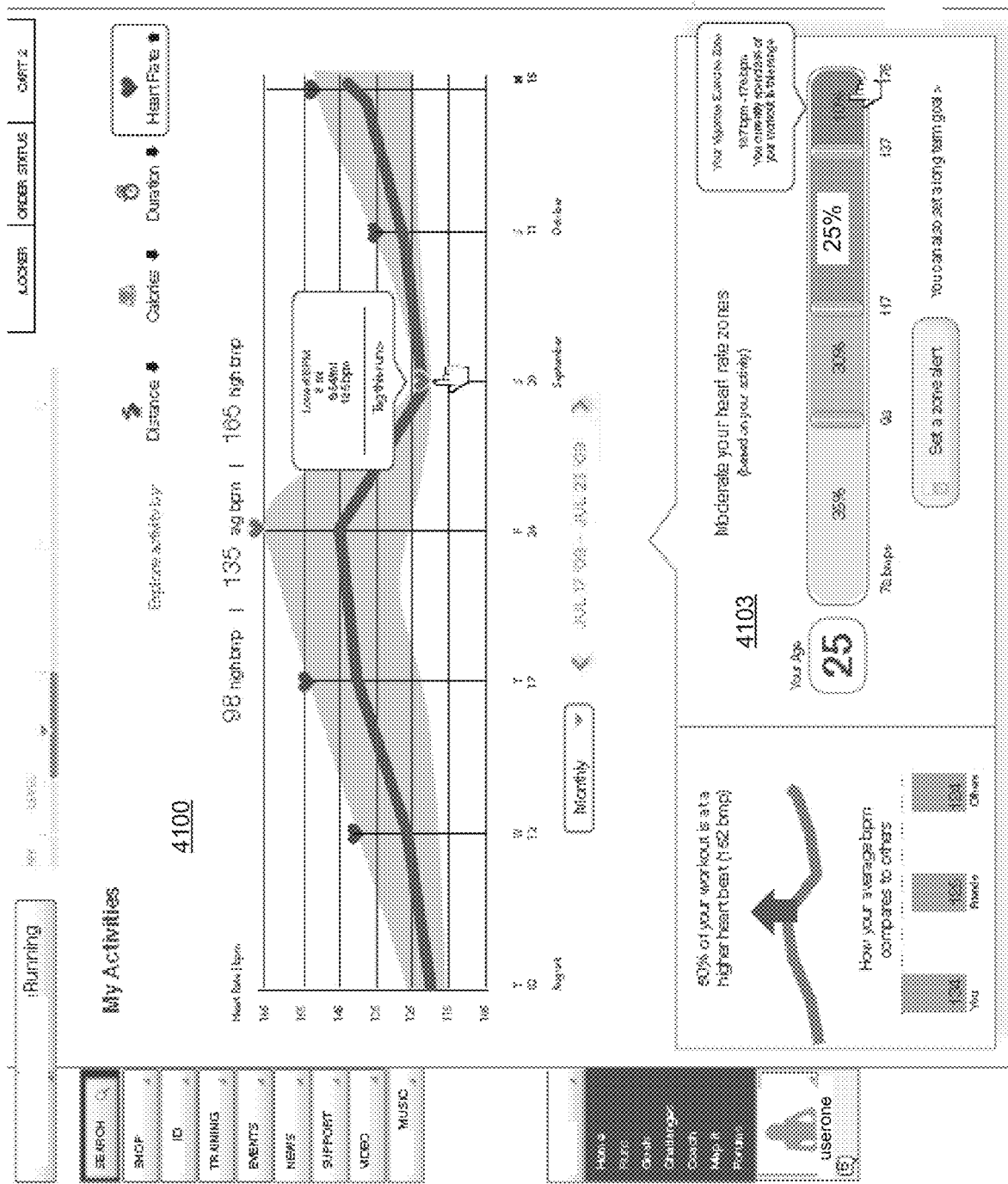

FIG. 41 illustrates another example of a heart rate graph for heart rate information over multiple workouts. Interface 4100 may include a heart zone management tool 4103 that provides the user with the option of setting alerts when the user's workout meets a predefined heart rate profile. A heart rate profile may include a specification of the amount of a workout that should fall within each of multiple heart rate ranges. In the illustration of FIG. 41, the profile specifies that the user's workout is to be 35% in the 78 to 98 bpm range, 30% in the 99 to 117 bpm range, 25% in the 118 to 137 bpm range and 10% in the 138 to 175 bpm range. If the user approaches these ranges, an alert may be sent to the user notifying the user of the same. A certain level of tolerance may be provided so that a user does not have to exactly match the heart rate profile. For example, if the user exhibits a heart rate between 138 to 175 bpm during 8% of his or her workout, the user may be determined to have matched at least the 138 to 175 bpm portion of the heart rate profile.

Figure 42:
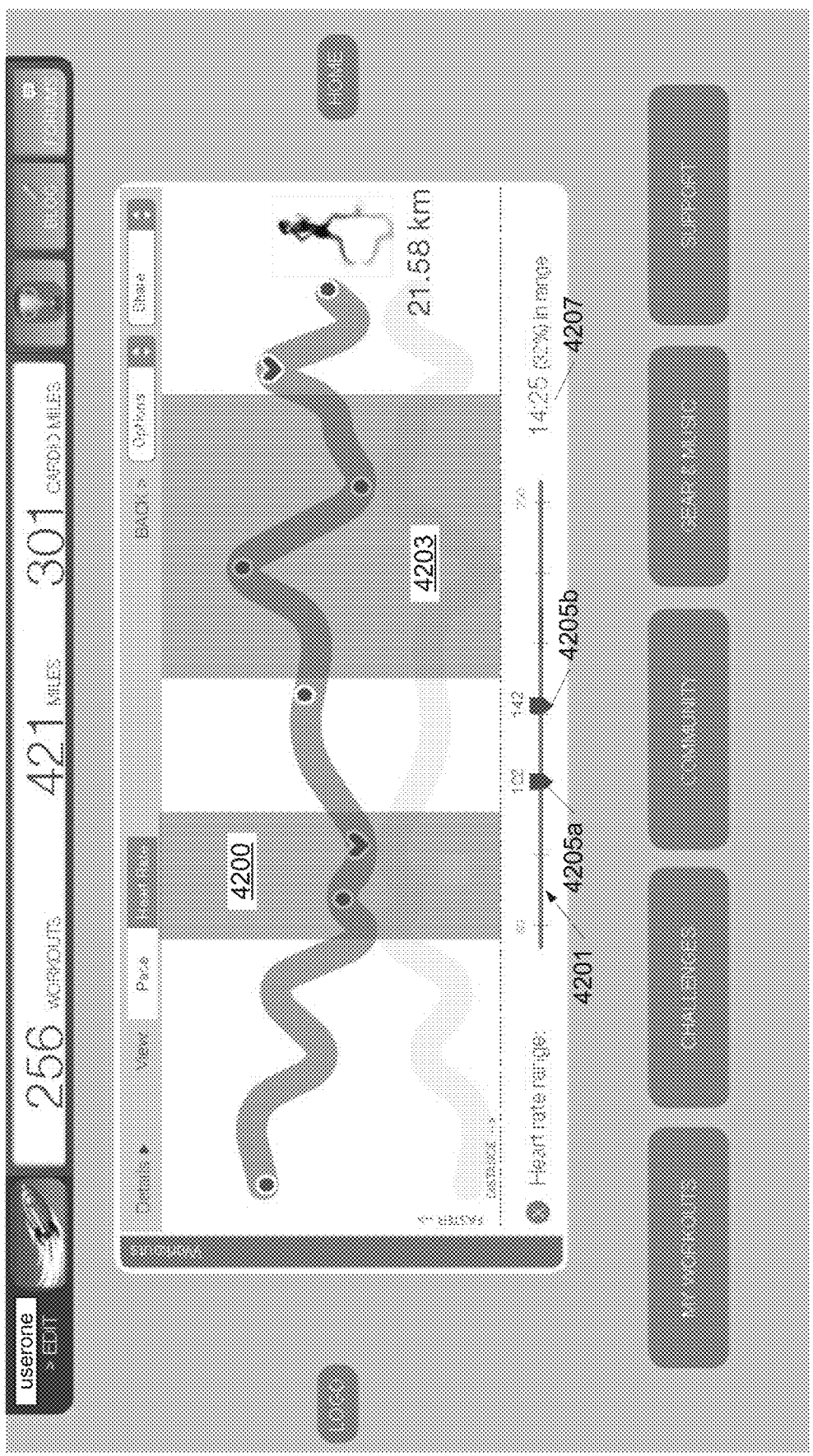
FIG. 42 illustrates an example user interface in which portions of a user's workout pace chart is identified based on a selected heart rate range according to one or more aspects described herein.

FIGS. 42-48 illustrate example interfaces wherein portions of a workout graph is highlighted based on a selected heart rate range. For example, FIG. 42 illustrates a pace graph in which various ranges or zones 4203 are highlighted, superimposed or overlaid. The interface 4200 further includes a heart rate range control bar 4201 that allows a user to select a particular range of heart rates using low end slider 4205a and high end slider 4205b. Ranges or zones 4203 may then be generated and overlaid over the portions of the workout where a user exhibited a heart range in the selected range. The generation and modification of zones 4203 may be performed in real-time as the user is modifying or selecting a desired heart rate range. For example, in control bar 4201, the user may select a heart rate range of 122-142 bpm. Accordingly, ranges 4203 represent the portions of the workout in which the user exhibited a heart rate in the range of 122-142 bpm. Interface 4200 may further include an information portion 4207 that displays the amount or percentage of time the user exhibited that range of heart rates (e.g., 14 minutes and 25 seconds and 32%). In one or more arrangements, instead of displaying highlighting bars 4203, the interface may modify the appearance of the relevant segments of the line graph in which the user exhibited the selected range of heart rates. For example, the matching portions of the line graph may be displayed in another color, with a different pattern and/or the like.

Figure 43:
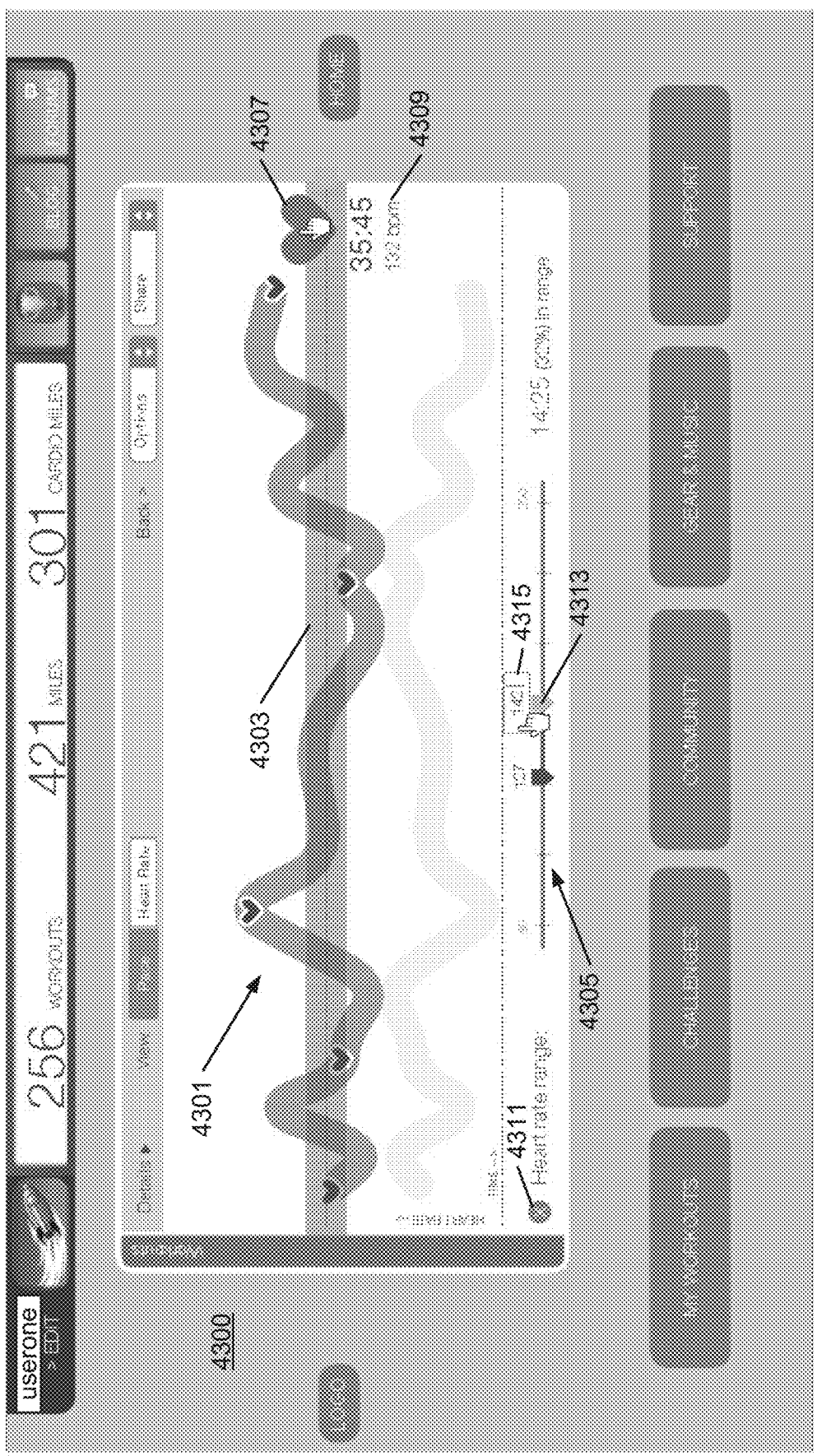
FIGS. 43-50 illustrate example user interfaces in which portions of workout heart rate chart are identified based on a selected heart rate range according to one or more aspects described herein.

FIG. 43 illustrates an interface 4300 in which a heart rate graph 4301 is overlaid by a heart rate range 4303. Interface 4300 may include (similar to interface 4200 of FIG. 42) a heart rate range control bar 4305 that allows a user to select a desired heart rate range to highlight. Option 4311 further allows a user to hide heart rate range control bar 4305. In one or more arrangements, hovering over or otherwise interacting with heart rate control bar 4305 for a predefined amount of time causes one or more portions (e.g., the upper or lower limit markers) to change in appearance to indicate that the bar 4305 is editable or modifiable. For example, upper limit 4313 may be enclosed in an edit box 4315 to indicate that it may be modified. According to one or more aspects, the heart range control bar 4305 may automatically default to an average heart rate of the workout with upper and lower limits being + and −10 bpm, respectively, from the average. Additionally or alternatively, interface 4300 may be characterized by a heart rate icon 4307 that provides an indication of the type of graph shown. Hovering over, selecting, clicking or otherwise interacting with icon 4307 may cause additional information such as an average heart rate 4309 to be displayed.

According to another aspect, upon selecting a heart rate range, various heart rate indicators may be modified based upon the selected range. For example, high heart rate and low heart rate indicators may be modified to reflect the locations along the line graph where the user exhibited the high heart rate and low heart rate within the selected range. In another example, the location of an indicator identifying the location where the user's heart rate exhibited the greatest change may be modified to reflect the greatest change within the selected heart rate range.

Figure 44:
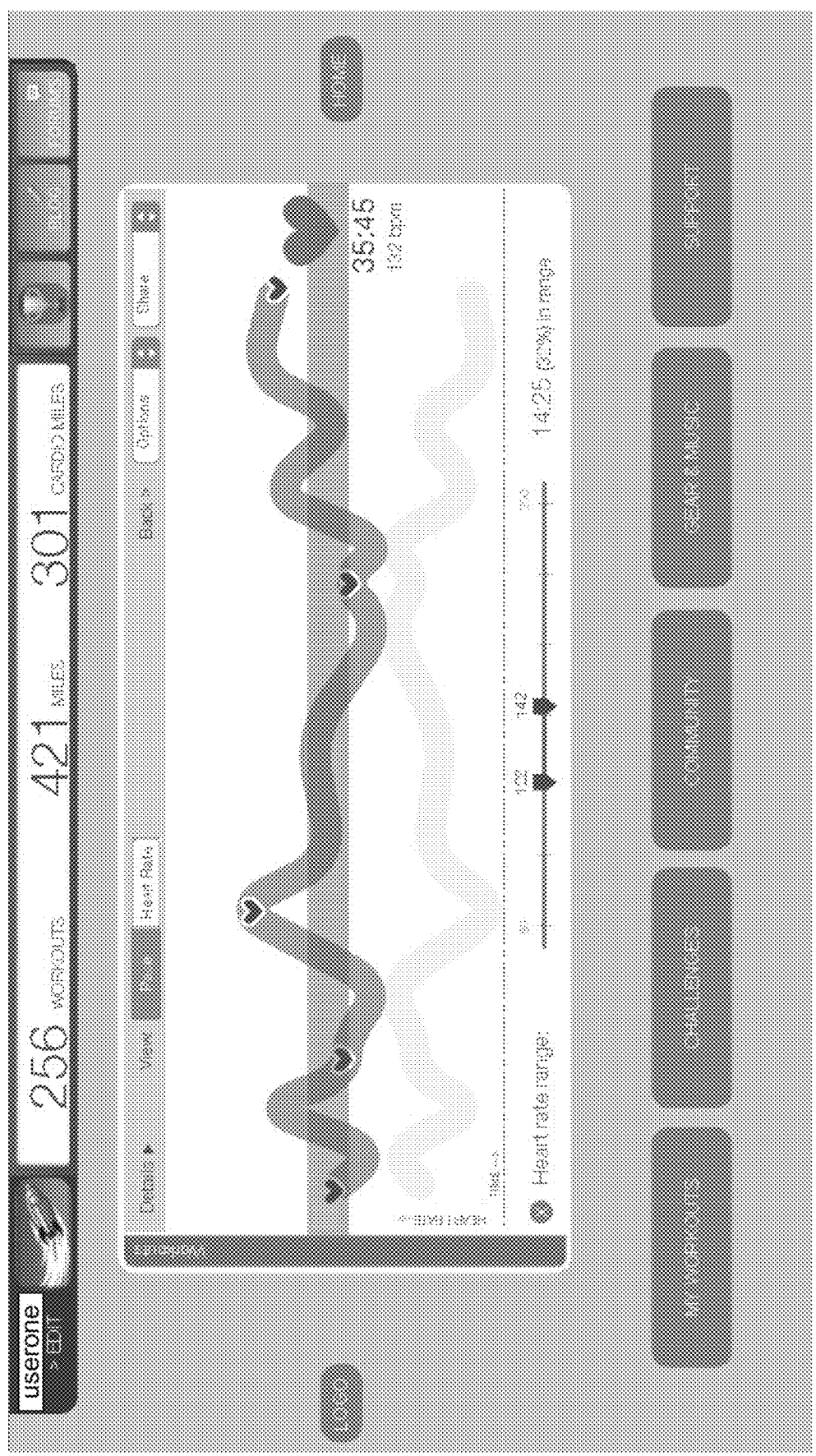
Figure 45:
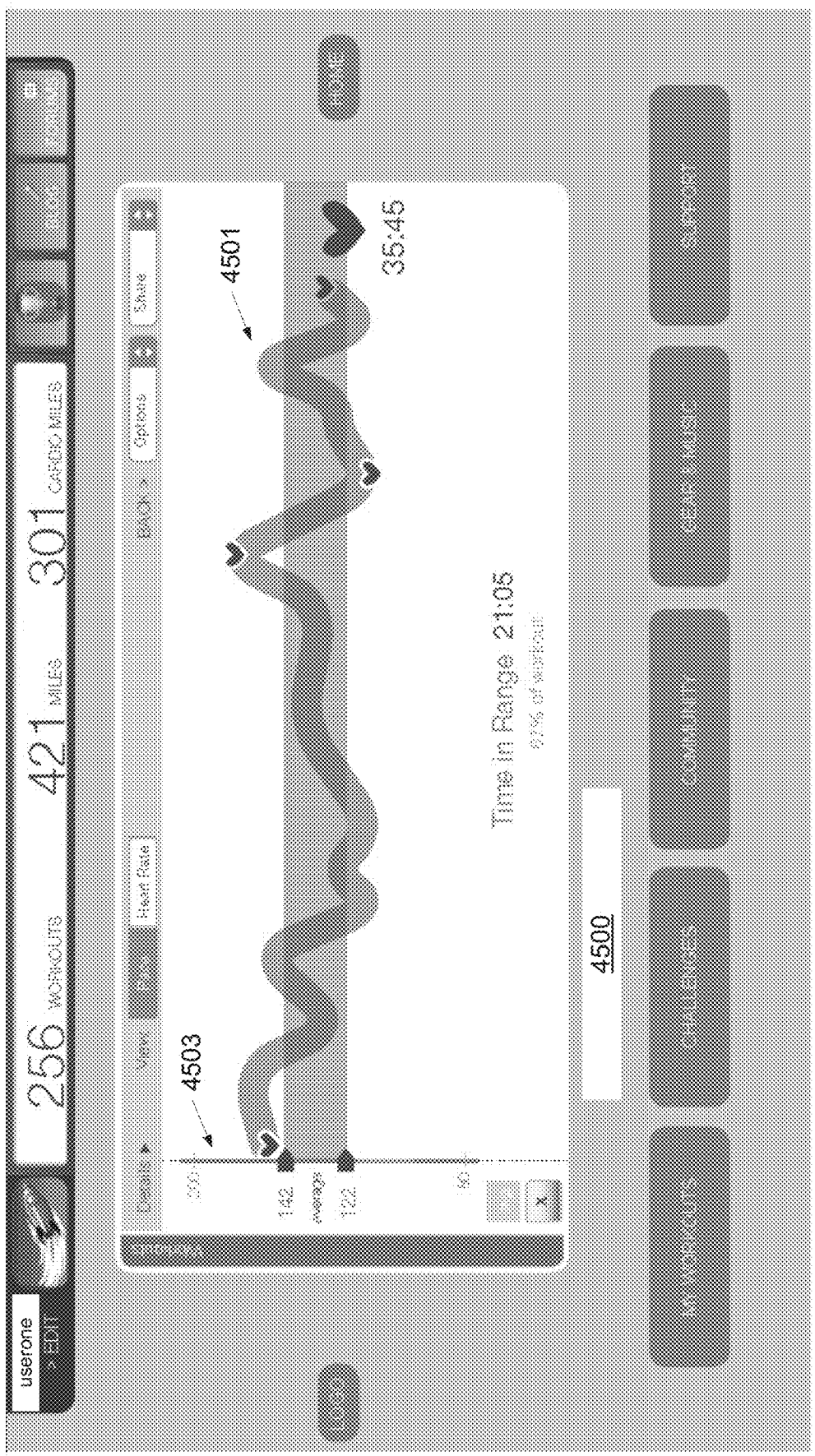
Figure 46:
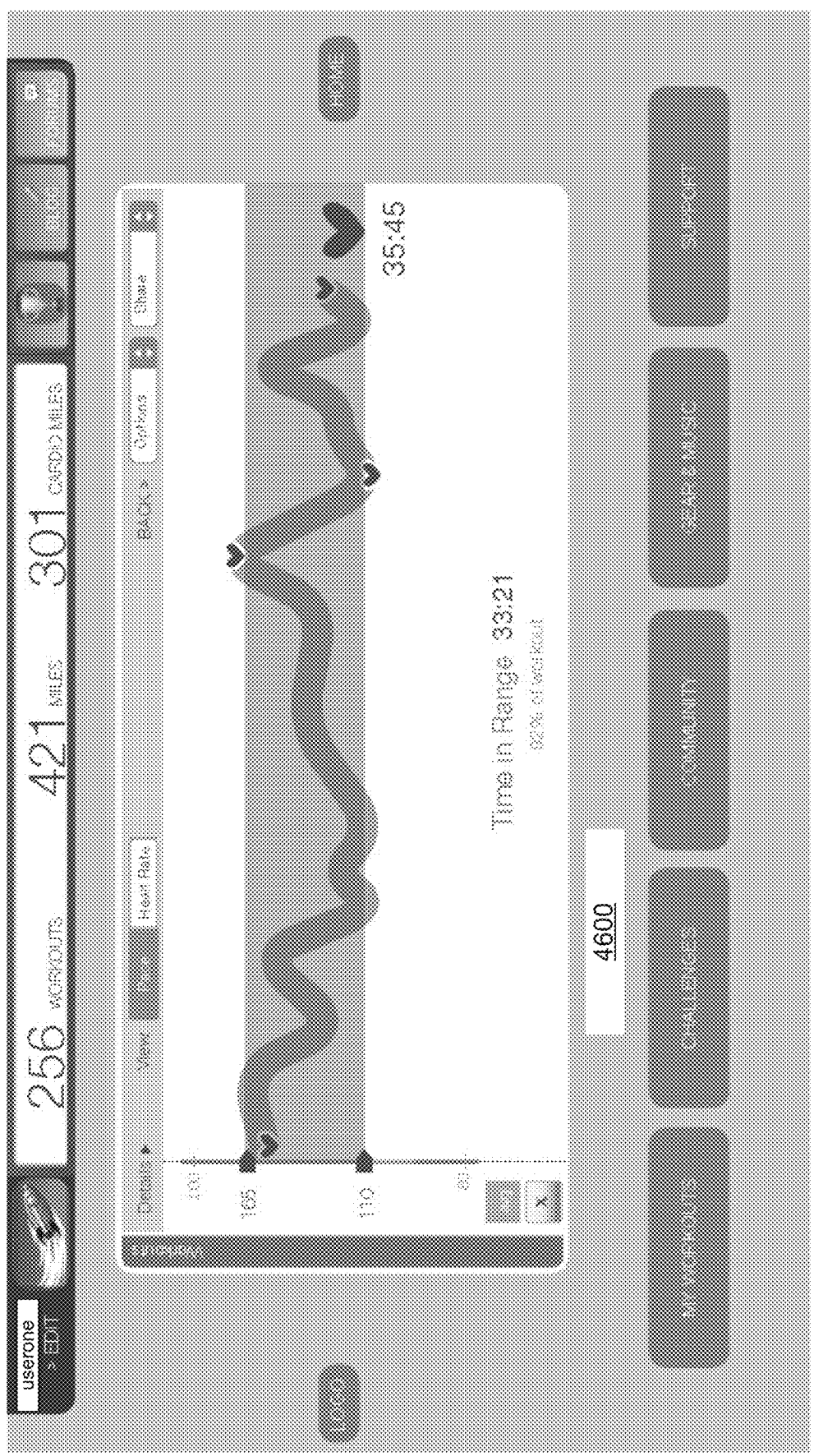

FIGS. 44-46 illustrate further example interfaces displaying heart rate information for a workout and identifying portions of a workout corresponding to a particular heart rate range. In FIG. 45, in contrast to the heart rate range control bars 4203 (FIGS. 42) and 4305 (FIG. 43), heart rate range control bar 4503 may be displayed along and integrated with the y-axis of graph 4501 of interface 4500. Such a configuration may allow a user to directly correlate the position of the upper and lower limits of the specified heart rate range with the various portions of graph 4501. In FIG. 46, interface 4600 may further display a percentage of the workout that corresponding to the selected heart rate range. For example, in interface 4600, 90% of the workout is included in the 110-165 bpm heart rate range.

Figure 47:
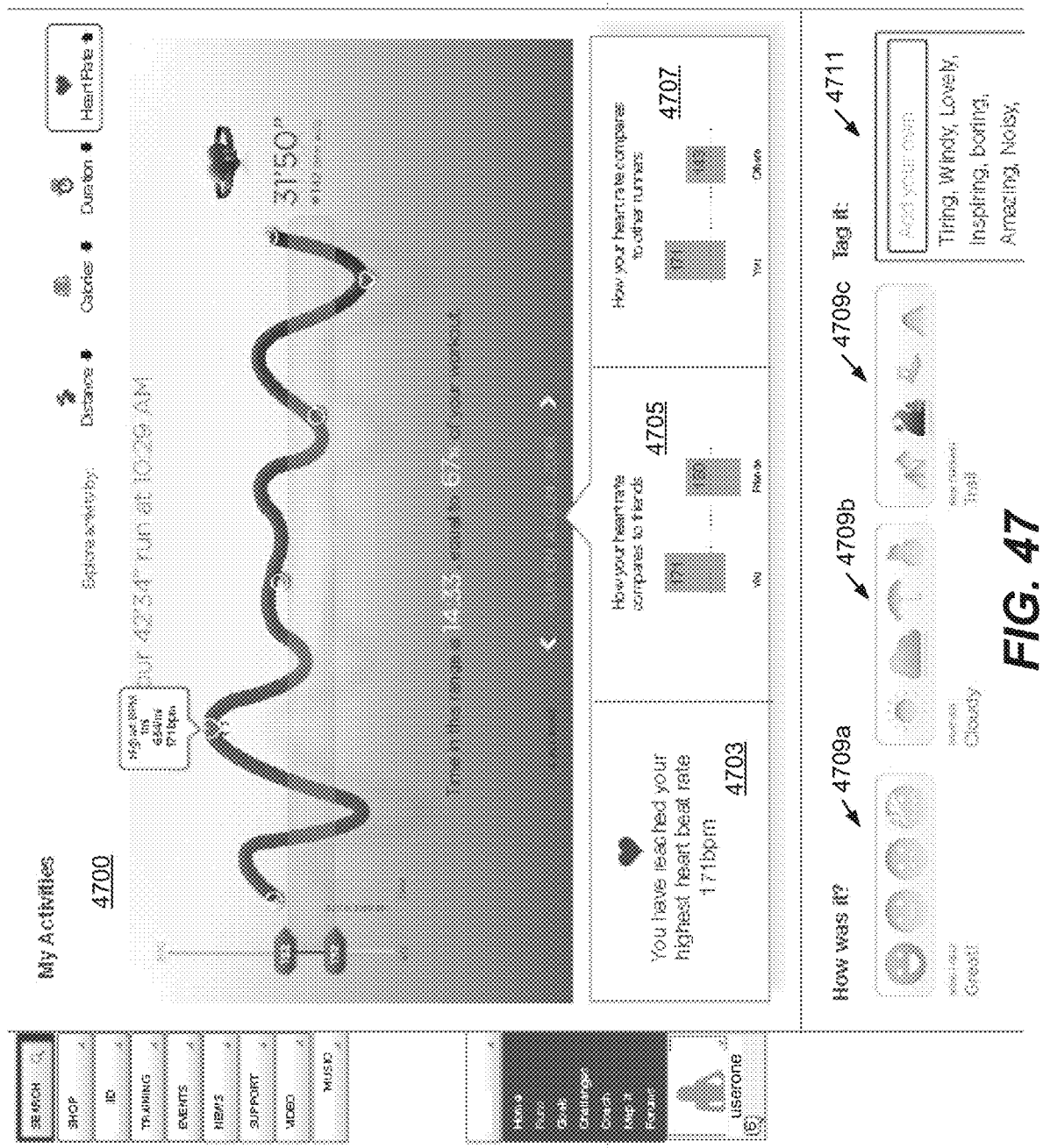
Figure 48:
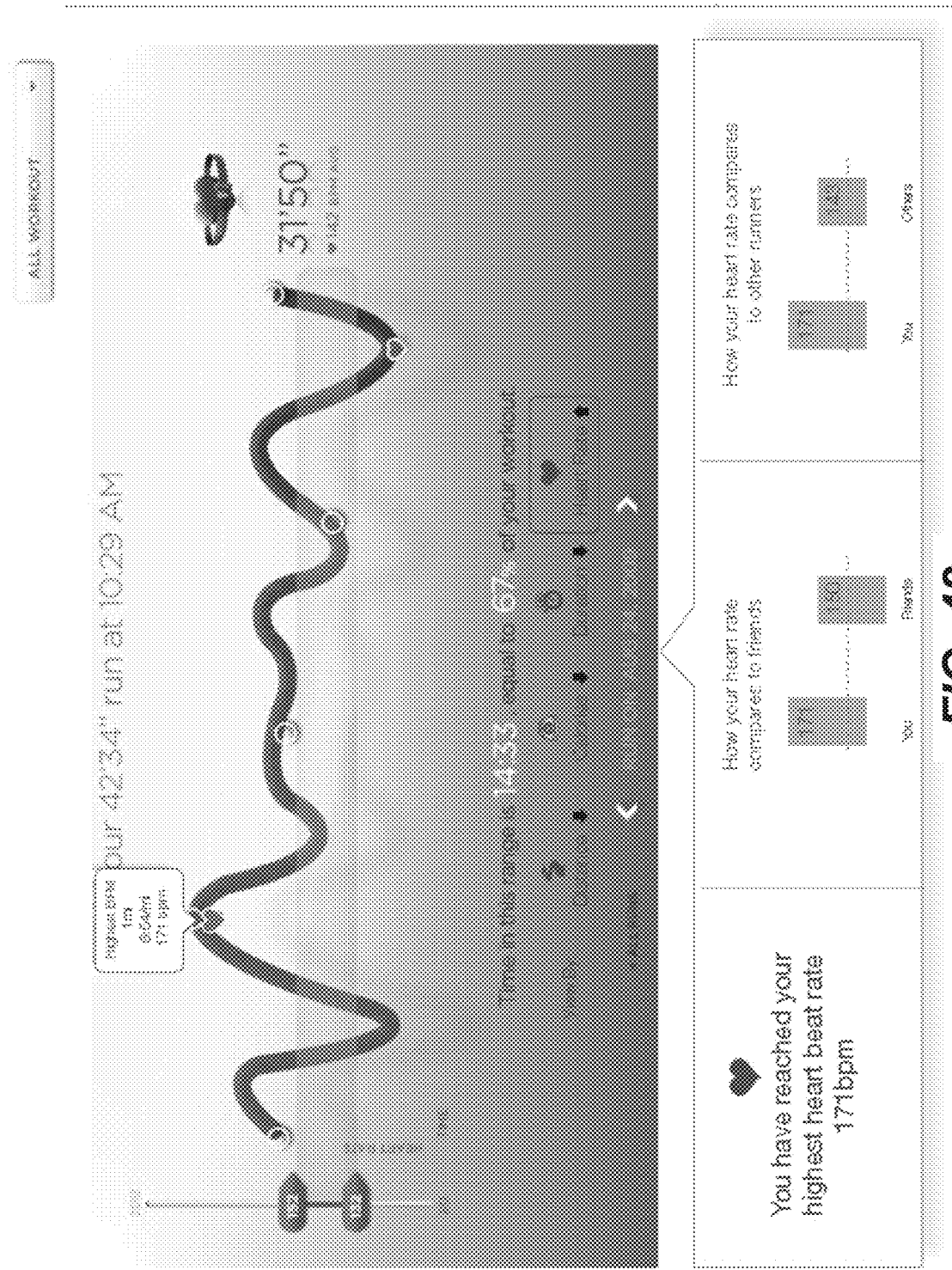

FIGS. 47 and 48 illustrate other example interfaces that are configured to identify portions of a user's workout that correspond to a particular heart rate range. Interface 4700 may include further information including a highest heart beat rate 4703, a comparison 4705 of the user's highest heart rate to that of the user's friends and a comparison 4707 of the user's heart rate to that of the others. Interface 4700 may further include options 4709 that allow the user to indicate the user's feeling about the workout (4709a), the weather associated with the workout (4709b) and a type of workout terrain (4709c). Other words, phrases, images and the like may be used to tag the workout using tagging option 4711. Tagging may allow a user to more easily find workout entries by searching for the words or phases with which the entries have been tagged. Additional tagging options are discussed below with respect to FIG. 59.

Figure 49:
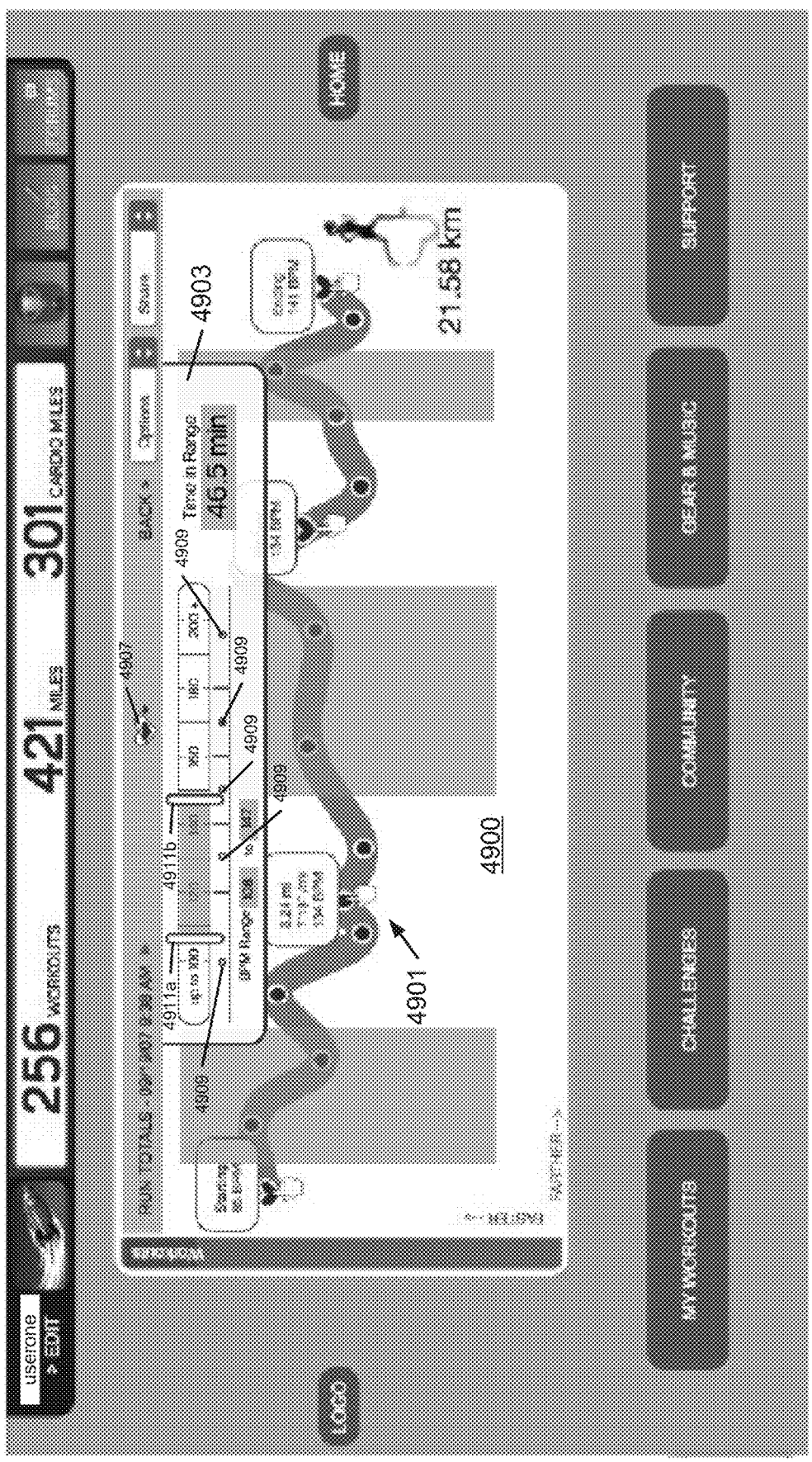
Figure 50:
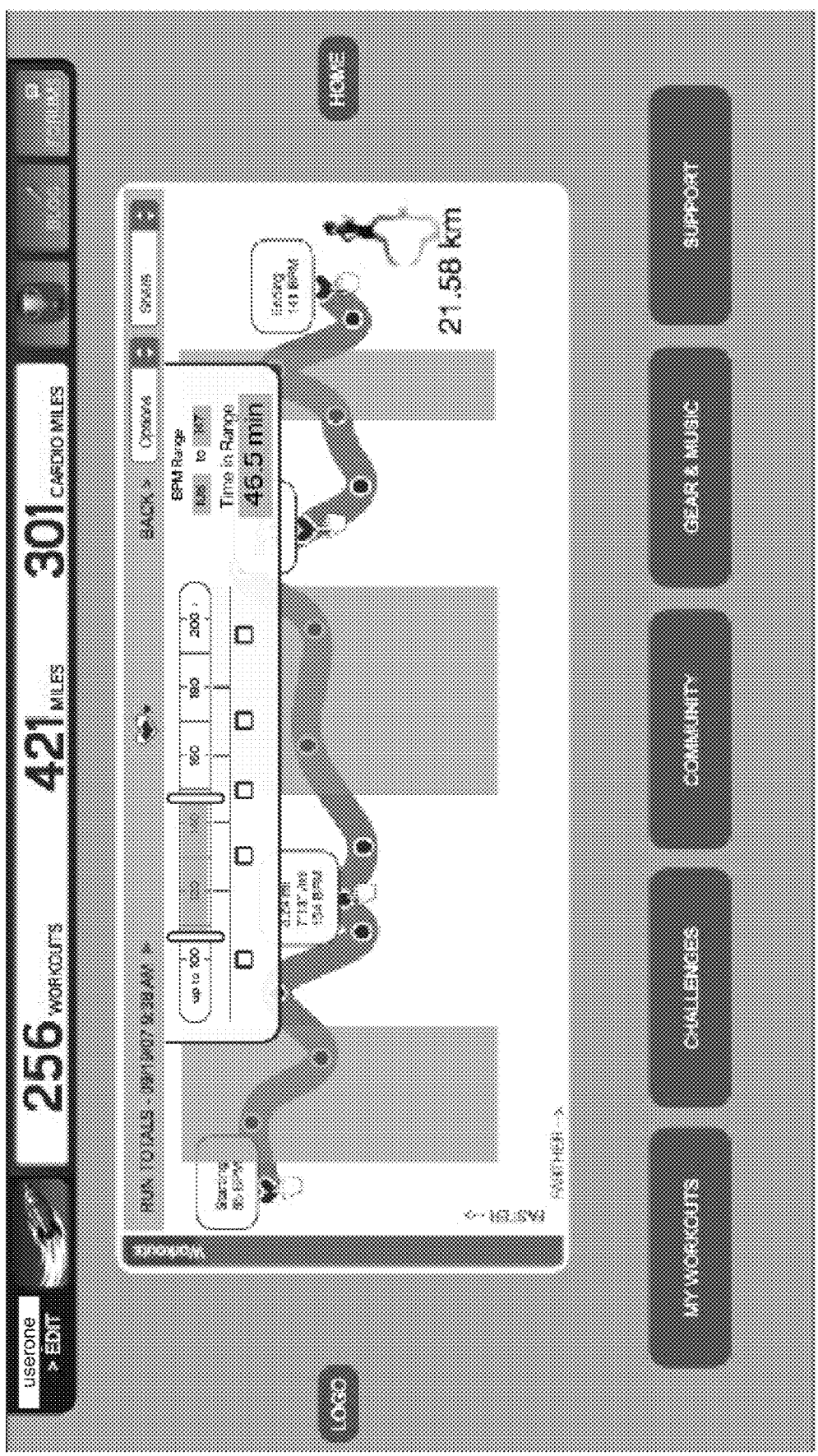

FIGS. 49 and 50 illustrate example interfaces in which the heart rate range control bar 4903 is provided as a drop down menu upon selection of heart rate control option 4907. When exposed, the heart rate range control bar 4903 may overlay a portion of graph 4901. Heart rate range control bar 4903 may include multiple predefined range selectors 4909 that allows a user to identify predefined ranges on graph 4901. The predefined ranges, in one or more example, may include up to 120, 121-140, 141-160, 161-180 and 181 and over. Thus, selecting one of selectors 4909 may automatically modify and/or define the range to the predefined range corresponding to the selector. Alternatively or additionally, the user may choose to create a custom heart rate range using sliders 4911a and 4911b. Each selected range may be identified using a different pattern, color, hue and/or combinations thereof. In one or more arrangements, interface 4900 might only allow the user to select and view one range at a time. In one or more examples, the user may choose and display multiple heart rate ranges simultaneously using different appearance characteristics such as color, pattern, transparency, brightness, hue, tone, flash and the like.

Figure 51:
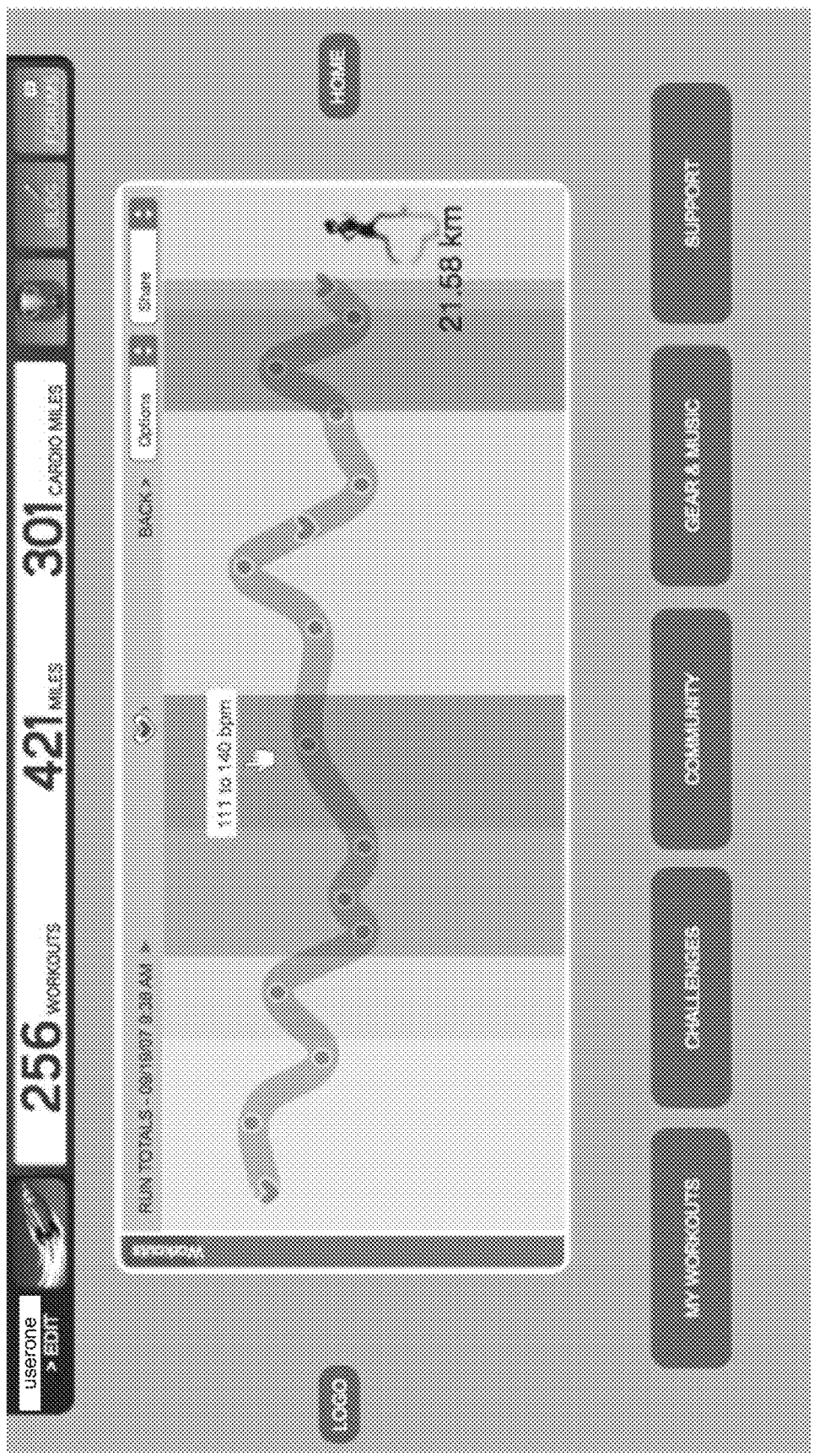
FIGS. 51 and 52 illustrate example user interfaces in which multiple portions of a workout chart are identified in different manners depending on a heart rate range corresponding thereto according to one or more aspects described herein.
Figure 52:
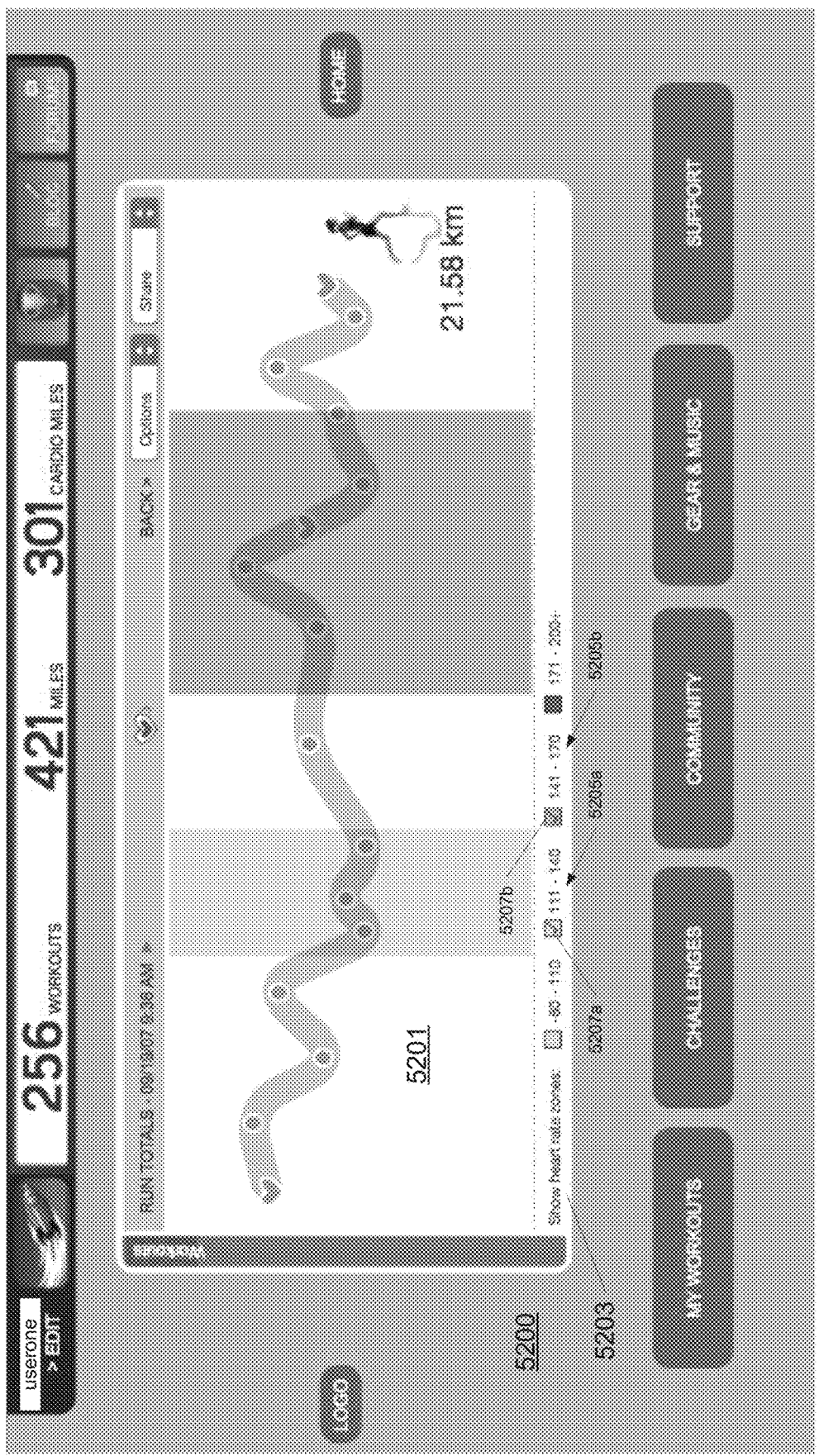
Figure 53:
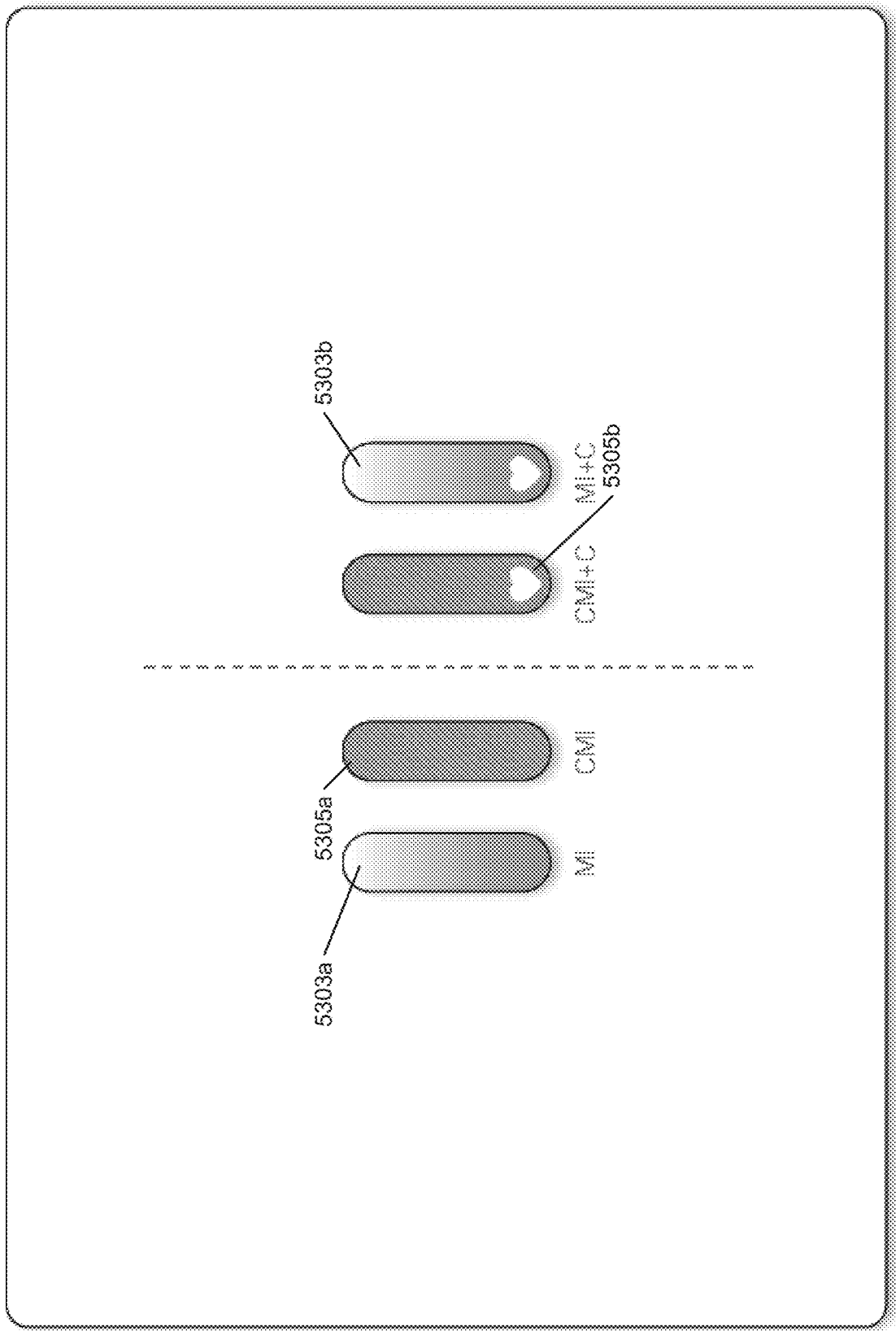
FIG. 53 illustrates an example manner in which different units of measurement may be visually differentiated according to one or more aspects described herein.

FIGS. 51 and 52 illustrate graphs of heart rate workouts in which multiple heart rate ranges are identified using different colors simultaneously in the interface. Range information may be displayed upon hovering over or otherwise interacting with one of the identified zones as illustrated in the example interface of FIG. 51.

In FIG. 52, for example, a legend 5203 is provided at the bottom of graph 5201 to indicate the colors representing each of the ranges and to allow a user to control which ranges are selected and displayed. In interface 5200, ranges 5205a and 5205b are selected for identification in graph 5201. The selection buttons 5207a and 5207b corresponding to ranges 5205a and 5205b, respectively, are provided in different colors corresponding to the colors used to identify the portions of the user's workout corresponding to those ranges. The predefined ranges 5205 may be predefined based on a default configuration, based on a coach or third party input, based on a user's preferred configuration or setting or the like. For example, a user may define preferences to indicate a set of preferred ranges. Upon accessing a visualization of a workout, the user may be offered those preferred ranges for viewing heart rate information.

Figure 54:
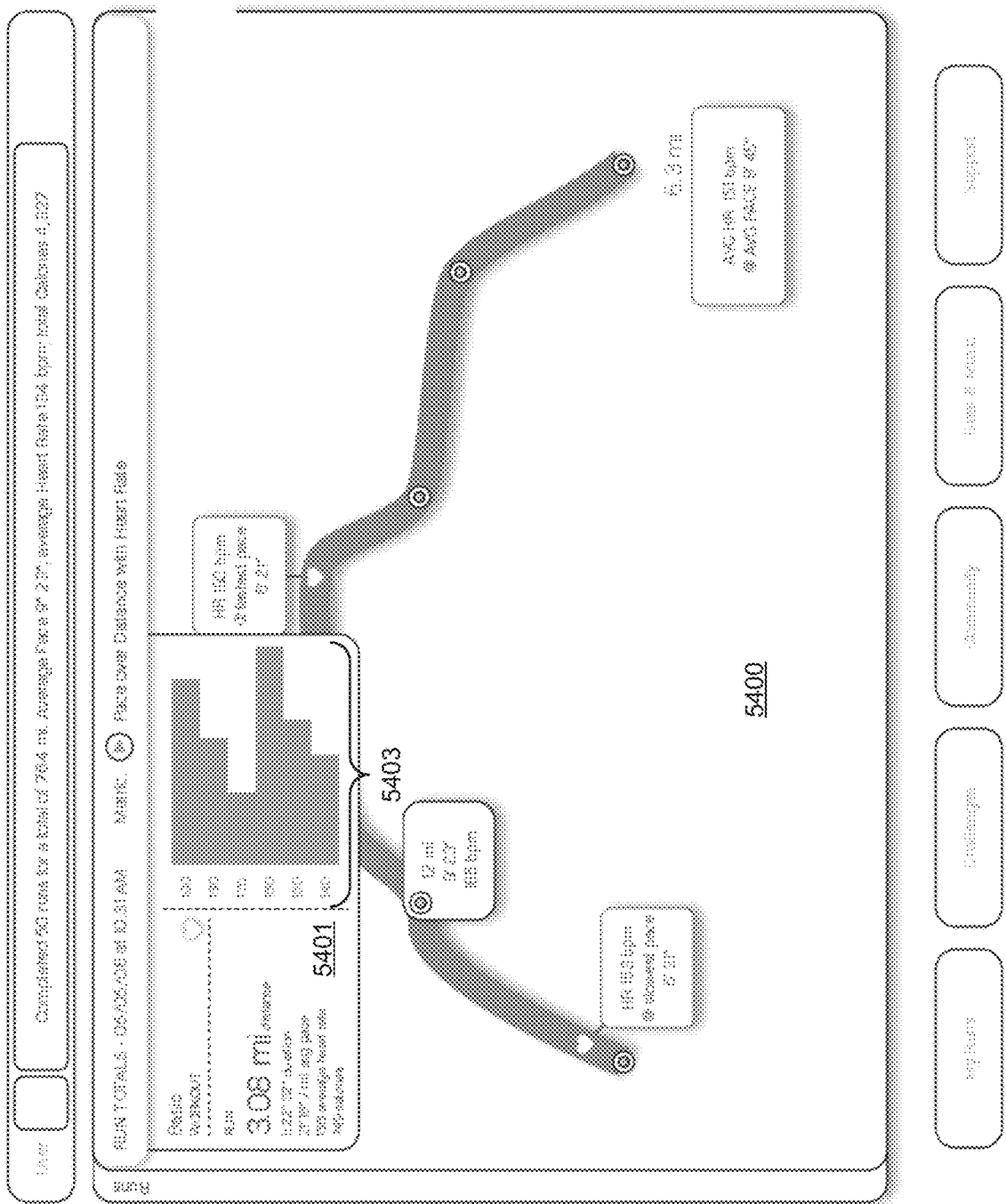
FIGS. 54 and 55 illustrate additional example user interfaces displaying pace over distance workout information according to one or more aspects described herein.

FIG. 54 illustrates a portion of a pace over distance graph in which a heart rate summary is displayed in a portion of interface 5400. Summary 5401 may include a variety of information including the type of workout, the distance, the duration, a pace, an average heart rate, a number of calories burned and a graph 5403 of how much time was spent in each displayed heart rate zone. For example, the bars in graph 5403 may represent the number of minutes and/or seconds spent in a heart rate range of 140-149, 150-159, 160-169, 170-179, 180-189 and 190-199. Other ranges may be used and/or automatically determined based on the actual heart rates exhibited for the workout.

Figure 55:
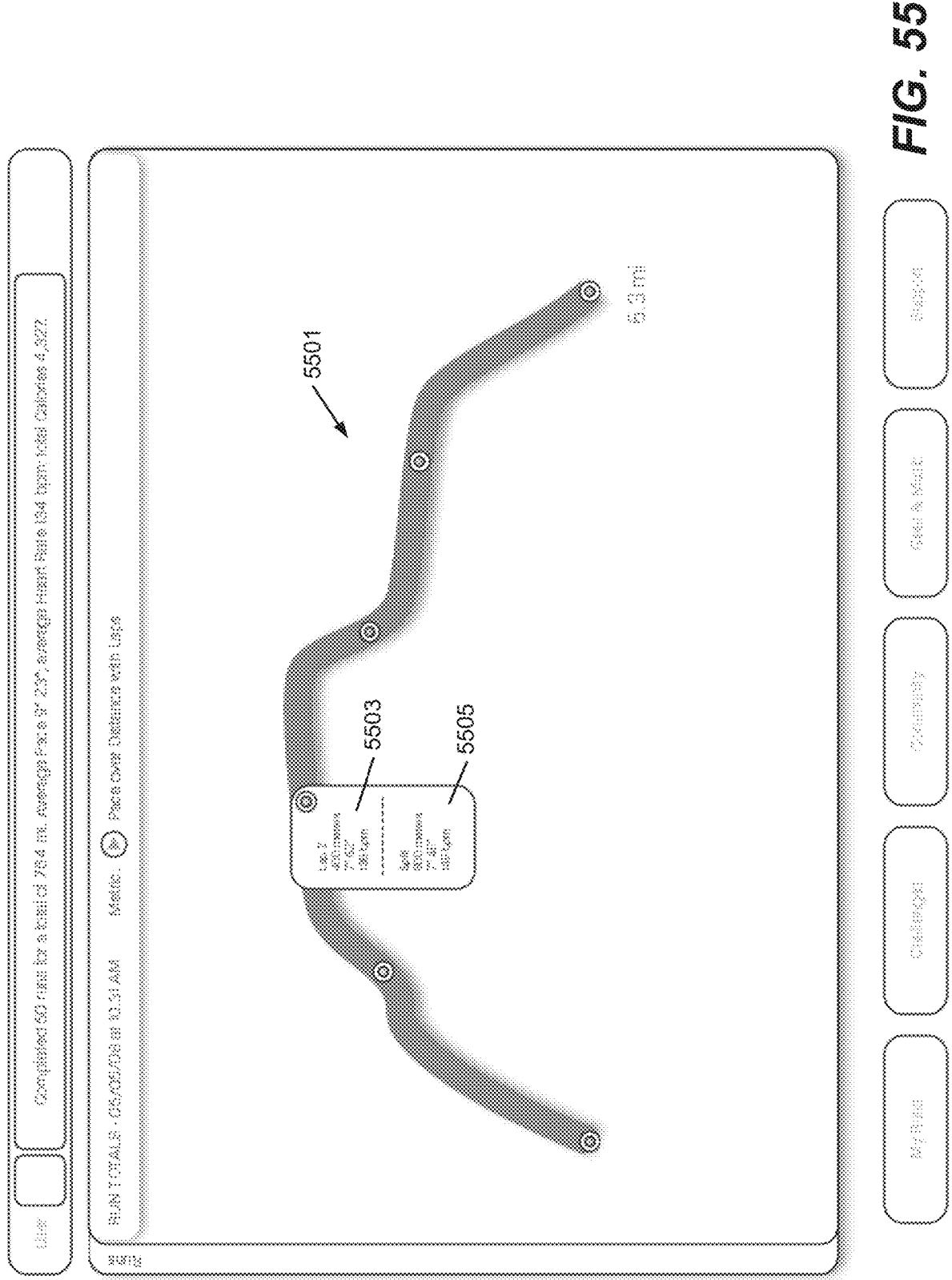

FIG. 55 illustrates another example pace graph 5501 in which the athlete's actual lap time 5503 is displayed with a split time 5505. This display may allow the user to compare his current pace with a desired pace. Additionally, heart rate information for the current workout and for the split may also be displayed for purposes of comparison. The split may be generated from a previous workout or based on a target workout. The target workout may be defined by the user or a third party such as a coach (e.g., by setting desired 400 meter times and 800 meter times as well as desired heart rates at predefined points of the workout) or selected from a library of predefined workouts.

Figure 56:
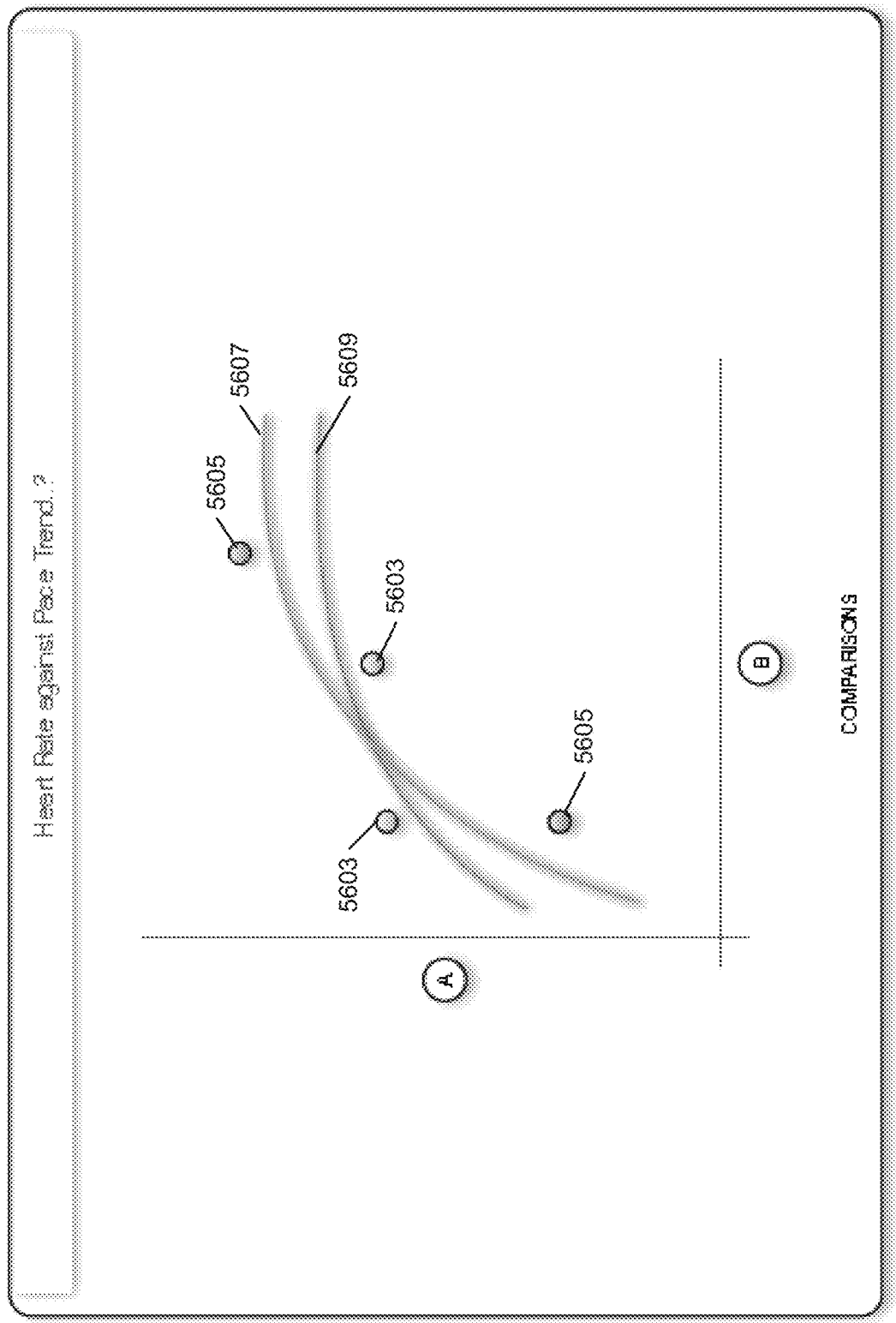
FIGS. 56 and 57 illustrate example user interfaces displaying trends for heart rate and pace information for a workout according to one or more aspects described herein.
Figure 57:
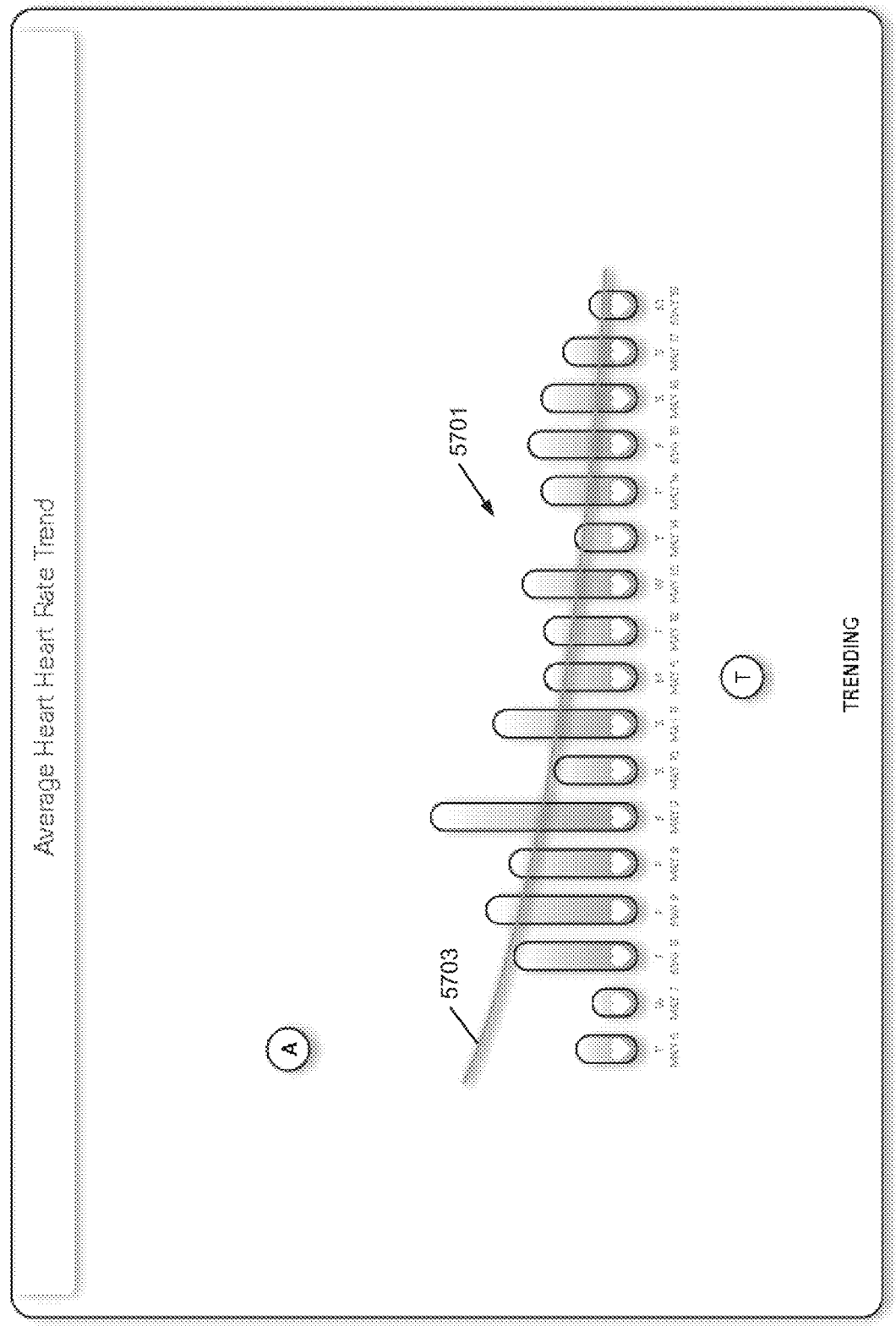

FIGS. 56 and 57 illustrate graphs of heart rate and/or pace information along with trend lines. The trend line may be configured to aid an athlete in determining whether the athlete is improving or regressing in his workouts. For example, in FIG. 56, pace data points 5603 may be represented in one color while heart rate data points 5605 may be displayed in a second color. Trend lines 5607 and 5609 may then be generated and displayed for each of heart rate data point 5605 and pace data points 5603, respectively.

FIG. 57 illustrates a heart rate graph 5701 in which a user's average heart rate for each day is represented as a bar. A trend line 5703 may overlay or be superimposed on graph 5701 to represent the user's trend in heart rate for his or her workouts. As illustrates, trend line 5703 indicates that the user's heart rate has been declining over the displayed time range. This may help the athlete determine whether they should increase the pace of their workouts, increase the length of workouts, change the type of workouts or the like.

Figure 58:
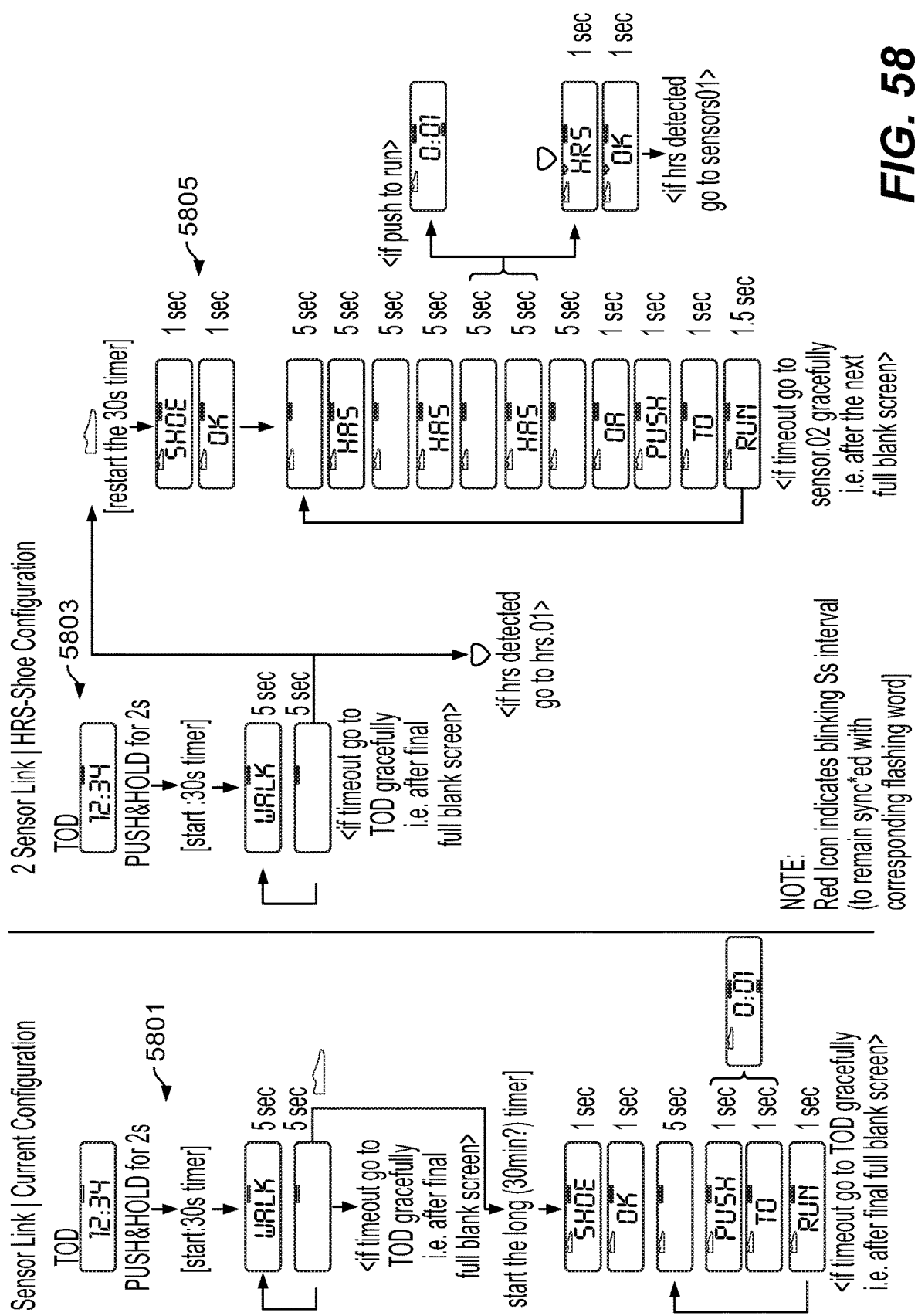
FIG. 58 illustrates example flowcharts for navigating and configuring an athletic performance monitoring device according to one or more aspects described herein.
Figure 58:
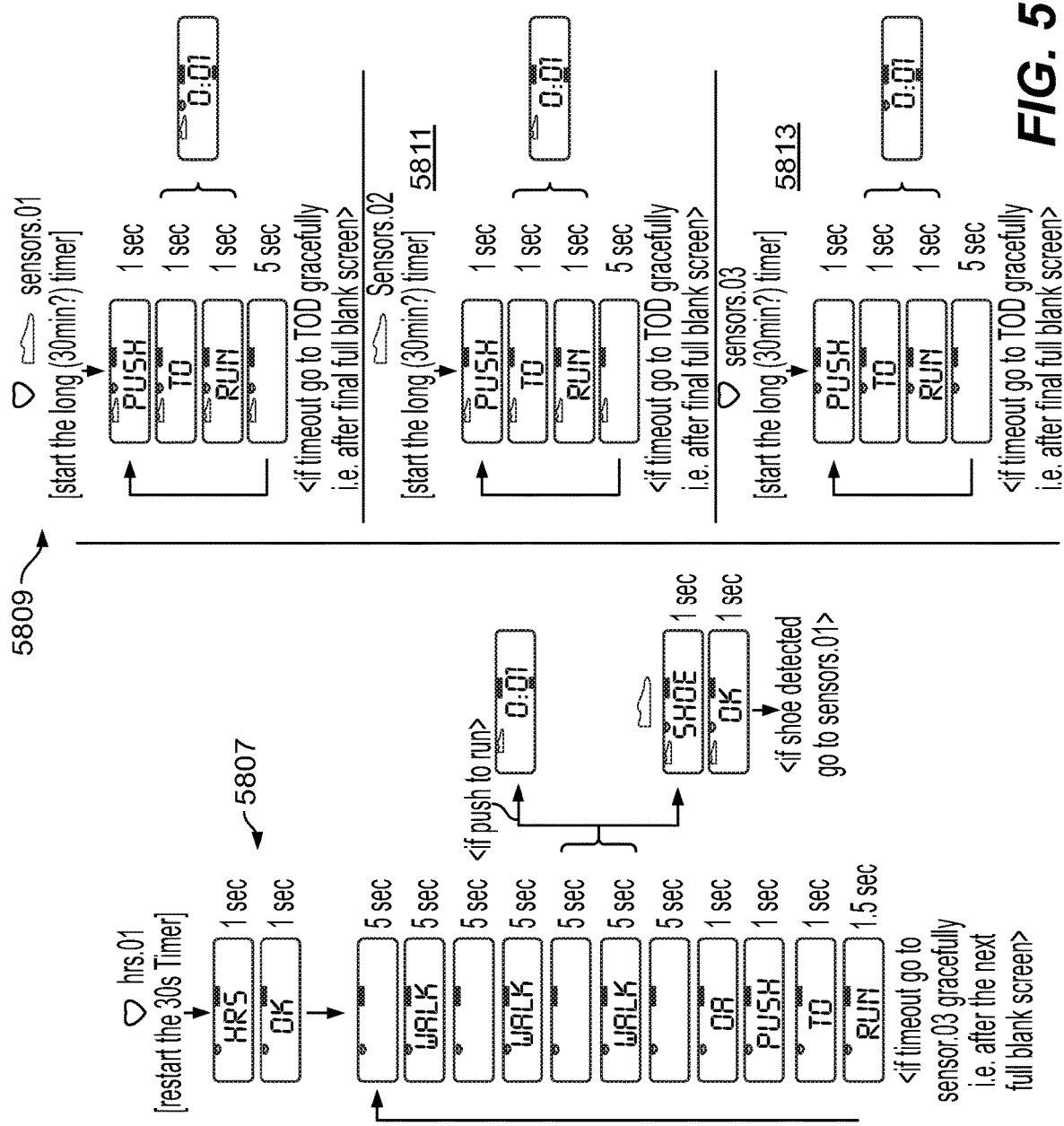

As described herein, an athlete may wear various types of devices to monitor their workout. In one or more examples, a watch or athletic band may be used to receive sensor data from a heart rate sensor, a pedometer, an accelerometer and the like. FIG. 58 illustrates a series of flowcharts illustrating configuration and initiation screens for activating and using a monitoring device. For example, flowchart 5801 illustrates the use of only a shoe based sensor such as a pedometer or accelerometer. A user may initially be presented with a time display. Upon pressing and holding a specified button for a predefined amount of time (e.g., 2 seconds), the display may display the word "WALK" and begin a 30 second timer. If user movement is not detected either because the user is not walking or a sensor is not transmitting data, the device may timeout and return to a time display. If, however, athlete movement is detected, the words "SHOE" and "OK" may be displayed in sequence, followed by the words "PUSH," "TO" and "RUN" instructing the athlete to push a specified button to begin the run workout. If the button is not pressed within a predefined amount of time, the device may timeout. If the button is pressed within the predefined amount of time, the device may begin to record performance data.

Flowchart 5803 illustrates a series of displays that may be generated when the monitoring and data collection device is configured to receive data from both a shoe based sensor and a heart rate sensor. As described with respect to flowchart 5801, the user may activate a workout mode on the device by pressing a specified button for a specified amount of time. The monitoring device may then request that the user begin walking so that the sensors can be detected and the data transmission tested. Depending on if shoe based sensor data or heart rate data is received first, the device may proceed to flowchart 5805 or 5807. For example, if shoe based sensor data is received first, flowchart 5805 illustrates that the words "SHOE" "OK" is displayed to notify the user that the shoe sensor has been detected and is working appropriately. The device may then proceed to detect the heart rate sensor. During this time, the letters "HRS" may be displayed on and off for a predefined amount of time (e.g., 0.5 seconds every 1 second for 3 seconds). The device may further provide the user with the option to begin the workout without trying to detect a heart rate by displaying "OR," "PUSH," "TO," and "RUN" sequentially. If a user's pushes the button to begin the run, flowchart 5805 may proceed to display a timer display. If, on the other hand, a heart rate is detected, the device may proceed to flowchart 5811 which displays "PUSH," "TO," and "RUN" in sequence to prompt the user to begin the workout.

If a heart rate is detected first, the device may display "HRS" and "OK" to indicate that the heart rate sensor is working and transmitting data. If the shoe sensor has not been previously detected, the device may instruct the user to walk by displaying "WALK" for a half second every 1 second for 3 seconds. Alternatively, the athlete may be given the option to begin the workout without trying to detect a heart rate by displaying "OR," "PUSH," "TO," and "RUN" sequentially. If the shoe sensor is detected, the words "SHOE," and "OK" are displayed. Subsequently the user is instructed to activate the workout in flowchart 5809.

If, in either flowcharts 5805 and 5807, a sensor is not detected and the user does not elect to initiate the workout, a timer of a predefined length is started where the user is instructed to initiate the run as illustrated in flowcharts 5811 and 5813. The timer may, for example, be a 15 minute timer, a 20 minute timer, a 30 minute timer or the like. Once the timer expires, the display may return to displaying at time of day or some other default information. In each of flowcharts 5801-5813, the sensors that have been detected may be indicated by a corresponding icon on the display. For example, a heart icon may be displayed to represent a heart rate sensor while a shoe icon may be displayed to represent a shoe based sensor. In one or more arrangements, the icon may be displayed in alternate fashions to indicate that the sensors are in the process of being detected. For example, a heart icon may be displayed as a red blinking heart or a shoe may be displayed as a red blinking shoe icon.

Figure 59:
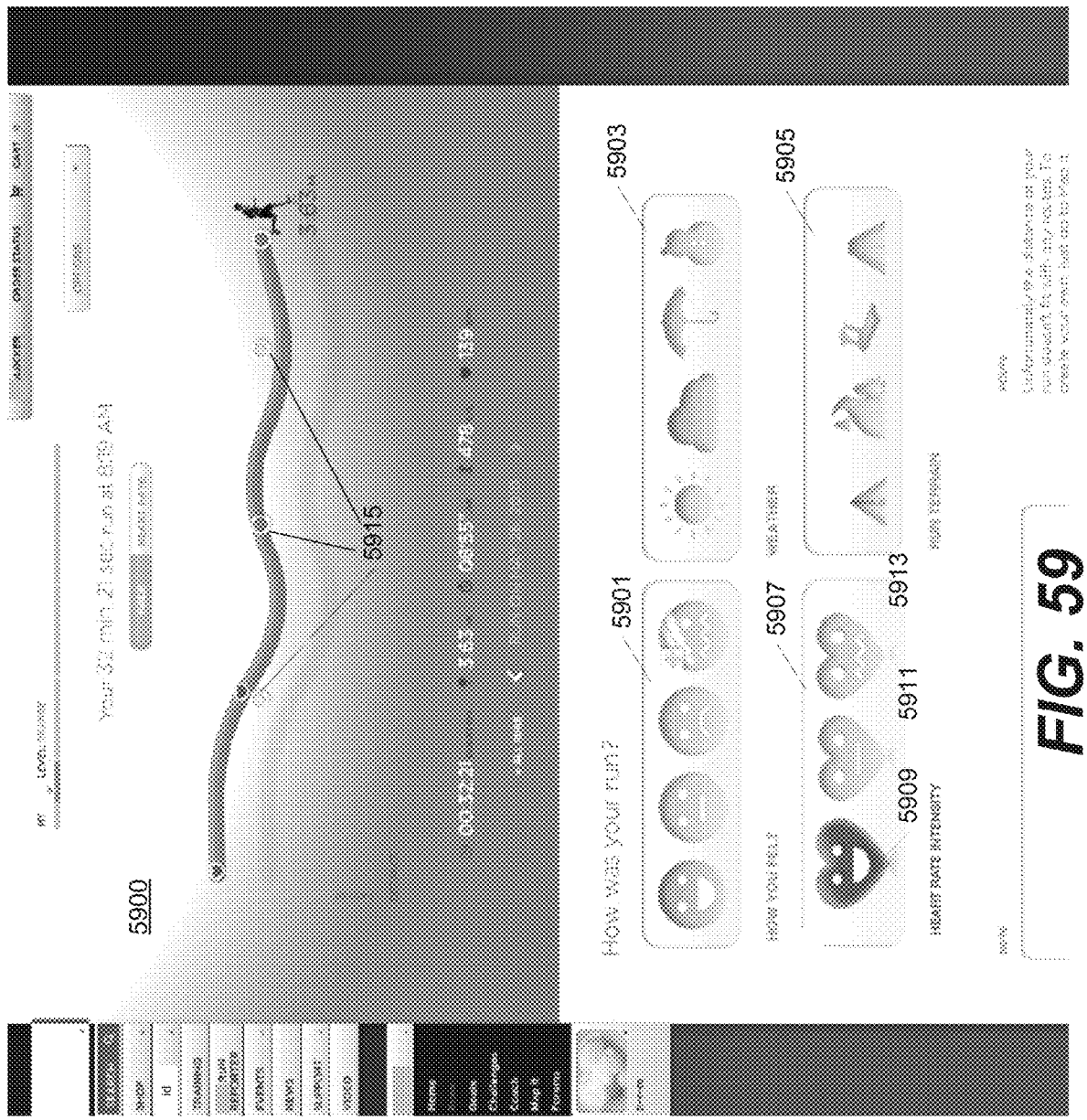
FIG. 59 illustrates an example user interface through which a user may indicate a heart rate intensity of an athletic activity session according to one or more aspects described herein.

FIG. 59 illustrates another example user interface displaying a user's heart rate during a workout session. In interface 5900, a user is provided with a plurality of tag options including a feeling or condition (e.g., mood or physical conditions such as sick, tired, happy, energetic, etc.) tag 5901, a weather tag 5903 and a run terrain tag 5905. Additionally, interface 5900 allows a user to specify a heart rate intensity using tag option 5907. Heart rate intensity may include the subjective feeling or assessment of the user regarding their heart rate during the run and/or perceived level of effort or difficulty. For example, the first heart rate intensity tag 5909 may indicate a comfortable heart rate while tag 5911 may indicate a heart rate intensity where the user was required to exert him or herself to a greater extent than a comfortable jog or fast paced walk. Further, tag 5913 may indicate a heart rate intensity where the user had to maximize his or her effort. In one or more arrangements, a system may automatically tag the heart rate intensity based on the user's actual recorded heart rate for the athletic activity session. For example, if the user averaged 80% above his or her resting heart rate, a high intensity heart rate indicator (e.g., indicator 5913) may be selected or used to tag the activity session. In another example, if the user's average heart rate during the activity session is 65% above his or her resting heart rate, the workout session may be labeled with a medium heart rate intensity tag (e.g., indicator 5911).

Additionally, indicators 5915 may be displayed on the graph as mile markers or markers for a predefined distance. For example, indicators 5915 may mark every half mile, every 200 feet, every 100 steps and the like. In other instances, the indicators may correspond to manual markings specified by the user during a workout session (e.g., whenever a user presses a mark button or other predefined button). Accordingly, those manual markings may be displayed on the graph upon uploading the data to a performance monitoring site and system (e.g., a remote service provider website).

Figure 60:
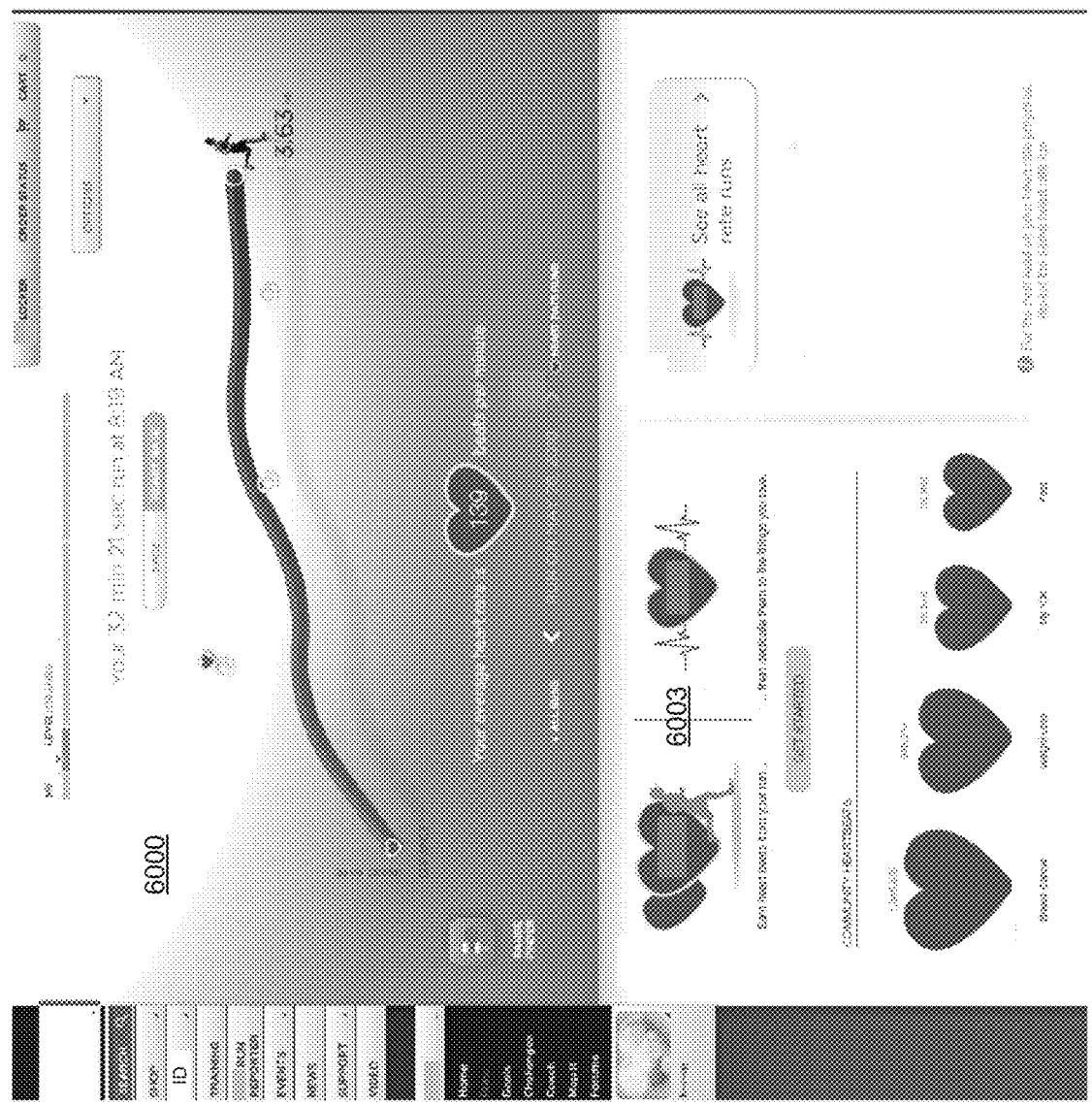
FIG. 60 illustrates an example user interface for displaying heart rate data versus distance according to one or more aspects described herein.
Figure 61:
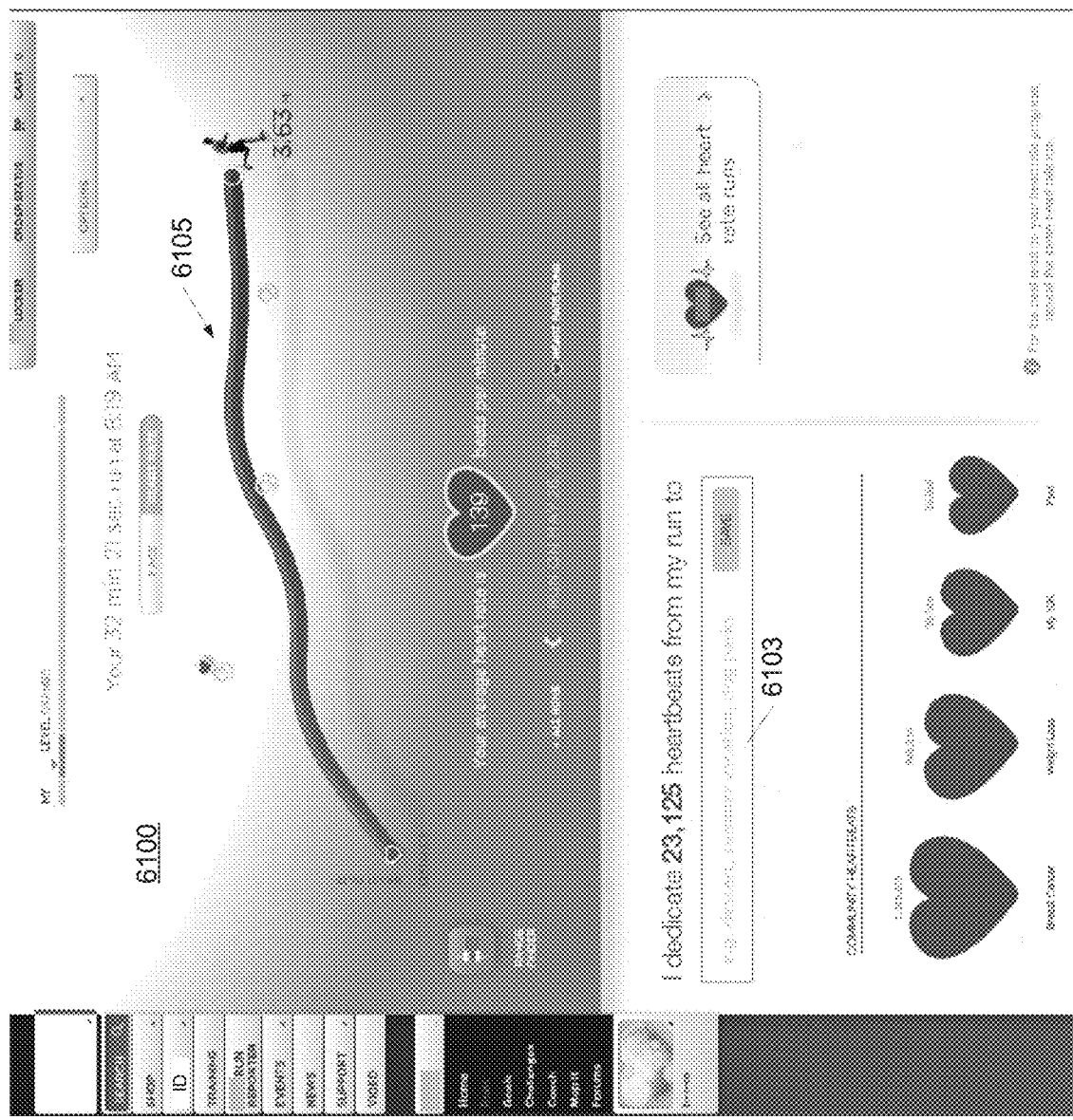
FIGS. 61 and 62 illustrate example user interfaces through which users may dedicate or label earned reward credits according to one or more aspects described herein.
Figure 62:
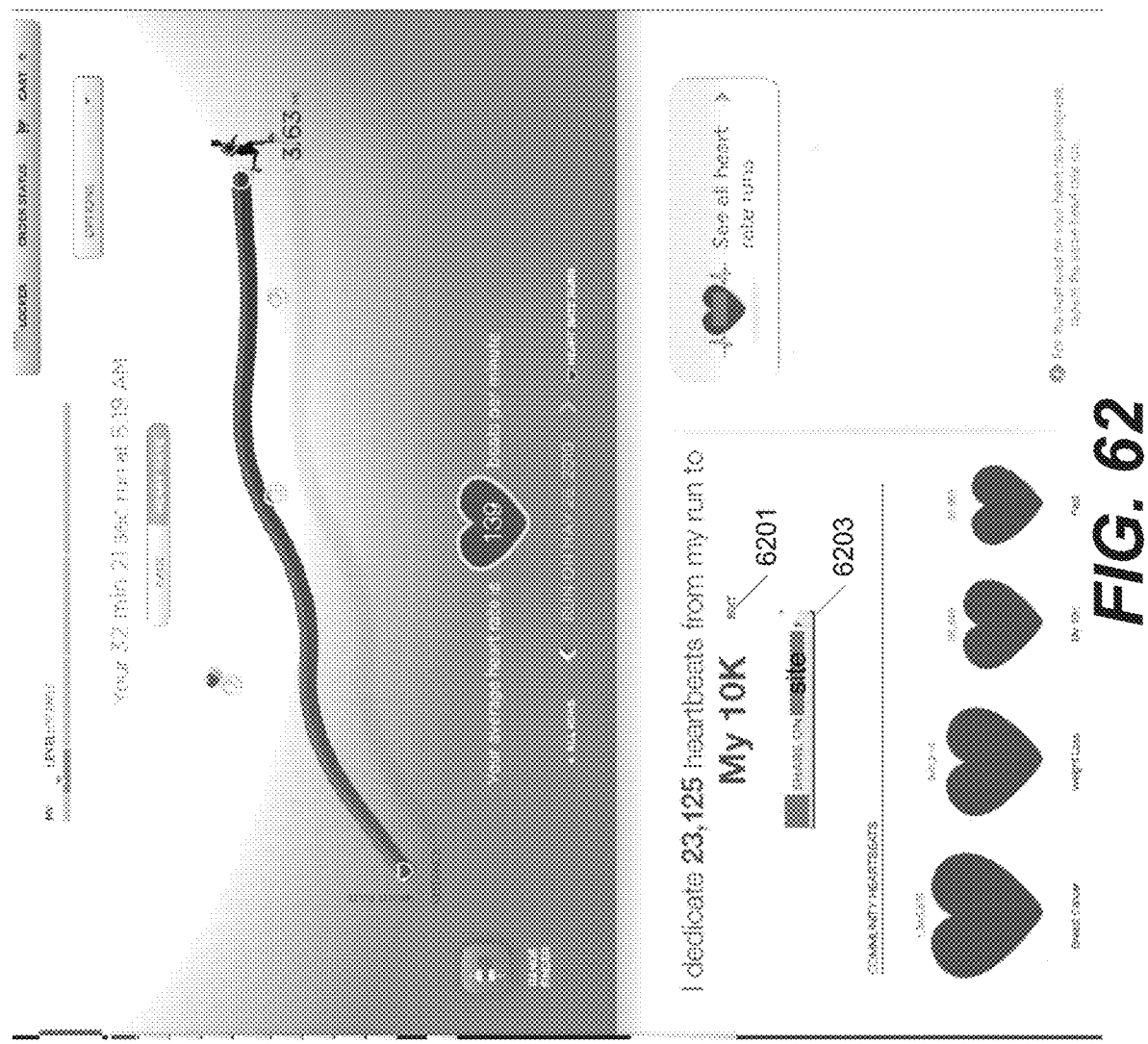

FIGS. 60-62 illustrate a series of example interfaces through which a user may earn a number of credits through the recordation of heart rate information. The credits earned may be used for bragging rights or may act as currency for purchase of products or services. In interface 6000, for example, a user may be encouraged to begin earning heart beats (e.g., a type of credit) by performing heart rate activities. The user may then dedicate the heart beats to one or more of the user's interests. Interface 6000 illustrates a community heart beats dedication display 6003 in which various interests, causes, organizations and the like are listed. A number of heart beats users have dedicated to each interest, cause or organization may be displayed in association with each of the interests, causes and/or organizations (e.g., a 10K run, the New York Marathon, weight loss, breast cancer, vacation, dessert, dog parks, etc.). The display 6003 may include the interests, causes and/or organizations having the greatest number of heart beats or other credits dedicated. Accordingly, the credits or heart beats may be used to raise awareness of one or more interests, causes and/or organizations. In some arrangements, the credits may be associated with a monetary value. For example, a system, company, user, site or the like may donate an amount of money to an interest, cause or organization upon the interest, cause or organization having a specified number of credits (e.g., heart beats) dedicated thereto.

Credits or currency may have expiration dates in one or more examples. The expiration dates may be refreshed (e.g., extended) upon the user performing additional workouts or adding to the credit or currency pool. In other cases where a user might not have performed any additional workouts or added currency or credits to the pool within an expiration time of one or more credits in the pool, those one or more credits may expire (e.g., be removed from the pool). Different credits or currency within the earned credits pool may have different expiration dates, times and periods. For example, credits earned for one type of athletic activity may have an effective or expiration period of 2 weeks while credits earned for another type of athletic activity may have an expiration period of 1 week.

FIG. 61 illustrates an example interface 6100 through which a user may specify the interest, cause or organization to which a number of heart beats may be dedicated. For example, field 6103 may be used by the user to enter the dedication target. In one or more arrangements, the user may further specify the number of heart beats that he or she wishes to dedicate. Accordingly, a user may dedicate fewer than all of the credits or heart beats that the user has accumulated and that have not yet been dedicated. Furthermore, portion of graph 6105 that correspond to the dedicated number of heart beats or other credits may be displayed differently. Accordingly, the user may visually determine how the heart beats earned from a particular run (e.g., represented by graph 6105) are dedicated. A legend (not shown) may also be displayed to identify the various interests, causes, organizations and the like.

FIG. 62 illustrates an example interface displayed upon the user confirming the organization, cause or interest to which the heart beats are to be dedicated. The user may further edit the dedication using option 6201 or share the dedication on a social community site such as FACEBOOK through option 6203.

Figure 63:
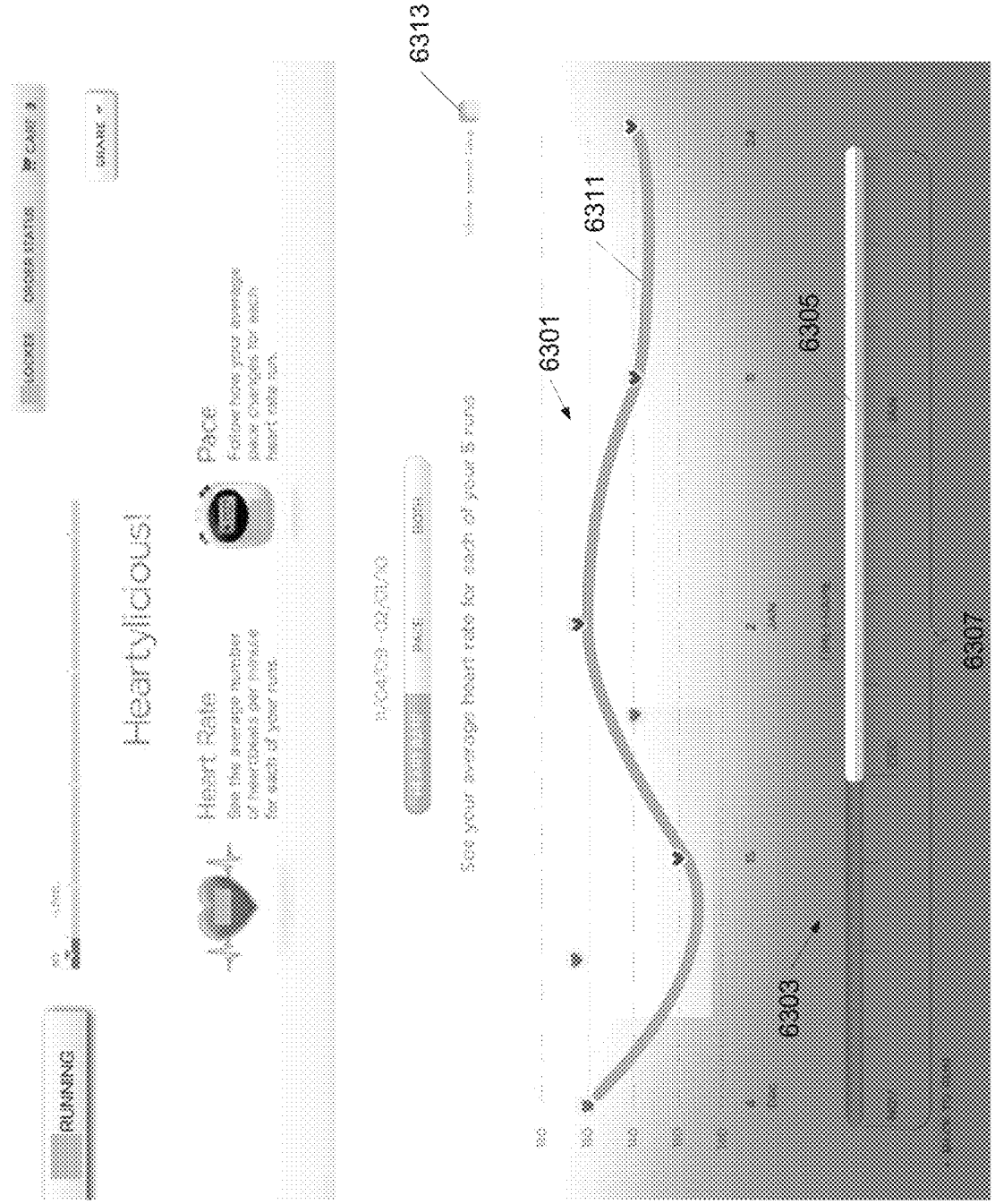
FIG. 63 illustrates an example interface in which a trendline corresponding to heart rate information and/or other metrics is displayed for multiple workouts according to one or more aspects described herein.

FIG. 63 illustrates a workout activity graph 6301 identifying the user's average heart rate during one or more workout sessions. In the illustrated example, the user's average heart rate is displayed over a previous 7 workouts in the past two months. The average heart rate is identified by heart rate marker 6309. Line graph 6311 identifies the trendline corresponding to the average heart rates recorded for the 7 workouts. Trendlines may be useful since average heart rates might not provide a user a good sense of progress or relative performance. In some instances, absolute heart rate measurements might not allow the user to detect or perceive his or her progress. The user may use control 6303 to increase the size of the time frame (e.g., by expanding span bar 6305) and/or move the time frame (e.g., by moving span bar 6305) along timeline 6307. The trendline may then adjust appropriately based on the heart rate data within that time frame (rather than the entire set of available heart rate data). Graph 6301 may automatically adjust and in real-time based on the operation of control 6303. A user may toggle the trendline showing by selecting option 6313. If option 6313 is turned off, the graph 6301 might only display the heart rate markers and average heart rates without the displaying the trend.

In one or more examples, a user may select a workout from multi-workout graph 6301 to cause the system to generate and display a particular heart rate or pace graph for a selected workout session. For example, the generated and displayed heart rate or pace graph may display more detailed heart rate or pace information (e.g., every minute, every 30 minutes, every hour) for the workout session or for that workout day. A maximum and minimum heart rate may also be specified.

The methods and features recited herein may further be implemented through any number of computer readable media that are able to store computer readable instructions. Examples of computer readable media that may be used include RAM, ROM, EEPROM, flash memory or other memory technology, CD-ROM, DVD, or other optical disc storage, magnetic cassettes, magnetic tape, magnetic storage and the like.

While illustrative systems and methods described herein embodying various aspects are shown, it will be understood by those skilled in the art that the invention is not limited to these embodiments. Modifications may be made by those skilled in the art, particularly in light of the foregoing teachings. For example, each of the elements of the aforementioned embodiments may be utilized alone or in combination or sub-combination with the elements in the other embodiments. It will also be appreciated and understood that modifications may be made without departing from the true spirit and scope of the present invention. The description is thus to be regarded as illustrative instead of restrictive on the present invention.

What is claimed is:

1. An athletic performance monitoring system comprising:
   a data collection module comprising a processor and memory operatively coupled to the processor, the memory storing computer readable instructions that, when executed, cause the data collection module to:
      detect a presence of one or more athletic activity sensors,
      poll the one or more athletic activity sensors for athletic performance data, and
      receive the athletic performance data;
   a sensor configured to measure an athletic activity parameter that includes a heart rate of a user performing an athletic activity,
   wherein, when the athletic performance monitoring system is used to detect athletic activity of the user, the data collection module is configured to collect heart rate information through the sensor for a plurality of activity types, and configured to provide the user with a plurality of heart beat credits that are configured to be earned and dedicated by the user to one or more interests of the user.

2. The athletic performance monitoring system of claim 1, wherein the data collection module is configured to receive the athletic performance data wirelessly from the one or more athletic activity sensors.

3. The athletic performance monitoring system of claim 1, wherein at least one of the plurality of heart beat credits has an expiration date that is extended upon the user performing an additional workout.

4. A method comprising:
   generating, by a computing device, a graph for an athletic activity comprising heart rate information, wherein generating the graph is performed after completion of the athletic activity;
   generating a heart rate profile of a user for a workout, from the completed athletic activity, wherein the user is alerted when the workout meets a predefined heart rate profile with specified portions of the workout falling within multiple heart rate ranges, and, wherein the user is provided with a plurality of heart beat credits, the plurality of heart beat credits configured to be earned and dedicated by the user to one or more interests of the user;
   generating, by the computing device, a heart rate range control including an upper limit control element and a lower limit control element;
   receiving a first user selection of a first heart rate range after the graph has been generated, wherein receiving the first user selection of the first heart rate range includes:
      receiving user input indicating a change in a position of at least one of the upper limit control element and the lower limit control element; and
      in response, determining the first heart rate range, wherein the first heart rate range is a range of heart rates between a lower heart rate limit corresponding to the lower limit control element and an upper heart rate limit corresponding to the upper limit control element;
   determining, by the computing device, a first portion of the graph corresponding to the selected first heart rate range in response to receiving the first user selection; and
   visually identifying the first portion of the graph differently from at least one other portion of the graph not corresponding to the selected first heart rate range.

5. The method of claim 4, further comprising:
   generating, by the computing device, a display indicating a number of heart beat credits dedicated to the one or more interests of the user.

6. The method of claim 4, further comprising:
   receiving a second user selection of a second heart rate range;
   determining a second portion of the graph corresponding to the selected second heart rate range, the second portion being different from the first portion; and
   visually identifying the second portion of the graph in a manner different from the first portion of the graph and simultaneously with visually identifying the first portion of the graph.

7. The method of claim 4, further comprising:
   determining a percentage of the activity spent in the first heart rate range; and
   displaying the percentage.

8. The method of claim 4, further comprising displaying the heart rate range control as an axis of the graph.

9. The method of claim 4, further comprising displaying at least one marker in the graph, wherein the marker is indicative of at least one of: a highest heart rate and a lowest heart rate.

10. The method of claim 9, wherein the at least one of the highest heart rate and the lowest heart rate is determined based on an average heart rate of a previous predetermined amount of time and a subsequent predetermined amount of time.

* * * * *